US008114832B2

(12) United States Patent
Gebbink et al.

(10) Patent No.: US 8,114,832 B2
(45) Date of Patent: Feb. 14, 2012

(54) METHOD FOR DETECTING AND/OR REMOVING A PROTEIN COMPRISING A CROSS-BETA STRUCTURE FROM A PHARMACEUTICAL COMPOSITION

(75) Inventors: Martijn Frans Ben Gerard Gebbink, Eemnes (NL); Barend Bouma, Houten (NL)

(73) Assignee: Crossbeta Biosciences B.V., Utrecht (NL)

( * ) Notice: Subject to any disclaimer, the term of this patent is extended or adjusted under 35 U.S.C. 154(b) by 0 days.

(21) Appl. No.: 11/181,040

(22) Filed: Jul. 13, 2005

(65) Prior Publication Data

US 2007/0015206 A1 Jan. 18, 2007

(51) Int. Cl.
*A61K 35/00* (2006.01)
*A61K 38/00* (2006.01)

(52) U.S. Cl. ...... 514/2; 424/278.1; 424/9.322; 530/350; 530/390.5

(58) Field of Classification Search ............... 424/278.1; 514/2
See application file for complete search history.

(56) References Cited

U.S. PATENT DOCUMENTS 5,051,185 A 9/1991 Watanabe et al.
5,151,082 A 9/1992 Gorsuch et al.
5,180,615 A 1/1993 Havens
5,216,127 A 6/1993 Hirai et al.
5,221,628 A 6/1993 Anderson et al.
5,230,996 A 7/1993 Rath et al.
5,276,059 A 1/1994 Caughey et al.
5,278,189 A 1/1994 Rath et al.
5,288,490 A 2/1994 Budzynski et al.
5,449,663 A 9/1995 Bicher
5,491,129 A 2/1996 Shalteil
5,589,154 A 12/1996 Anderson
5,591,431 A 1/1997 Schasteen et al.
5,599,678 A 2/1997 Kraus et al.
5,624,908 A 4/1997 Bicher
5,650,418 A 7/1997 Rath et al.
5,700,447 A 12/1997 Bucala et al.
5,731,007 A 3/1998 Chung et al.
5,733,524 A 3/1998 Bucala et al.
5,733,933 A 3/1998 Bucala et al.
5,750,349 A 5/1998 Suzuki
5,780,587 A 7/1998 Potter
5,780,615 A 7/1998 Bucala et al.
5,785,187 A * 7/1998 Lipman et al. ............... 211/59.1
5,786,324 A 7/1998 Gray et al.
5,801,200 A 9/1998 Bucala et al.
5,817,626 A 10/1998 Findeis et al.
5,834,028 A 11/1998 Kunihiro et al.
5,851,996 A 12/1998 Kline
5,854,215 A 12/1998 Findeis et al.
5,869,534 A 2/1999 Bucala et al.
5,935,927 A 8/1999 Vitek et al.
5,948,763 A 9/1999 Soto-Jara et al.
5,955,343 A 9/1999 Holmes et al.
5,958,883 A 9/1999 Snow
5,981,697 A 11/1999 Kraus et al.
5,985,242 A 11/1999 Findeis et al.
5,985,607 A 11/1999 Delcuve et al.
6,001,331 A 12/1999 Caprathe et al.
6,034,211 A 3/2000 Kelly
6,037,327 A 3/2000 Castillo et al.
6,037,458 A 3/2000 Hirai et al.
6,136,548 A 10/2000 Anderson
6,161,547 A 12/2000 Barbut
6,184,030 B1 2/2001 Katoot et al.
6,242,473 B1 6/2001 Hellstrand et al.
6,310,046 B1 10/2001 Duffy et al.
6,319,498 B1 * 11/2001 Findeis et al. ............... 424/94.3
6,340,783 B1 1/2002 Snow
6,372,473 B1 4/2002 Moore et al.
6,399,314 B1 6/2002 Krishnamurthy
6,410,598 B1 6/2002 Vitek et al.
6,436,969 B1 8/2002 Khalifah et al.
6,462,171 B1 10/2002 Soto-Jara et al.
6,471,960 B1 10/2002 Anderson
6,537,969 B1 3/2003 Blass
6,641,815 B2 11/2003 Duffy et al.

(Continued)

FOREIGN PATENT DOCUMENTS

AU 2003214375 B2 10/2003

(Continued)

OTHER PUBLICATIONS

Gupta-Bansal et al. (1998) "Congo red inhibits proteoglycan and serum amyloid P binding to amyloid beta fibrils", J. Neurochem., vol. 10, No. 1, pp. 292-298.*
Voropai et al. (2003) "Spectral properties of thioflavin T and its complexes with amyloid fibrils", J. Appl. Spectrosc., vol. 70, pp. 868-874.*
Frid et al. (2007) Congo red and protein aggregation in neurodegenerative diseases, Brain. Res. Rev., vol. 53, No. 1, pp. 135-160.*
Lueking et al. (2005) Protein biochips: A new and versatile platform technology for molecular medicine, Drug. Discov. Today, vol. 10, No. 11, pp. 789-794.*

(Continued)

*Primary Examiner* — Anand Desai
*Assistant Examiner* — Samuel Liu
(74) *Attorney, Agent, or Firm* — TraskBritt, P.C.

(57) ABSTRACT

The invention relates to the detection and/or removal of conformationally altered proteins and/or molecules comprising a cross-β structure from a pharmaceutical composition. Disclosed is that unwanted and/or toxic side effects of pharmaceuticals are caused by proteins present in the pharmaceutical and adopting a cross-β structure conformation. Further disclosed is a method for detecting a protein in a pharmaceutical composition, the method comprising: contacting the pharmaceutical composition or any of its constituents comprising a protein with at least one cross-β structure-binding compound resulting in a bound protein and/or peptide comprising a cross-β structure and; detecting whether bound protein and/or peptide comprising a cross-β structure are present in the pharmaceutical composition or any of its constituents comprising a protein. Further described are methods for removing cross-β structures from a pharmaceutical composition and controlling the manufacture of a pharmaceutical composition.

11 Claims, 7 Drawing Sheets

U.S. PATENT DOCUMENTS 6,686,144 B2 2/2004 McLeod et al.
6,689,275 B1 * 2/2004 Gupta .......................... 210/647
6,960,465 B1 * 11/2005 Papoutsakis et al. ...... 435/252.3
7,041,287 B2 5/2006 Muzykantov et al.
7,135,181 B2 11/2006 Jensen et al.
7,172,875 B2 2/2007 Kuret et al.
7,196,064 B2 3/2007 McAnalley et al.
7,517,525 B2 4/2009 Prenner et al.
2002/0065327 A1 5/2002 Jiao et al.
2002/0102261 A1 8/2002 Raso
2002/0114796 A1 8/2002 Eibl
2002/0133019 A1 9/2002 Klunk et al.
2002/0187157 A1 12/2002 Jensen et al.
2002/0187158 A1 12/2002 Mahler et al.
2003/0017995 A1 1/2003 Khalifah et al.
2003/0050245 A1 3/2003 Gebbink et al.
2003/0059921 A1 3/2003 Sahni et al.
2003/0072770 A1 4/2003 McAnalley et al.
2003/0086938 A1 5/2003 Jensen et al.
2003/0087407 A1 5/2003 Soto-Jara et al.
2003/0109435 A1 6/2003 Prenner et al.
2003/0118593 A1 6/2003 Dan et al.
2003/0143223 A1 7/2003 Cabezas et al.
2003/0165458 A1 9/2003 Cabezas et al.
2003/0176365 A1 9/2003 Blass
2003/0236391 A1 12/2003 Klunk et al.
2004/0013647 A1 1/2004 Solomon et al.
2004/0253595 A1 * 12/2004 Nakamura et al. ................ 435/6
2005/0142208 A1 * 6/2005 Yoo et al. ...................... 424/529
2005/0142611 A1 * 6/2005 Vodyanoy et al. ............. 435/7.1
2006/0045853 A1 * 3/2006 Kroon-Batenburg et al. .. 424/50
2006/0058232 A1 * 3/2006 Luo et al. ....................... 514/12
2006/0270599 A1 11/2006 Gebbink et al.
2006/0292683 A1 * 12/2006 Gebbink et al. ............. 435/243
2007/0003552 A1 1/2007 Gebbink et al.
2007/0015133 A1 1/2007 Gebbink et al.
2007/0015206 A1 1/2007 Gebbink et al.
2007/0151133 A1 7/2007 Hunsaker
2008/0044429 A1 * 2/2008 Johnson et al. ............ 424/172.1
2008/0118529 A1 5/2008 Gebbink et al.
2008/0207488 A1 8/2008 Gebbink et al.
2008/0220446 A1 9/2008 Gebbink et al.
2008/0241165 A1 10/2008 Kroon-Batenburg et al.
2008/0249606 A1 10/2008 Gebbink et al.
2008/0267948 A1 10/2008 Gebbink et al.
2008/0299212 A1 12/2008 Kim et al.
2009/0142377 A1 6/2009 Gebbink et al.
2009/0155254 A1 6/2009 Gebbink et al.
2009/0191228 A1 * 7/2009 Gebbink et al. ........... 424/184.1
2009/0202980 A1 8/2009 Gebbink et al.
2010/0015126 A1 1/2010 Gebbink et al.

FOREIGN PATENT DOCUMENTS

DE 197 35 902 A1 2/1999
EP 0 234 051 9/1987
EP 0 319 144 A1 6/1989
EP 0 321 703 A1 6/1989
EP 0 494 848 A1 7/1992
EP 0 589 181 3/1994
EP 0589181 3/1994
EP 0 955 312 A2 11/1999
EP 1 130 031 A1 9/2001
EP 1 179 588 A1 2/2002
EP 1 152 004 B1 5/2003
EP 1 380 290 1/2004
EP 1449536 A1 * 8/2004
EP 1 978 362 A2 10/2008
EP 1 536 778 B1 12/2008
EP 1 257 582 B1 4/2009
JP 171638/1989 7/1998
JP 509457/1998 9/1998
JP 2001-519753 10/2001
WO WO 90/14102 11/1990
WO WO 91/18610 12/1991
WO WO 91/19488 12/1991
WO WO 92/11847 7/1992
WO WO 92/15677 9/1992
WO WO 94/01116 1/1994
WO WO 94/20083 9/1994
WO WO 94/28909 12/1994
WO WO 95/20979 8/1995
WO WO 96/15799 5/1996
WO WO 96/39834 12/1996
WO WO 97/21728 6/1997
WO WO 97/26919 7/1997
WO WO 97/46547 12/1997
WO WO 98/06418 2/1998
WO WO 99/02545 1/1999
WO WO 99/09999 3/1999
WO WO 99/21565 5/1999
WO WO 99/47072 9/1999
WO WO 00/04052 1/2000
WO WO 00 09562 A1 2/2000
WO WO 00/59493 10/2000
WO WO 00/66717 11/2000
WO WO 00/68263 11/2000
WO WO 01/07474 A1 2/2001
WO WO 01/12598 A2 2/2001
WO WO 01/50134 A2 7/2001
WO WO 01/53335 A3 7/2001
WO WO 01/58476 A2 8/2001
WO WO 01/62284 A2 8/2001
WO WO 01/62799 A2 8/2001
WO WO 01/77284 10/2001
WO WO 02/16333 A2 2/2002
WO WO 02/28441 4/2002
WO WO 02/053092 7/2002
WO WO 02/097444 12/2002
WO WO 02/097444 A2 12/2002
WO WO 02/099098 A1 12/2002
WO WO 02/99098 A1 12/2002
WO WO03/002141 1/2003
WO WO 03/006893 A2 1/2003
WO WO 03/064446 A2 8/2003
WO WO 03/073106 9/2003
WO WO 03/073106 A2 9/2003
WO WO 2004/004698 1/2004
WO WO 2004/004698 A2 1/2004
WO WO 2004/007545 1/2004
WO WO 2005/019434 A2 3/2005
WO WO 2005/042569 5/2005
WO WO 2005/042569 A1 5/2005
WO WO 2006/006172 A2 1/2006
WO WO 2006/098621 A2 9/2006
WO WO 2006/101387 9/2006
WO WO 2007/008069 A2 1/2007
WO WO 2007/008070 A2 1/2007
WO WO 2007/008071 A2 1/2007
WO WO 2007/008072 1/2007
WO WO 2007/008073 A2 1/2007
WO WO 2007/018400 A1 2/2007
WO WO 2007/094668 8/2007
WO WO 2007/108675 A1 9/2007

OTHER PUBLICATIONS

Narang et al. (1997) Enhanced biosensor performance using an avidin-biotin bridge for antibody immobilization, Proc. SPIE, vol. 2980, pp. 187-194.*

Torrent et al. (20040 Insights into alternative prion protein topologies induced under high hydrostatic pressure, J. Phys. Condens.Matter., vol. 16, Issue 14, pp. S1059-S1065.*

Sparknotes (2008, updated) “Amino acids and proteins”, http://www.sparknotes.com/health/aminoacids/section1.html, pp. 1-7.*

Thirumalai et al. (2003) Emerging ideas on the molecular basis of protein and peptide aggregation, Curr. Opin. Struct. Biol., vol. 13, No. 2, pp. 146-159.*

Jhamb et al. (2008) Immobilized chaperones: A productive alternative to refolding of bacterial inclusion body proteins, Process Biochem., vol. 43, pp. 587-597.*

Wu et al. (2008) The binding of thioflavin T and its neutral analog BTA-1 to protofibrils of the Alzheimer’s disease Abeta(16-22) peptide probed by molecular dynamics simulations, J. Mol. Biol., vol. 384, No. 3, pp. 718-729.*

Wang et al. (2008) Bacterial inclusion bodies contain amyloid-like structure, PLoS Biol., vol. 6, No. 8, pp. 1791-1801.*

Wikipedia (2009, updated) Hsp27, en.wikipedia.org/wiki/Hsp27, pp. 1-4.*
Hatters et al. (2001) The molecular chaperone, alpha-crystallin, inhibits amyloid formation by apolipoprotein C-II, J. Biol. Chem., vol. 276, No. 36, pp. 33755-33761.*
Garido C. (2002) Size matters: of the small HSP27 and its large oligomers, Cell Death. Differ. , vol. 9, No. 5, pp. 483-485.*
Rao et al. (2010)Thermo and pH stable ATP-independent chaperone activity of heat-inducible Hsp70 from Pennisetum glaucum, Plant Signal. Behav., vol. 5, No. 2, pp. 110-121.*
Johnstone et al. (1994) Monoclonal antibodies that recognize the native human thyrotropin receptor, Mol. Cell. Endocrinol., vol. 105, No. 2, pp. R1-R9.*
PCT International Search Report, PCT/NL2003/000501, dated Mar. 31, 2004.
PCT International Preliminary Examination Report, PCT/NL2003/000501, dated Oct. 28, 2004.
Adessi et al., Abstract, Beta-sheet breaker strategy for the treatment of Alzheimer's disease. Drug Development Res 56(2): 184-193, 2002.
Golabek et al., The interaction between Apolipoprotein E and Alzheimer's amyloid beta-peptide is dependent on beta-peptide conformation. J Biol Chem 271(18): 10602-10606, 1996.
Sigurdsson et al., Abstract, In vivo reversal of amyloid-beta lesions in the rat brain. J Neuropath Exp Neural 59(1): 11-17, 2000.
Wood et al., Abstract, Prolines and amyloidogenicity in fragments of the Alzheimer's peptide beta/A4. Biochemistry 34: 724-730, 1995.
Soto C., Abstract, Plaque busters: strategies to inhibit amyloid formation in Alzheimer's disease. Mol Med Today. 5(8):343-350, 1999.
Soto C et al., Abstract, Beta-sheet breaker peptides inhibit fibrillogenesis in a rat brain model of amyloidosis: implications for Alzheimer's therapy. Nat Med. 4(7):822-826, 1998.
Soto C et al., Abstract, Inhibition of Alzheimer's amyloidosis by peptides that prevent beta-sheet conformation. Biochem Biophys Res Commun. 226(3):672-680, 1996.
Soto C., Abstract, Alzheimer's and prion disease as disorders of protein conformation: implications for the design of novel therapeutic approaches. J Mol Med. 77(5):412-418, 1999.
Soto C., Abstract, Beta-amyloid disrupting drugs. CNS Drugs 12(5): 347-356, 1999.
Permanne B et al., Reduction of amyloid load and cerebral damage in a transgenic mouse model of Alzheimer's disease by treatment with a beta-sheet breaker peptide. Faseb J. 16(8):860-862, 2002.
Hetenyi et al., Abstract, Computational studies on the binding of beta-sheet breaker (BSB) peptides on amyloid beta A(1.42). J Molec Structure 542: 25-31, 2001.
Faculty of 1000 Biology: Evaluations for Maas C et al., J Biol Chem 2007 Jan 26 282 (4): 2229.36, http://www.f1000biology.com/article/id/1060927/evaluation.
Maas et al., "A Role for Protein Misfolding in Immunogenicity of Biopharmaceuticals," J Biol Chem, Jan. 26, 2007, pp. 2229-2236, vol. 282, No. 4. Abstract.
Rosenberg et al., "Effects of Protein Aggregates: An Immunologic Perspective," The AAPS Journal 2006, pp. E501-E507, vol. 8, No. 3.
Maas et al., "A Role for Protein Misfolding in Immunogenicity of Biopharmaceuticals," Daily Updated-Technology citing J Biol Chem, Jan. 26, 2007, pp. 2229-2236, vol. 282, No. 4.
Nemes et al., Cross-linking of ubiquitin, HSP27-parkin and αsynuclein by γ-glutanyl-c-lysine bonds Alzheimer's neurofibrillary tangles, The FASEB Journal, Published online May 7, 2004.
Wilhelmus et al., Specific association of small heat shock proteins with the pathological hallmarks of Alzheimer's disease brains, Neuropathology and Applied Neurobiology, 2006, pp. 119-130, vol. 32.
Adachi et al., Direct observation of photolysis-induced tertiary structural changes in hemoglobin, PNAS, Jun. 10, 2003, pp. 7039-7044. vol. 100, No. 12.
Blondelle et al., Abstract, Polyalanine-based peptides as models for self-associated beta-pleated-sheet complexes. Biochemistry 36: 8393-8400, 1997.
Bode et al., Antibody-directed Fibrinolysis, The Journal of Biological Chemistry (1989). pp. 944-948, vol. 264, No. 2.
Boehm et al., Antiangiogenic therapy of experimental cancer does not induct acquired drug resistance, Nature, 1997, pp. 404-407, vol. 390.
Bouma et al., "Glycation Induces Formation of Amyloid Cross-β Structure in Albumin," The Journal of Biological Chemistry, Oct. 24, 2003, pp. 41810-41819. vol. 278, No. 43.
Bouma et al., Efficacy and Stability of a Subunit Vaccine Based on Glycoprotein E2 of Classical Swine Fever virus, Vet Microbial., 66, 101-114 (1999).
Bouma, B. et al., Adhesion Mechanism of Human Beta(2)-Glycoprotein 1 to Phospholipids Based an its Crystal Structure, EMBO J., 18, 5166-5174 (1999).
Brandenburg, K., Koch, M.H. & Seydel, T.J., Biophysical Characterisation of Lysozyme Binding to LPS Re and Lipid A, Eur. J. Biochem., 258, 686-695 (1998).
Bronsveld et al., "Usc of glucose-insulin-potassium (GIK) in human septic shock." Critical Care Medicine, 1985, pp. 566-570. vol. 13. No. 7.
Butovsky, et al. Activation of Microglia by Aggregated Beta-Amyloid or Lipopolysaccharide Impairs MHC-II Expression and Renders them Cytotoxic whereas IFN-gamma and IL-4 Render them Proctective, Mol. Cell Neurosci., (2005).
Cardoso et al., "Aprotinin binding to amyloid fibrils," Eur. J. Biochem., 2000, pp. 2307-2311, vol. 267.
Chauhan et al., "Metal Cations Defibrillize the Amyloid Beta-Protein Fibrils," Neurochemical Research, 1997, pp. 805-809, vol. 22, No. 7.
Chothia et al., Canonical structures for the hypervariable regions of immunoglobulins, J. Mol. Biol., 1987, pp. 901-917, vol. 196.
Claessen et al., A Novel Class of Secreted Hydrophobic Proteins is Involved in Aerial Hyphae formation in Streptomyces coelicolor by Forming Amyloid-like Fibrils, Genes & Development, 2003, pp. 1714-1726, vol. 17, Cold Spring Harbor Laboratory Press.
Clean Set of Claims submitted in European copending case (EP Application No. 01912573.1), Dec. 28, 2007.
Cockerill et al., In vivo characterization of bioconjugate B cell toleragens with specificity for autoantibodies in antiphospholipid syndrome, International Immunopharmacology, Nov. 2003, pp. 1667-1675, vol. 3, No. 12.
Coraci et al., CD36, a Class B Scavenger Receptor, Is Expressed on Microglia in Alzheimer's Disease Brains and Can Mediate Production of Reactive Oxygen species in Response to β-Amyloid Fibrils, American Journal of Pathology, Jan. 2002, pp. 101-112, vol. 160, No. 1.
Cudic et al., Tetrahedron Letters, 2000, pp. 4527-4531, vol. 41.
De Laat, B., et al., IgG Antibodies That Recognize Epitope Gly40-Arg43 in Domain 1 of (beta)2-glycoprotein 1 Cause LAC and Their Presence Correlates Strongly with Thrombosis Blood, 105, 1540-1545 (2005).
De Laat, et al., Beta2-glycoprotein 1-dependent lupus anticoagulant highly correlates with thrombosis in the antiphospholipid syndrome, Blood, 104, 3598-3602 (2004).
Decision to grant a European patent pursuant to Article 97(1) EPC for European copending case (EP Application No. 01912573.1) dated Apr. 2, 2009.
Delgado et al., Antibodies against human cell receptors, CD36, CD41a and CD62P crossreact with porcine platelets, Cytometry Part B (Clinical Cytometry), 2003, pp. 62-67, vol. 56b.
Diaz-Avalos et al., Cross-beta Order and Diversity in Nanocrystals of an Amyloid-forming Peptide, Journal of Molecular Biology, 2003, pp. 1165-1175.
Doig et al., Binding of Laminin and Fibronectin by the Trypsin-resistant Major Structural Domain of the Crystalline Virulence Surface Array Protein of Aeromonas salmonicida, The Journal of Biological Chemistry, 1992, pp. 43-49, vol. 267, No. 1.
Dooley et al., Three-Dimensional Structure of an Open Form of the Surface Layer from the Fish Pathogen Aeromonas salmonicida, Journal of Bacteriology, Jan. 1989, pp. 190-197, vol. 171.
Dubois et al., Thrombin binding to GPIbalpha induces integrin alphaIIbbeta3 dependent platelet adhesion to fibrin in ex vivo flowing whole blood, Thrombosis and Haemostasis, Feb. 2004; pp. 233-237, vol. 91, No. 2.

Elangovan et al., The ubiquitin-interacting motif of 26S proteaosome subunit S5a induces A549 lung cancer cell death, Biophys. Res. Comm., 2007, pp. 226-230, vol. 364.
Esler et al., Deposition of soluble amyloid-beta onto amyloid templates: With application for the identification of amyloid fibril extension inhibitors, Methods Enzymol., 1999, pp. 350-374, vol. 309.
European Patent Office Notification for Application No. 03 762 927.6 dated Jul. 26, 2007.
European Patent Office Oral Proceedings for Application No. 03 762 927.6 dated Feb. 18, 2008.
European Patent Office Summary of Facts and Submission for Application No. 03 762 927.6 dated May 30, 2008.
Fan et al., Preclinical study of influenza virus A M2 peptide conjugate vaccines in mice, ferrets, and rhesus monkeys, Vaccine, Aug. 13, 2004, pp. 2993-3003, vol. 22, No. 23-24, Butterworth Scientific, Guildford, GB.
Fassbender, K. et al., The LPS receptor (CD14) Links Innate Immunity with Alzheimer's Disease, FASEB J., 18, 203-205 (2004).
Fleury et al., Abstract, Molecular assembly of plasminogen and tissue-type plasminogen activator on an evolving fibrin surface, Eur. J. Biochem., 1993, pp. 549-556, vol. 216.
Folkman, J., Clinical applications of research on angiogenesis, Semin. Med. Beth Israel Hosp., 1995b, pp. 1757-1763, vol. 333.
Folkman, J., Fighting cancer by attacking its blood supply, SE Am., 1996, pp. 150-154, vol. 275.
Folkman, Judah, Abstract, Angiogenesis in cancer, vascular, rheumatoid and other diseases, Nat. Med., 1995, pp. 27-31, vol. 1.
Fu et al. (2008) Sulfate stabilizes the folding intermediate more than the native structure of endostatin. Archives of Biochemistry and Biophysics 471: 232-239.
Fulmer, Tim, New Islets—No Immunosuppressives, Science-Business eXchange, Sep. 25, 2008, pp. 1-19, vol. 1, No. 34.
Ge et al., Fibrinogen Degradation Product Fragment D Induces Endothelial Cell Detachment by Activation of Cell-mediated Fibrinolysis, J. Clin. Invest, Dec. 1992, pp. 2508-2516, vol. 90.
Gebbink et al., Amyloids—A Functional Coat for Microorganisms, Nature Reviews Microbiology, Apr. 2005, pp. 333-341, vol. 3.
Genbank Public DNA Database, Accession No. 2B4X_I., Mourey et al., Sep. 27, 2005, pp. 1-3 <http://www.ncbi.nlm.nih.gov...> (visited Jan. 15, 2009).
Genbank Public DNA Database, Accession No. 2B4X_L., Mourey et al., Sep. 27, 2005, pp. 1-3 <http://www.ncbi.nlm.nih.gov...> (visited Jan. 15, 2009).
Geylis et al., Human monoclonal antibodies against amyloid-beta from healthy adults, Neurobiol. Aging, 2005, vol. 26, pp. 597-606.
Giannetti et al., Fibers of tau fragments, but no full length tau, exhibit a cross β-structure: Implications for the formation of paired helical filaments, Protein Science, 2000, pp. 2427-2434, vol. 9.
Goldsteins et al., Exposure of cryptic epitopes on transthyretin only in amyloid and in amyloidogenic mutants, Proceedings of the National Academy of Sciences of USA, Mar. 16, 1999, pp. 3108-3113, vol. 96, No. 6, National Academy of Science, Washington, DC, USA.
Gonzalez-McQuire et al., Fabrication of hydroxyapatite sponges by dextran sulphate/amino acid templating, Biomaterials, Jun. 3, 2005, pp. 6652-6656, vol. 26, No. 33.
Griffioen et al., Anginex, a designed peptide that inhibits angiogenesis, Biochem. J., 2001, pp. 233-242, vol. 354.
Grudzielanek et al., Solvational Tuning of the Unfolding, Aggregation and Amyloidogenesis of Insulin, Journal of Molecular Biology, Aug. 26, 2005, pp. 579-894, vol. 352, No. 4.
Gur et al., Editorial in Cell, Lon Takes in the Aromatic Fragrance of Unfolded Proteins, Genes Dev., 2008, pp. 2267-2277, vol. 22.
Han et al. (2007) Contributions of Zn(II)-binding to the structural stability of endostatin. FEBS Letters 581: 3027-3032.
He et al, (2006) Deficiency of disulfide bonds facilitating fibrillogenesis of endostatin. J. Biol. Chem. 281(2): 1048-1057.
Heckels et al., Vaccination Against Gonorrhoea: The Potential Protective Effect of Immunization with a Synthetic Peptide Containing a Conserved Epitope of Gonococcal Outer Membrane Protein IB, Vaccine, Jun. 1, 1990, pp. 225-230, vol. 8, No. 3, Butterworth Scientific, Guildford, GB.
Hock et al., Generation of antibodies specific for beta-amyloid by vaccination of patients with Alzheimer disease, Nature Medicine, Nov. 2002, pp. 1270-1275, vol. 8, No. 11, Nature America, New York, US.
Hoppener et al., Islet Amyloid and Type 2 Diabetes Mellitus. N. Engl. J. Med., 343, 411-419 (2000).
Hoppener, J.W. et al., Extensive Islet Amyloid Formation Is Induced by Development of Type II Diabetes Mellitus and Contributes to Its Progression: Pathogenesis of Diabetes in a Mouse Mode, Diabetologia, 42, 427-434(1999).
Horbach et al., Lupus Anticoagulant is the Strongest Risk Factor for both Venous and Arterial Thrombosis in Patients with Systemic Lupus Erythematosus, Comparison between Different Assays for the Detection of Antiphospholipid Antibodies, Thromb. Haetmost., 76, 916-924 (1996).
Horbach, et al., The Prevalence of a Non-phospholipid-binding Form of Beta2-Glycoprotein I in Human Plasma—Consequences for the Development of Anti-Beta2-glycoprotein I Antibodies. Thromb. Haemost., 80, 791-797 (1998).
Hrncic et al., Antibody-mediated resolution of light chain-associated amyloid deposits, American Journal of Pathology, Oct. 2000, pp. 1239-1246, vol. 157, No. 4, Philadelphia, PA, US.
Hu et al., Abstract, Procoagulant activity in cancer cells is dependent on tissue factor expression, Oncol Res., 1994, pp. 321-327, vol. 6, No. 7.
Hu et al., Angiogenin Enhances Actin Acceleration of Plasminogen Activation, Biochemical and Biophysical Communications, Dec. 15, 1993, pp. 682-687, vol. 197, No. 2.
Huang et al., Probing Three-Dimensional Structure of Bovine Serum Albumin by Chemical Cross-Linking and Mass Spectrometry, Journal of American Soc. Mass Spectrum, Aug. 2004, pp. 1237-1247, vol. 15, No. 8.
Hulst et al., Glycoprotein El of Hog Cholera Virus Expressed in Insect Cells Protects Swine from Hog Cholera, J Virol., 67, 5435-5442 (1993).
Husemann et al., Scavenger receptor class B type 1 (SR-Bi) mediates adhesion of neonatal murine microglia to fibrillar β-amyloid, Journal of Neuroimmunology, 2001, pp. 142-150, vol. 114.
Isik et al., Abstract, Vitronectin decreases microvascular endothelial cell apoptosis, J. Cell Physiol., May 1998, pp. 149-155, vol. 175, No. 2.
Jackson et al., "Glucose Infusions Increase Plasma Levels of Amyloid Proteins in High Density Lipoproteins," Biomedicine, 1980, pp. 245, vol. 33.
Jurgens, G. et al., Investigation into the Interaction of Recombinant Human Serum Albumin with Re-lipopolysaccharide and Lipid A., J. Endotoxin, Res., 8, 115-126 (2002).
Kaganovich et al., Editorial in Cell, Misfolded Proteins Have a Parting of Ways, Nature, 2008, pp. 1088-1095, vol. 454.
Kawahara et al., Aluminum promotes the aggregation of Alzheimer's amyloid bet protein in vitro, Biochemical and Biophysical Research Communications, Jan. 28, 1994, pp. 531-535, vol. 198, No. 2.
Kayed, R. et al., Common Structure of Soluble Amyloid Oligomers Implies Common Mechanism of Pathogenesis, Science, 300, 486-489 (2003) with Supporting Online Materials.
Keck et al., Proteasome inhibition by paired helical filament-tau in brains of patients with Alzheimer's disease, Journal of Neurochemistry, 2003, pp. 115-122, vol. 85.
Khoury et al., Microglia, Scavenger Receptors, and the Pathogenesis of Alzheimer's Disease, Neurobiology of Aging, 1998.
Kim et al., Molecular Packing of Lysozyme, Fibrinogen, and Bovine Serum Albumin on Hydrophilic and Hydrophobic Surfaces Studies by Infrared-Visible Sum Frequency Generation and Fluorescence Microscopy, J. Am. Chem. Soc., Articles, published on Web Feb. 12, 2003, pp. 3150-3158, vol. 125.
Kim et al., Thermodynamic beta-sheet propensities measured using a zinc-finger host peptide, Nature, 1993, pp. 267-270, vol. 362.
Kim Tae Yoon et al., Both E7 and CpG-oligodeoxynucleotide are required for protective immunity against challenge with human papillomavirus 16 (E6/E7) immortalized tumor cells: Involvement of CD4+ and CD8+ T cells in protection, Cancer Research, Dec. 15, 2002, pp. 7234-7240, vol. 62, No. 24.

Korol et al., "Glucose, memory, and aging," Am. J. Clin. Nutr., 1998, pp. 764S-771S, vol. 67 (Suppl.).
Kost et al., Limited plasmin proteolysis of vitronectin. Characterization of the adhesion protein as morpho-regulatory and angiostatin-binding factor, European Journal of Biochemistry, Mar. 1, 1996, pp. 682-688, vol. 236, No. 2.
Kranenburg et al., "Tissue-Type Plasminogen Activator is a Multigland Cross-Beta Structure Receptor," Current Biology, Oct. 29, 2002, pp. 1833-1839, vol. 12.
Kranenburg et al., Recombinant endostatin forms amyloid fibrils that bind and are cytotoxic to murine neuroblastoma cells in vitro, FEBS Letters, 2003, pp. 149-155.
Kuiper et al., Abstract, Clinical research on antiangiogenic therapy, Pharmacol Res., 1998, pp. 1-16, vol. 37, No. 1.
Landman, W.J., Amyloid Anthropathy in Chickens, Vet. Q., 21, 78-82 (1999).
Levine et al. Induction of Anti Phospholipid Autoantibodies by Beta2-Glycoprotein I Bound to Apoptotic Thymocytes, J. Autoimmun., 11, 413-424 (1998).
Levine III, et al., Screening for pharmacologic inhibitors of amyloid fibril formation, Methods Enzymol., 1999, pp. 467-476, vol. 309.
Liu, Y. et al., LPS receptor (CD14): a Receptor for Phagocytosis of Alzheimer's Amyloid Peptide. Brain, (2005).
Lodish et al., Molecular Cell biology, 4th Edition, 2000, W.H. Freeman & Co., Figure 22.
Lowe et al., Journal of Molecular Recognition, 1998, pp. 194-199, vol. 11.
Lu Xiuhua et al., A mouse model for the evaluation of pathogenesis and immunity to influenza A (H5N1) viruses isolated from humans, Journal of Virology, Jul. 1999, pp. 5903-5911, vol. 73, No. 7, The American Society for Microbiology, US.
Luijkx, et al., Relative Immunogenicity of PorA Subtypes in a Multivalent Neisseria meningitidis Vaccine Is Not Dependent on Presentation Form, Infect Immun., 71, 6367-6371 (2003).
Lutters, et al. Dimers of Beta 2-Glycoprotein I Mimic the in Vitro Effects of Beta 2-Glycoprotein I-Anti-Beta 2-Glycoprotein I Antibody Complexes., J. Biol. Chem., 276, 3060-3067 (2001).
Maas et al., Editorial in Cell, Aggregates Set Off Factor XII, J. Clin. Invest., 2008, pp. 3208-3218, vol. 118.
Maas et al., Misfolded proteins activate Factor XII in humans, leading to kallikrein formation without initiating coagulation, Research article, The Journal of Clinical Investigation, Sep. 2008, pp. 3208-3218, vol. 118, No. 9.
Maas et al., Identification of fibronectin type I domains as amyloid-binding modules on tissue-type plasminogen activator and three homologs, Amyloid, Sep. 2008, pp. 166-180, vol. 15, No. 3.
Machovich et al., Denatured Proteins as Cofactors for Plasminogen Activation, Archives of Biochemistry and Biophysics, Aug. 15, 1997, pp. 343-349, vol. 344, No. 2.
Machovich et al., Myosin as cofactor and substrate in fibrinolysis, FEBS Letters, 1997, pp. 93-96, vol. 407, No. 1.
Mackay et al., Protein interactions: is seeing believing?, Trends in Biochemical Sciences, 2007, pp. 530-531, vol. 32, No. 12.
Maesaki et al., The structural basis of rho effector recognition revealed by the crystal structure of human rhoA complexed with the effector domain of PKN/PRK1, Mol. Cell., 1999, pp, 793-803, vol. 4.
Maggio et al., "Brain Amyloid—A Physicochemical Perspective," Brain Pathology, 1996, pp. 147-162, vol. 6.
Mahdavi et al., Vaccines Against Human Papillomavirus and Cervical Cancer: Promises and Challenges, The Oncologist, 2005, pp. 528-538, vol. 10.
Mandriota, et al., Vascular endothelial growth factor-induced in vitro angiogenesis and plasminogen activator expression are dependent on endogenous basic fibroblast growth factor, J. Cell Sci., 1997, pp. 2293-2302, vol. 110.
Marciani, Vaccine adjuvants: Role and mechanisms of action in vaccine immunogenicity, Drug Discovery Today, Oct. 15, 2003, pp. 934-943, vol. 8, No. 20.
Marks et al., Infective Endocarditis Successfully Treated to Extremely Low Birth Weight Infants With Recombinant Tissue Plasminogen Activator, Pediatrics, Jan. 2002, pp. 153-158, vol. 109, No. 1.
Marsh et al., The Structure of Tussah Silk Fibroin, World Scientific Series in 20th Century Chemistry—vol. 10, Selected Scientific Papers, pp. 1078-1083, vol. II—Biomolecular Sciences, reprinted from Acta Crystallographica, Nov. 1955, vol. 8, Part II.
Matsuura et al., Anticardiolipin Antibodies Recognize Beta 2-Glycoprotein I Structure Altered by Interacting with an Oxygen Modified Solid Phase Surface, J. Exp. Med., 179, 457-462 (1994).
Matzinger, P, An Innate Sense of Danger, Ann. N Y. Acad. Sci., 961, 341-342 (2002).
Minor et al., Context is a major determinant of beta-sheet propensity, Nature, 1994, pp. 264-267, vol. 371.
Morrison, et al., Direct Evidence for Hageman Factor (Factor XII) Activation by Bacterial Lipopolysaccharides (Endotoxins), J. Exp. Med., 140, 797-811 (1974).
Mueller et al., Editorial in Cell, Unruly Glycoproteins Are Discharged from the ER by SEL1L and Partners, Proc. Natl. Acad. Sci, 2008, pp. 12325-12330, vol. 105.
Munro et al., Consequences of the Non-specific Binding of a Protein to a Linear Polymer: Reconciliation of Stoichiometric and Equilibrium Titration Data for the Thrombin-Heparin Interaction, J. theor. Biol., 2000, pp. 407-418, vol. 203.
Muramatsu et al., In vitro evaluation of the heparin-coated Gyro C1E3 blood pump, Artificial Organs, Jul. 2001, pp. 585-590, vol. 25, No. 7.
Nesheim et al., Abstract, Thrombin, thrombomodulin and TAF1 in the molecular link between coagulation and fibrinolysis, Thromb Haemost. Jul. 1997, pp. 386-391, vol. 78, No. 1.
Nguyen, Tam Luong, Three-dimensional Model of the Pore Form of Anthrax Protective Antigen. Structure and Biological Implications, Journal of Biomolecular Structure & Dynamics, 2004, pp. 253-265, vol, 22, No. 3.
Nieuwenhuizen et al., Identification of a Site in Fibrin(ogen) Which is Involved in the Acceleration of Plasminogen Activation by Tissue-Type Plasminogen Activator, Biochimica et Biopysica Acta, 1983, pp. 86-92, vol. 784.
Nunc (2009, updated) ImmobilizerTM F96 MicroWellTM Plates (2009, updated) http://www.nuncbrand.com/us/page.aspx?ID_10212, p. 1.
O'Reilly et al., Endostatin: An Endogenous Inhibitor of Angiogenesis and Tumor Growth, Cell, Jan. 24, 1997, pp. 277-285.
Ockenhouse et al., Sequestrin, a CD36 recognition protein on Plasmodium falciparum malaria-infected erythrocytes identified by anti-idiotype antibodies, Proc. Natl. Acad. Sci. USA, 1991, pp. 3175-3179, vol. 88.
O'Nuallain et al., Conformational Abs recognizing a generic amyloid fibril epitope, Proceedings of the National Academy of Sciences of USA, Feb. 5, 2002, pp. 1485-1490, vol. 99, No. 3, National Academy of Science, Washington, DC, USA.
Oomen et al., J. Mol. Biol., May 16, 2003, pp. 1083-1089, vol. 328, No. 5.
Orgel et al., The In Situ Supermolecular Structure of Type I Collagen, Structure, Nov. 2001, pp. 1061-1069, vol. 9.
Ossowski et al., Abstract, Antibodies to plasminogen activator inhibit human tumor metastasis, Cell, Dec. 1983, pp. 611-619, vol. 35.
Paris et al., Anti-angiogenic activity of the mutant Dutch Aβ peptide on human brain microvascular endothelial cells, Molecular Brain Research, 2005, pp. 212-230, vol. 136.
Paris et al., Inhibition of angiogenesis by Aβ peptides, Angiogenesis, 2004, pp. 75-85, vol. 7.
Partial European Search Report, EP 02 07 7797, dated Dec. 13, 2002.
Partial European Search Report, EP 05 07 5656, dated Sep. 7, 2005.
PCT International Preliminary Examination Report, PCT/NL01/00155, dated May 10, 2002.
PCT International Search Report, PCT/NL01/00155, dated Sep. 4, 2001.
PCT International Scarch Report, PCT/NL2006/000143, dated Jan. 22, 2007.
PCT International Search Report, PCT/NL2006/000149, dated May 14, 2007.
PCT International Search Report, PCT/NL2006/000361, dated Mar. 29, 2007.
PCT International Search Report, PCT/NL2006/000362, dated Feb. 5, 2007.

PCT International Search Report, PCT/NL2006/000363, dated Dec. 21, 2006.
PCT International Search Report, PCT/NL2006/000364, dated Mar. 28, 2007.
PCT International Search Report, PCT/NL2006/000365, dated Jan. 12, 2007.
Pepys, M. B., "Pathogenesis, diagnosis and treatment of systemic amyloidosis," Philosophical Transactions of the Royal Society of London B Biological, 2001, pp. 203-211, vol. 356, No. 1406.
Poland, G.A., Vaccines against Avian Influenza—A Race against Time, N Engl J Med., 354, 1411-1413 (2006).
Radcliffe et al., A Critical Role of Lysine Residues in the Stimulation of Tissue Plasminogen Activator by Denatured Proteins and Fibrin Clots, Biochimica et Biopysica Acta, 1983, pp. 422-430, vol. 743.
Redlined Set of Claims submitted in European copending case (EP Application No. 01912573.1), Dec. 28, 2007.
Reijerkerk et al., European Journal of Cancer, 2000, pp. 1695-1705, vol. 36.
Reinbold, J., "Akuttherapie der diabetischen Notfalle," Notfallmedizin, 2002, pp. 82-84, vol. 28.
Reixach et al., Inhibition of beta-amyloid-induced neurotoxicity by imidazopyridoindoles derived from a synthetic combinatorial library, J. Struct. Biol. 2000, pp. 247-258, vol. 130.
Renard et al., Catheter Complications Associated with Implantable Systems for Peritoneal Insulin Delivery, Diabetes Care, Mar. 1995, pp. 300-306, vol. 18, No. 3.
Rochet et al., Amyloid fibrillogenesis: themes and variations, Current Opinion in Structural Biology, 2000, pp. 60-68.
Roth et al., Abstract, Differential Engagement of Platelet CD36 in Fibrin Clot Retraction Versus Aggregation, Blood and 45th Annual Meeting of the American Society of Hematology, Nov. 16, 2003, pp. 62b, vol. 102, No. 11.
Ruf et al., Abstract, Tissue factor in cancer angiogenesis and metastasis, Curr Opin Hematol., 1996, pp. 379-384, vol. 3, No. 5.
Sara et al., Crystalline Bacterial Cell Surface Layers (S-Layers) front Cell Structure to Biomimetics, Prog. Biophys. Molec. Biol., 1996, pp. 83-111, vol. 65.
Schmaier et al., The Elusive Physiologic Role of Factor XII, The Journal of Clinical Investigation, Sep. 2008, pp. 3006-3009, vol. 118, No. 9.
Schmidt et al., The biology of the receptor for advanced glycation end products and its ligands, Biochimica et Biophysica Acta, 2000, pp. 99-111, vol. 1498.
Sipe et al., Review: History of the Amyloid Fibril, Journal of Structural Biology, 2000, pp. 88-98.
Sousa et al., Familial Amyloid Polyneuropathy: Receptor for Advanced Glycation End Products—Dependent Triggering of Neuronal Inflammatory and Apoptotic Pathways, The Journal of Neuroscience, Oct. 1, 2001, 7576-7586, vol. 21, No. 19.
Sparknotes (2008, updated), Amino Acids and proteins, <http://www.sparknotes.com/health/aminoacids/section1.html>, pp. 1-7.
Speidel et al., Priming of Cytotoxic T Lymphocytes by Five Heatag-gregated Antigens in Vivo: conditions, Efficiency, and Relation to Antibody Responses, European Journal of Immunology, /Sep. 1997, pp. 2391-2399, vol. 27, No. 9.
Stack et al., Abstract, Regulation of phasminogen activation by components of the extracellular matrix Biochemistry, May 22, 1990, pp. 4966-4970, vol. 29, No. 20.
Steele et al., Editorial in Cell, HSF1 Provides Protection from PrP, Proc. Natl. Acad. Sci., 2008, pp. 13626-13631, vol. 105.
Subang, R. et al., Phospholipid-Bound Beta2-GLycoprotein I Induces the Production of Anti-Phospholipid Antibodies, J. Autoimmun., 15, 21-32 (2000).
Sunde et al., "Common Core Structure of Amyloid Fibrils by Synchrotron X-ray Diffraction," J. Mol. Biol., 1997, pp. 729-739, vol. 273.
Takada et al., Detoxification of Lipopolysaccharide (LPS) by Egg White Lysozyme, FEMS Immunol. Med. Microbiol., 9, 255-263 (1994).
Tang et al., Anti-inflammatory properties of triblock siloxane copolymer-blended materials, Biomaterials, 1999, pp. 1365-1370, vol. 20, No. 15.
Testa et al, "The Effect of Different Glucose Endovenous Administrations on Amylin and Insulin Blood Concentration in Healthy Subjects," J. Biol. Res.—Boll. Soc. It. Biol. Sper., 1996, pp. 103-108, vol. 72, No. 3-4.
Torrent et al., Insights into alternative prion protein topologies induced under high hydrostatic pressure, J. Phys., Condense. Matter., 2004, pp. S1059-S1065, vol. 16, Issue 14.
Treanor et al., Dose-Related Safety and Immunogenicity of a Trivalent Baculovirus-Expressed Influenza-Virus Hemagglutinin Vaccine in Elderly Adults, J Infect Dis., 193, 1223-1228 (2006).
Treanor et al., Safety and Immunogenicity of an Inactivated Subvirion Influenza A (H5N1) Vaccine, N Engl J Med., 354, 1343-1351 (2006).
Tumpey et al., Mucosal delivery of inactivated influenza vaccine inducts B-cell-dependent heterosubtypic cross-protection against lethal influenza A H5N1 virus infection, Journal of Virology, Jun. 2001, pp. 5141-5150, vol. 75, No. 11, The American Society for Microbiology, US.
Turn (biochemistry) (2009), available at http://en.wikipedia.org/wiki/Beta-turn (last modified on Jul. 21, 2009).
UniProtKB/Swiss-Prot entry 097507, <http://www.expasy.org/cgi-bin/niceprot.pl/printable?ac=O97507>, Apr. 6, 2006 visited Feb. 25, 2008.
UniProtKB/Swiss-Prot entry P00748, <http://www.expasy.org/cgi-bin/niceprot.pl/printable?ac=p00748>, Jul. 21, 1986 visited Feb. 25, 2008.
UniProtKB/Swiss-Prot entry P98140, <http://www.expasy.org/cgi-bin/niceprot.pl/printable?ac=P98140>, Feb. 1, 1996 visited Feb. 25, 2008.
UniProtKB/Swiss-Prot entry Q04962, <http://www.expasy.org/egi-bin/niceprot.pl/printable?ac=Q04962>, Feb. 1, 1996 visited Feb. 25, 2008.
UniProtKB/Swiss-Prot entry Q5M879, <http://www.uniprot.org/uniprot/Q5M8979>, Feb. 1, 2005 visited May 15, 2009.
UniProtKB/Swiss-Prot enny Q6PER0, <http://www.expasy.org/cgi-bin/niceprot.pl/printable?ac= Q6PER0>, Jul. 5, 2007 visited Feb. 25, 2008.
Van Beusekom et al., Abstract, Fibrin and basement membrane components, as a biocompatible and thromboresistant coating for metal stents, European Heart Journal, pp. 378, vol. 15.
Van Rijn et al., Classical Swine Fever Virus (CSFV) Envelope Glycoprotein E2 Containing One Structural Antigenic Unit Protects Pigs from Lethal CSFV Challenge, J Gen Virol., 77, 2737-2745 (1996).
Vartio et al., Monoclonal antibody against the N-terminal end of human plasma fibronectin, Biochem. J., 1983, pp. 147-151, vol. 215.
Vaughn et al., The establishment of two cell lines from the insect Spodoptera frugiperda (Lepidoptera; Noctuidae). In Vitro, 13, 211-217, (1977).
Verheijen et al., EMBO 1986, vol. 5, pp. 3525-3530.
Voest, E.E., Abstract, Inhibitors of angiogenesis in a clinical perspective, Anticancer Drugs, Sep. 1996, pp. 723-727, vol. 7, No. 7.
Voropai et al. Spectral properties of thioflavin T and its complexes with amyloid fibrils, J. Appl. Spectrosc., 2003, pp. 868-874, vol. 70.
Wallberg et al., Vaccination with myelin oligodendrocyte glycoprotein adsorbed to alum effectively protects DBA/1 mice from experimental autoimmune encephalomyelitis, European Journal of Immunology, Jun. 2003, pp. 1539-1547, vol. 33, No. 6.
Walsh et al., Amyloid beta-protein fibrillogenesis, J. Biol. Chem., 1999, pp. 25945-25952, vol. 274.
Wang et al., A Study of the Mechanism of Inhibition of Fibrinolysis by Activated thrombin-activable Fibrinolysis Inhibitor, The Journal of Biological Chemistry, Oct. 16, 1996, pp. 27176-27181, vol. 273, No. 42.
Wasterlain et al., "Status Epilepticus in Immature Rats," Arch Neurol, Dec. 1976, pp. 821-827, vol. 33.
Welters et al., Chemically synthesized protein as tumour-specitic vaccine: immunogenicity and efficacy of synthetic HPV16 E7 in the TC-1 mouse tumour model, Dec. 2, 2004, pp. 305-311, vol. 23, No. 3.
Wensvoort et al., Antigenic Differentiation of Pestivirus Strains with Monoclonal Antibodies Against Hog Cholera Virus, Vet Microbiol., 21, 9-20 (1989).

Wensvoort et al., Production of Monoclonal Antibodies Against Swine Fever Virus and Their Use in Laboratory Diagnosis, Vet Microbipl., 12, 101-108 (1986).
Yakovlev et al., Biochemistry, 2000, pp. 15730-15741, vol. 39.
Yan et al., Cellular cofactors potentiating induction of stress and cytotoxicity by amyloid β-peptide, Biochimica et Biophysica Acta, 2000, pp. 145-157, vol. 1502.
Yan et al., Receptor-dependent cell stress and amyloid accumulation in systemic amyloidosis, Nature Medicine, Jun. 2000, pp. 643-651, vol. 6, No. 6.
Yutani et al., "The Process of Amyloid-like Fibril Formation by Methionine Aminopeptidase from a Hyperthermophile, Pyrococcus furiosus," Biochemistry, 2000, pp. 2769-2777, vol. 39.
Zhang et al., The anatomy of protein beta-sheet topology, J. Mol. Biol., 2000, pp. 1075-1089, vol. 299.
Zucker et al., Abstract, Vascular endothelial growth factor induces tissue factor and matrix metalloproteinase production in endothelial cells: conversion of prothrombin to thrombin results in progelatinase A activation and cell proliferation, Int J. Cancer, Mar. 2, 1998, p. 780-786, vol. 75, No. 5.
Office Action for U.S. Appl. No. 11/033,105 dated May 3, 2007.
Office Action for U.S. Appl. No. 11/033,105 dated Nov. 21, 2007.
Office Action for U.S. Appl. No. 11/033,105 dated Aug. 25, 2008.
Office Action for U.S. Appl. No. 11/033,105 dated May 22, 2009.
Office Action for U.S. Appl. No. 11/384,169 dated Oct. 28, 2008.
Office Action for U.S. Appl. No. 11/384,169 dated Jun. 10, 2009.
Office Action for U.S. Appl. No. 11/087,102 dated Nov. 23, 2007.
Office Action for U.S. Appl. No. 11/087,102 dated Jul. 23, 2009.
Office Action for U.S. Appl. No. 11/181,012 dated Mar. 22, 2007.
Office Action for U.S. Appl. No. 11/181,012 dated Sep. 25, 2007.
Office Action for U.S. Appl. No. 11/181,012 dated May 30, 2008.
Office Action for U.S. Appl. No. 11/181,012 dated Mar. 20, 2009.
Office Action for U.S. Appl. No. 11/995,308 dated Mar. 24, 2008.
Office Action for U.S. Appl. No. 11/661,537 dated Jun. 11, 2009.
U.S. Appl. No. 12/224,087, filed Feb. 18, 2009, Gebbink et al., Affinity Regions.
U.S. Appl. No. 12/225,291, filed Jan. 7, 2009, Gebbink et al., Methods of Binding of Cross-Beta Structures by Chaperones.
U.S. Appl. No. 12/291,398, filed Nov. 7, 2008, Gebbink et al., Immunogenic Compositions Capable of Activating T-Cells.
U.S. Appl. No. 12/291,369, filed Nov. 7, 2008, Gebbink et al., Improved Immunogenic Compositions.
U.S. Appl. No. 61/216,605, filed May 19, 2009, Smith et al., Modulating Compounds.
U.S. Appl. No. 11/995,497, filed Mar. 19, 2008, Gebbink et al., Cross-Beta Structure Binding Compounds.
Salonen et al., (1985) Plasminogen and tissue-type plasminogen activator bind to immobilized fibronectin, J. Biol. Chem., vol. 260, No. 22, pp. 12302-12307.
Luyk X et al., HPLC and tandem detections to monitor conformational properties of biopharmaceuticals, Journal of Chromatography B. 2005. pp. 45-52, vol. 821.
Vermeer, L. "Uniquie protein structure offers a basis for commercial activity." Conceptuur, Dec. 2004, No. 41 (p. 18 is relevant and has been translated).
Baldwin et al., Stable-isotope-labeled peptides in study of protein aggregation, Methods Enzymol., 1999, pp. 576-591, vol, 309.
Serpell, Louise C., Alzheimer's amyloid fibrils: structure and assembly, Biochimica et Biophysica Acta, 2000, pp. 16-30, vol. 1502.
Baumketner et al., Amyloid beta-protein monomer structure: A computational and experimental study, Protein Science, 2006, pp. 420-428, vol. 15.
Ott et al., Enhancement of humoral response against human influenza vaccine with the simple submicron oil/water emulsion adjuvant MF59, Vaccine, 1995, pp. 1557-1562, vol. 13, No. 16.
Tollis et al., Abstract, Recent Development in Avian Influenza Research: Epidemiology and Immuno prophylaxis, Veterinary Journal, 2002, pp. 202-215, vol. 164.
Office Action for U.S. Appl. No. 11/033,105 dated Dec. 22, 2009.
Office Action for U.S. Appl. No. 11/087,102 dated Jul. 6, 2010.
Office Action for U.S. Appl. No. 11/181,012 dated Dec. 28, 2009.
Office Action for U.S. Appl. No. 11/995,308 dated Apr. 3, 2009.
Office Action for U.S. Appl. No. 11/995,308 dated Jan. 8, 2010.
Office Action for U.S. Appl. No. 11/661,537 dated Jan. 26, 2010.
Office Action for U.S. Appl. No. 11/982,161 dated May 28, 2010.
U.S. Appl. No. 11/982,161, filed Oct. 31, 2007, Bouma et al., Cross β Structure Comprising Amyloid Binding Proteins and Methods for Detection of the Cross β Structure for Modulating Cross β Structures Fiber Formation and for Modulating Cross β Structure.
U.S. Appl. No. 11/033,105, filed Jan. 10, 2005, Gebbink et al., Cross β Structure Comprising Amyloid Binding Proteins and Methods for Detection of the Cross β Structure for Modulating Cross β Structures Fiber Formation and for Modulating Cross β Structure.
U.S. Appl. No. 11/886,867, filed Dec. 11, 2007, Gebbink et al., Cross β Structure Comprising Amyloid-Binding Proteins and Methods for Detection of the Cross β Structure for Modulating Cross β Structures Fibril Formation and for Modulating Cross β Structure-Mediated Toxicity and Method for Interfering with Blood Coagulation.
U.S. Appl. No. 11/087,102, filed Mar. 21, 2005, Gebbink et al., Cross β Structure Comprising Amyloid-Binding Proteins and Methods for Detection of the Cross β Structure for Modulating Cross β Structures Fibril Formation and for Modulating Cross β Structure-Mediated Toxicity and Method for Interfering with Blood Coagulation.
U.S. Appl. No. 11/995,481, filed Mar. 25, 2008, Gebbink et al., A Method for Detecting and/or Removing Protein and/or Peptide Comprising a Cross-Beta Structure from an Aqueous Solutions Comprising a Protein.
U.S. Appl. No. 11/995,308, filed Mar. 24, 2008, Gebbink et al., A Method for Detecting and/or Removing a Protein Comprising a Cross-β Structure from a Pharmaceutical Composition.
U.S. Appl. No. 11/661,537, filed Apr. 24, 2007, Gebbink et al., Adjuvation Through Cross-β Structure.
U.S. Appl. No. 11/995,508, filed Mar. 24, 2008, Gebbink et al., Methods for Determining the Effect of a Treatment on the Cross-β Structure Content of a Protein: Selection of Treatments and Uses Thereof.
U.S. Appl. No. 61/216,605, filed May 19, 2009, Bouma et al., Modulating Compounds.
U.S. Appl. No. 12/741,270, Gebbink et al., Enhancement of Immunogenicity of Antigens.
Akiyama, et al; Abstract; Inflammation and Alzheimer's disease; Neurobiol Aging. May-Jun. 2000: 21(3): 383-421.
Bachmann, et al.; Recall Proliferation Potential of Memory CD8 + T Cells and Antiviral Protection; The Journal of Immunology; 2005, 175: 4677-4685.
Boehm et al., Antiangiogenic therapy of experimental cancer does not induce acquired drug resistance, Nature, 1997, pp. 404-407, vol. 390.
Bouma et al., Glycation Induces Formation of Amyloid Cross-beta Structure in Albumin, The Journal of Biological Chemistry, Oct. 24, 2003, vol. 278, No. 43, pp. 41810-41819.
Bouma, B. et al., Adhesion Mechanism of Human Beta(2)-Glycoprotein I to Phospholipids Based on its Crystal Structure, EMBO J., 18, 5166-5174 (1999).
Bronsveld et al., "Use of glucose-insulin-potassium (GIK) in human septic shock," Critical Care Medicine, 1985, pp. 566-570, vol. 13, No. 7.
Chauhan et al., Media from Rhabdomyosarcoma and Neuroblastoma Cell Cultures Stimulate in Vitro Aggregation and Fibrillization of Amyloid Beta-Protein, Neurochemical Research, 1997, pp. 227-232, vol. 22, No. 2.
Coker, et al.; Moleculr chaperone properties of serum amyloid P component; FEBS Letters 473 (2000) 199-202.
De Laat, B., et al., IgG Antibodies That Recognize Epitope G1y40-Arg43 in Domain I of {beta}2-glycoprotein I Cause LAC and Their Presence Correlates Strongly with Thrombosis. Blood, 105, 1540-1545 (2005).
De Laat, et al., Beta2-glycoprotein I-dependent lupus anticoagulant highly correlates with thrombosis in the antiphospholipid syndrome, Blood, 104, 3598-3602 (2004).
Demattos et al., PNAS, 2001, pp. 8850-8855, vol. 98.
Dubois et al., Thrombin binding to GPIbalpha induces integrin alphaIIbbeta3 dependent platelet adhesion to fibrin in ex vivo flowing whole blood, Thrombosis and Haemostasis, Feb. 2004; pp. 233-237, vol. 91, No. 2.

Efferson, et al; Stimulation of Human T Cells by an Influenza A Vector Expressing a CTL Epitope from the HER-2/neu Protooncogene Results in Higher Numbers of Antigen-specific TCR$^{hi}$ Cells than Stimulation with Peptide, Divergent Roles of IL-2 and IL-15; Anitcancer Research 25: 715-724 (2005).
European Patent Office Notification for Application No. 03 762 927.6 dated Oct. 4, 2006.
European Search Report (08 153 132.9) dated Oct. 1, 2009.
European Search Report (EP 1 978 362 A3) dated Oct. 2, 2008.
Gadek, T., Strategies and Methods in the Identification of Antagonists of Protein-Protein Interactions, Structure-Guided Drug Discovery, pp. 21-24.
Genbank Public DNA Database, Accession No. 2B4X_I, Mourey et al., Sep. 27, 2005, pp. 1-3 <http://www.ncbi.nlm.nih.gov...> (visited Jan. 15, 2009).
Genbank Public DNA Database, Accession No. 2B4X_L, Mourey et al., Sep. 27, 2005, pp. 1-3 <http://www.ncbi.nlm.nih.gov...> (visited Jan. 15, 2009).
Hubbard et al., Spontaneous pancreatic islet amyloidosis in 40 baboons, J. Med. Primatol. 2002, pp. 84-90, vol. 31, No. 2.
Jacobsen et al., Enhanced clearance of A beta in brain by sustaining the plasmin proteolysis cascade, PNAS, Jun. 24, 2008, pp. 8754-8759, vol. 105, No. 25.
Marks et al., Infective Endocarditis Successfully Treated in Extremely Low Birth Weight Infants With Recombinant Tissue Plasminogen Activator, Pediatrics. Jan. 2002, pp. 153-158, vol. 109, No. 1.
Nesheim et al., Abstract, Thrombin, thrombomodulin and TAFI in the molecular link between coagulation and fibrinolysis, Thromb Haemost, Jul. 1997, pp. 386-391, vol. 78, No. 1.
Nunc (2009, updated) Immobilizer™ F96 MicroWell™ Plates (2009, updated) http://www.nuncbrand.com/us/page.aspx?ID_10212, p. 1.
Nyhlin et al., Advanced glycation end product in familial amyloidotic polyneuropathy (FAP), Journal of Internal Medicine, 2000, pp. 485-492, vol. 247.
Obrenovich et al., Glycation Stimulated Amyloid Formation, Sci. Aging Knowl. Environm., Jan. 14, 2004, pp. pe3, vol. 2004, No. 2.
Ono. et al.; Radioiodinated Flavones for in Vivo Imaging of β-Amyloid Plaques in the Brain: J. Med. Chem. 2005, 48, 7253-7260.
Paris et al., Ami-angiogenic activity of the mutant Dutch Aβ peptide on human brain microvascular endothelial cells, Molecular Brain Research, 2005, pp. 212-230, vol. 136.
PCT International Search Report, PCT/NL2006/000143, dated Jan. 22, 2007.
Rao et al., Thermo and pH stable ATP-independent chaperone activity of heat-inducible Hsp70 from Pennisetum glaucum, Plant. Signal Behav., 2010, pp. 110-121, vol. 5, No. 2.
Reijerkerk et al., "No grip, no growth: the conceptual basis of excessive proteolysis in the treatment of cancer," European Journal of Cancer, 2000, pp. 1695-1705, vol. 36.
Roth et al., Differential Engagement of Platelet CD36 in Fibrin clot retraction versus aggregation, Blood, Nov. 2003, 45$^{th}$ Annual Meeting of the American Society of Hematology, vol. 102, No. 11, San Diego, CA, USA.
Sara et al., Crystalline Bacterial Cell Surface Layers (S-Layers) from Cell Structure to Biomimetics. Prog. Biophys., Molec. Biol., 1996, pp. 83-111, vol. 65.
Steele et al., Editorial in Cell, HSFI Provides Protection from PrP, Proc. Natl. Acad. Sci., 2008, pp. 13626-13631, vol. 105.
Subang. R. et al., Phospholipid-Bound Beta2-GLycoprotein I Induces the Production of Anti-Phospholipid Antibodies, J. Autoimmun., 15, 21-32 (2000).
Tucker et al., Journal of Neuroscience, 2000, p. 3937-46, vol. 20.
Tumpey et al., Mucosal delivery of inactivated influenza vaccine induces B-cell-dependent heterosubtypic cross-protection against lethal influenza A H5N1 virus infection, Journal of Virology, Jun. 2001, pp. 5141-5150, vol. 75, No. 11, The American Society for Microbiology, US.
UniProtKB/Swiss-Prot entry Q6PER0, <http://www.expasy.org/cgi-bin/niceprot.pl/printable?ac= Q6PER0>, Jul. 5, 2007 visited Feb. 25, 2008.
Verheijen et al., "Involvement of finger domain and kringle 2 domain of tissue-type plasminogen activator in fibrin binding and stimulation of activity by fibrin," EMBO 1986, vol. 5, pp. 3525-3530.
Welters et al., Chemically synthesized protein as tumour-specific vaccine: immunogenicity and efficacy of synthetic HPV16 E7 in the TC-1 mouse tumour model, Dec. 2, 2004, pp. 305-311, vol. 23, No. 3.
Wheeler, C.M.; Abstract; Preventive vaccines for cervical cancer; Salud p'ublica de M'exico. (Jul.-Aug. 1997).
"Pharmaceutical", Online Dictionary, <http://dictionaryreference.com/browse/pharmaceutical> visited Dec. 15, 2008.
Cardoso, e al. Aprotinin binding to amyloid fibrils; Eur. J. Biochem, 267, 23072311 (2000).
Kranenburg, et al. Tissue-Type Plasminogen Activator Is a Multiligand Crossβ Structure Receptor; Current Biology, vol. 12, 1833-1839, Oct. 29, 2002.
PCT Exam Report 06/769 395.2 dated Jun. 15, 2011.
Database WPI, Thomas Scientific, London, GB: AN 1985174924; XP 002631339 & JP 60 103964; Unitika Ltd; Jun. 8, 1985.
European Search Report for Application No. 11153594.4-1223 dated Jun. 8, 2011.
European Search Report; EP 10 18 5187 dated Aug. 29, 2011.
Kataoka, et al; Hepatocyte Growth Factor Activator Inhibitor Type I Is a Specific Cell Surface Binding Protein of Hepatocyte Growth Factor Activator (HGFA) and Regulates HGFA Activity in the Pericellular Microenvironment; The Journal of Biological Chemistry; vol. 275, No. 51, Dec. 22, 2000; pp. 40453-40462.
Kisilevsky, et al. Characterization of Fibronectin Binding to Alzheimer's Beta Amyloid Precursor Proteins, Third International Conference on Alzheimer's Disease;S81-S82, (1992).
Yasuhara, et al. Hageman factor and its binding sites are present in senile plaques of Alzheimer's disease, Brain Research 654 (1994) 234-240.
Lopez Garcia et al., NMB structure of the bovine prion protein, PNAS, Jul. 18, 2000, pp. 8334-8339, vol. 97, No. 15.
Hinson et al., Pathogenic potential of IgG binding to water channel extracellular domain in neuromyelitis optica, Neurology, vol. 69, No. 24, pp. 2221-2231;2007.
Johnstone et al., Monoclonal antibodies that recognize the native human thyrotropin receptor, Mol. Cell, Endocrinol., vol. 105, No. 2, pp. R1-R9; 1994.

* cited by examiner

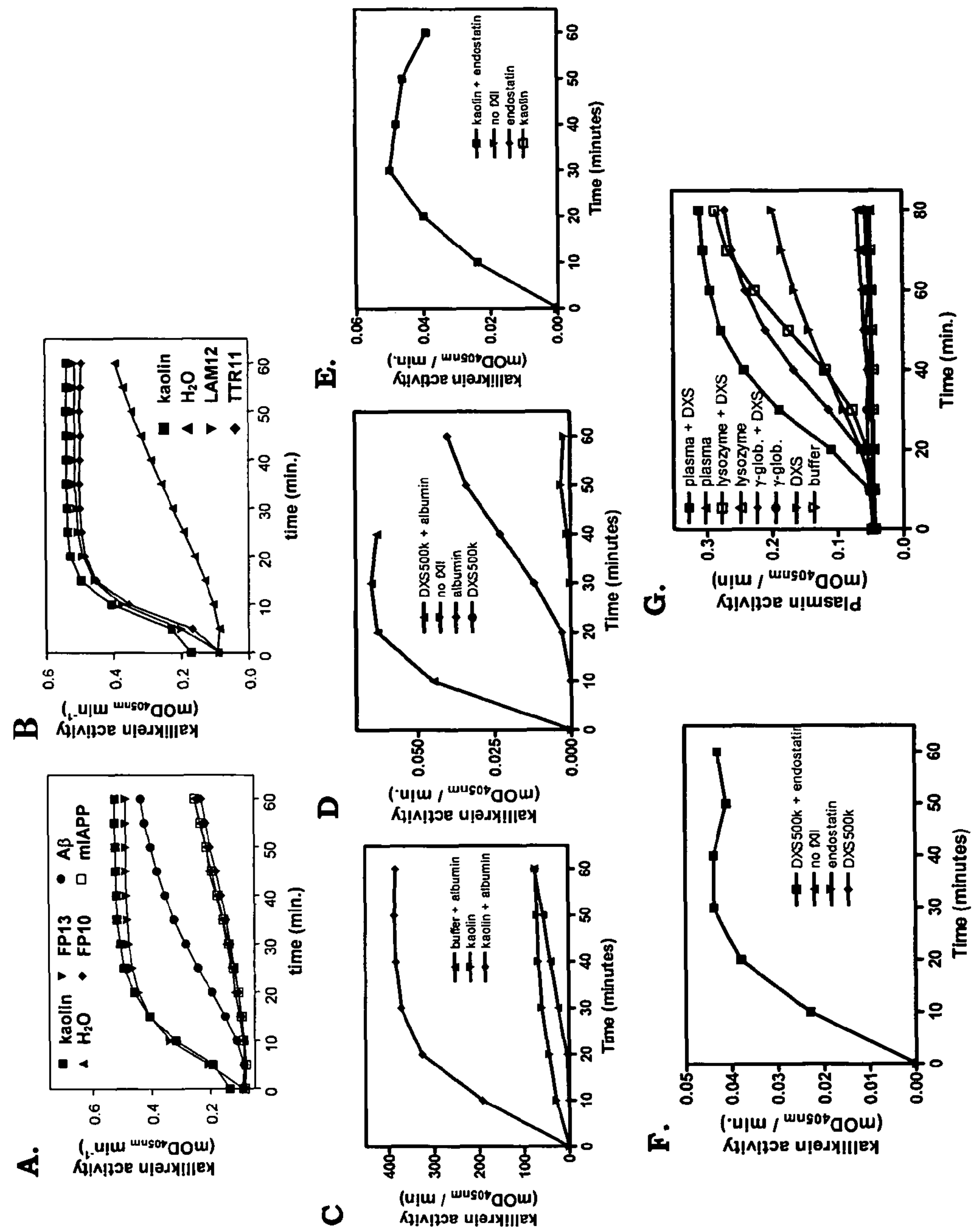
Figure 2
A.
kaolin
FP13
Aβ
H2O
FP10
mIAPP
kallikrein activity (mOD405nm min-1)
time (min.)
B
kaolin
H2O
LAM12
TTR11
kallikrein activity (mOD405nm min-1)
time (min.)
C
buffer + albumin
kaolin
kaolin + albumin
kallikrein activity (mOD405nm / min)
Time (minutes)
D
DXS500k + albumin
no fXII
albumin
DXS500k
kallikrein activity (mOD405nm / min.)
Time (minutes)
E.
kaolin + endostatin
no fXII
endostatin
kaolin
kallikrein activity (mOD405nm / min.)
Time (minutes)
F.
DXS500k + endostatin
no fXII
endostatin
DXS500k
kallikrein activity (mOD405nm / min.)
Time (minutes)
G.
plasma + DXS
plasma
lysozyme + DXS
lysozyme
γ-glob. + DXS
γ-glob.
DXS
buffer
Plasmin activity (mOD405nm / min)
Time (min.)

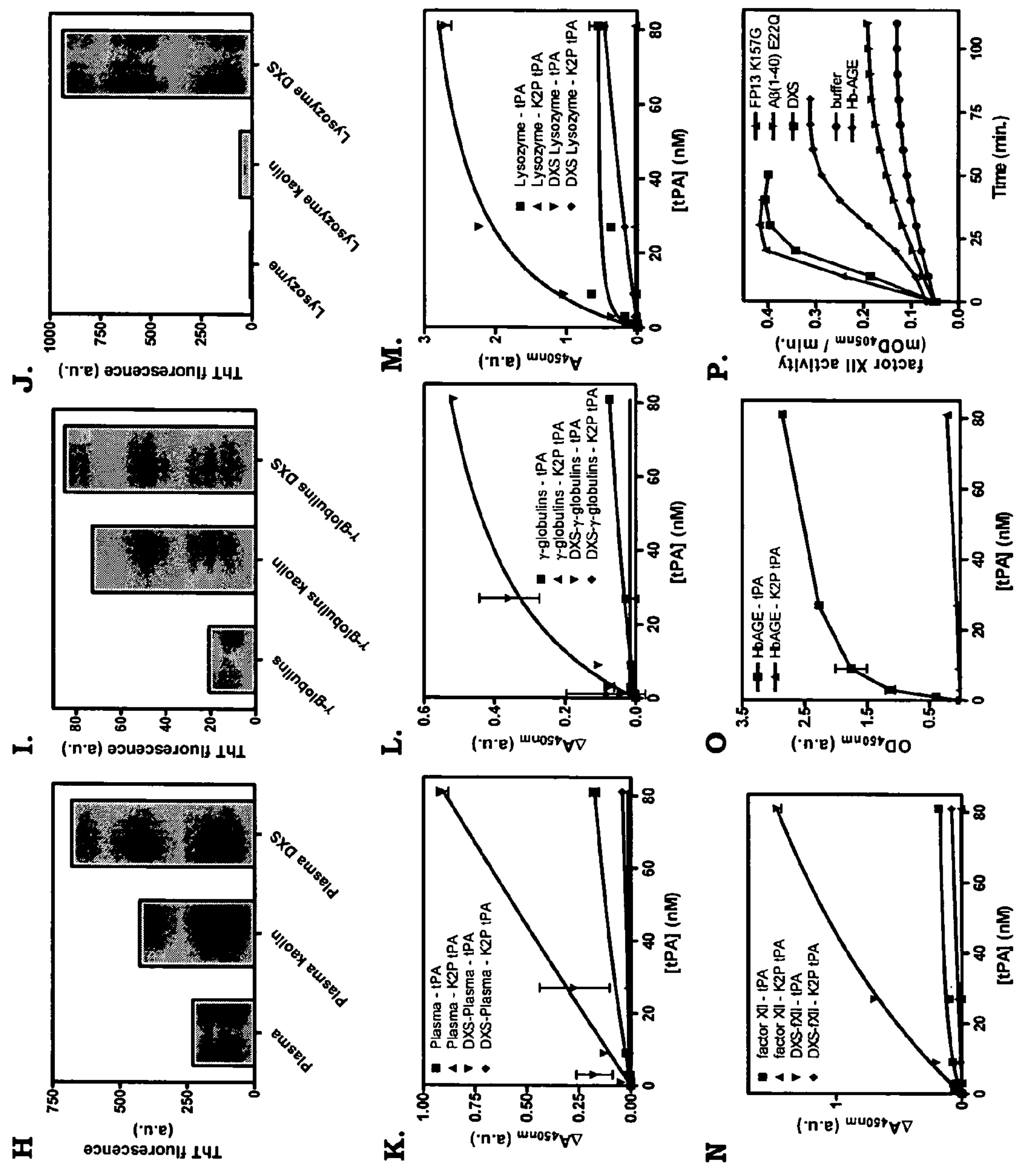

Figure 2 (continued)
H
ThT fluorescence (a.u.)
Plasma
Plasma kaolin
Plasma DXS
I.
ThT fluorescence (a.u.)
γ-globulins
γ-globulins kaolin
γ-globulins DXS
J.
ThT fluorescence (a.u.)
Lysozyme
Lysozyme kaolin
Lysozyme DXS
K.
ΔA450nm (a.u.)
Plasma - tPA
Plasma - K2P tPA
DXS-Plasma - tPA
DXS-Plasma - K2P tPA
[tPA] (nM)
L.
ΔA450nm (a.u.)
γ-globulins - tPA
γ-globulins - K2P tPA
DXS-γ-globulins - tPA
DXS-γ-globulins - K2P tPA
[tPA] (nM)
M.
A450nm (a.u.)
Lysozyme - tPA
Lysozyme - K2P tPA
DXS Lysozyme - tPA
DXS Lysozyme - K2P tPA
[tPA] (nM)
N
ΔA450nm (a.u.)
factor XII - tPA
factor XII - K2P tPA
DXS-fXII - tPA
DXS-fXII - K2P tPA
[tPA] (nM)
O
OD450nm (a.u.)
HbAGE - tPA
HbAGE - K2P tPA
[tPA] (nM)
P.
factor XII activity (mOD405nm / min.)
FP13 K157G
Aβ(1-40) E22Q
DXS
buffer
Hb-AGE
Time (min.)

Figure 3
A.
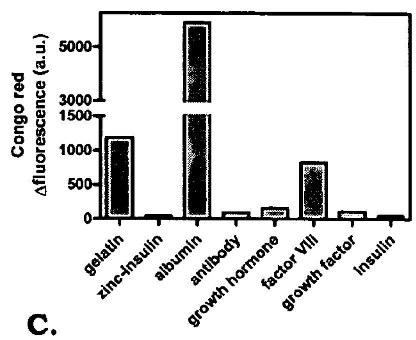
B.
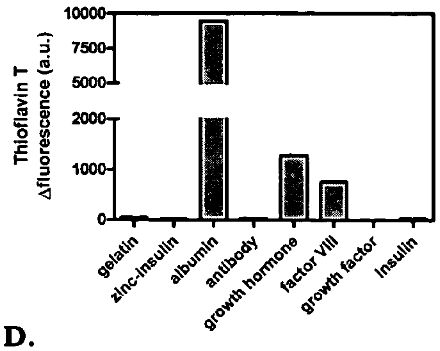
C.
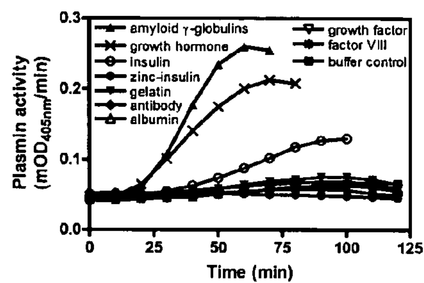
D.
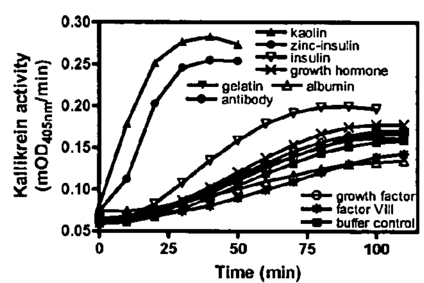
E.
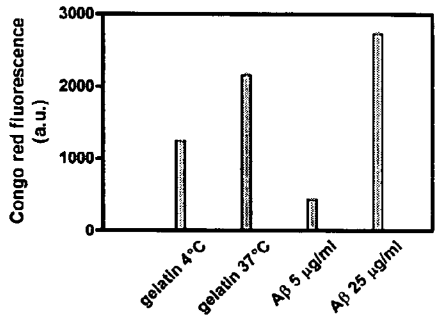
F.
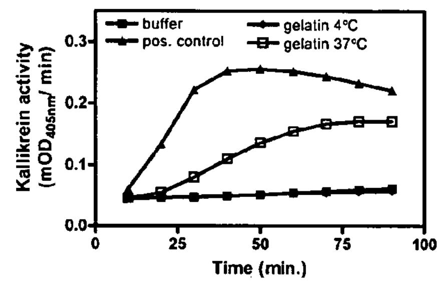
G.
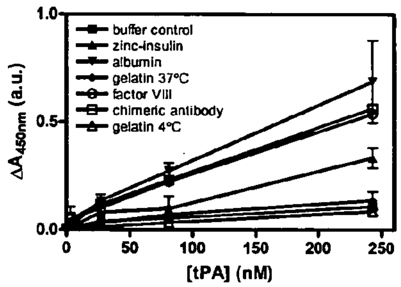
H.
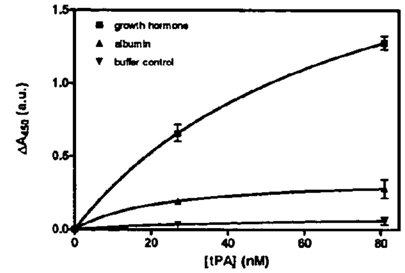
I.
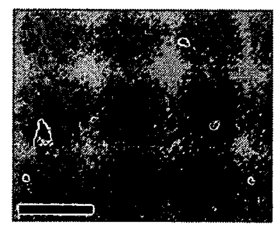
J.
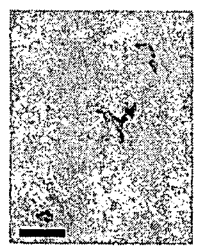
K.

FIGURE 5
A.
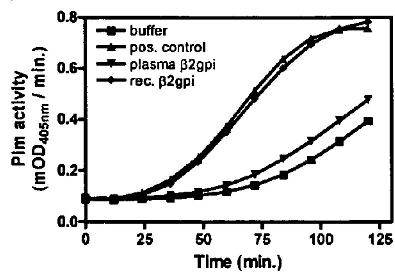
B.
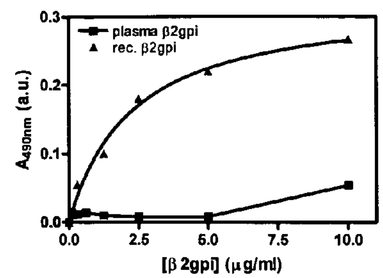
C.
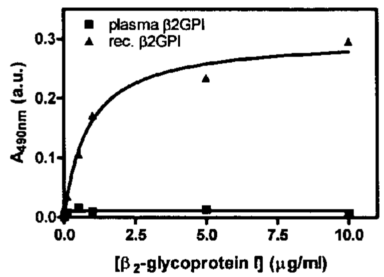
D
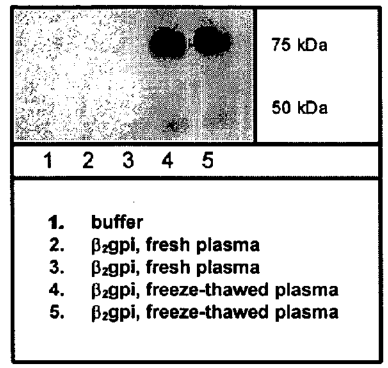
E.
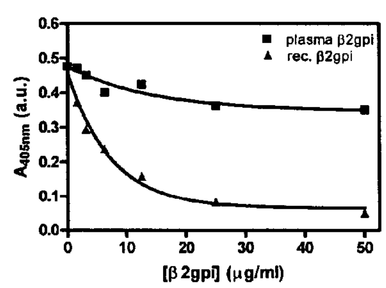
F.
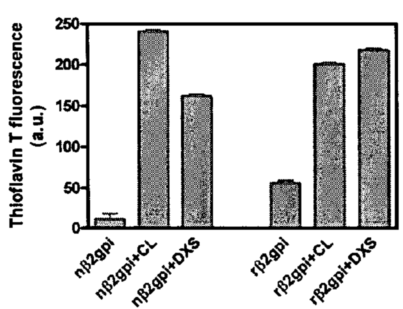
G
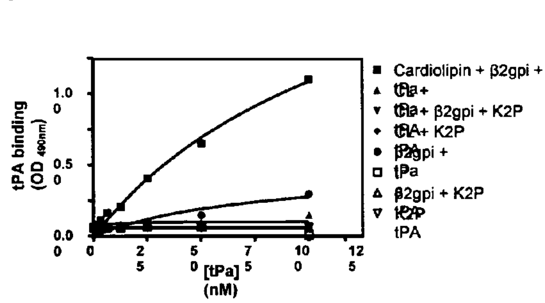
H.
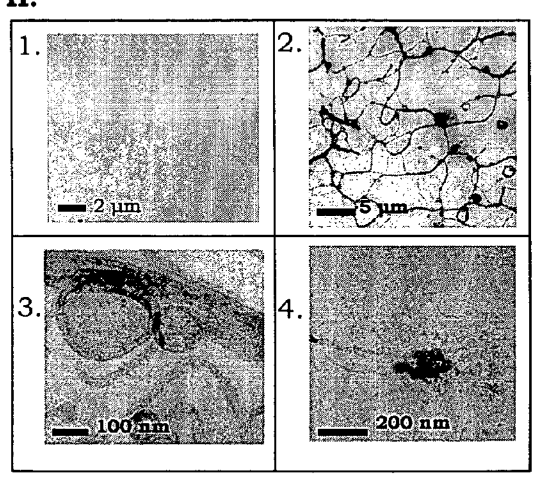

SEQUENCE LISTING

```
<160> NUMBER OF SEQ ID NOS: 5

<210> SEQ ID NO 1
<211> LENGTH: 13
<212> TYPE: PRT
<213> ORGANISM: Artificial
<220> FEATURE:
<223> OTHER INFORMATION: Human fibrin alpha-chain (148-160) amyloid
      fragment with Lys157Gly mutation

<400> SEQUENCE: 1

Lys Arg Leu Glu Val Asp Ile Asp Ile Gly Ile Arg Ser
1               5                   10


<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Gln Asp Val Gly Ser Asn Lys Gly Ala Ile Ile
```

-continued

```
          20                  25                  30

Gly Leu Met Val Gly Gly Val Val
        35                  40


<210> SEQ ID NO 3
<211> LENGTH: 10
<212> TYPE: PRT
<213> ORGANISM: Homo sapiens

<400> SEQUENCE: 3

Lys Arg Leu Glu Val Asp Ile Asp Ile Lys
1               5                   10


<210> SEQ ID NO 4
<211> LENGTH: 28
<212> TYPE: DNA
<213> ORGANISM: Artificial
<220> FEATURE:
<223> OTHER INFORMATION: Forward primer with BglII site

<400> SEQUENCE: 4

gagatctgct caaaacatca cagcccgg                                        28


<210> SEQ ID NO 5
<211> LENGTH: 28
<212> TYPE: DNA
<213> ORGANISM: Artificial
<220> FEATURE:
<223> OTHER INFORMATION: Reverse primer with NotI site

<400> SEQUENCE: 5

gcggccgcct cgcctggttc gatgatgc                                        28
```

METHOD FOR DETECTING AND/OR REMOVING A PROTEIN COMPRISING A CROSS-BETA STRUCTURE FROM A PHARMACEUTICAL COMPOSITION

TECHNICAL FIELD

The invention relates to the field of biotechnology generally, and, more particularly to compositions comprising a protein, more specifically to pharmaceutical compositions. More specifically, the invention relates to the detection and/or removal of conformationally altered proteins and/or molecules comprising a cross-β structure from a pharmaceutical composition or any of its constituents comprising a protein.

BACKGROUND

Pharmaceutical compositions are in general suitable for administration to a subject, the subject being an animal or a human. Many pharmaceutical compositions are available that are either manufactured or purified by processes in which proteins or peptides are involved, or are based on protein and/or polypeptide and/or peptide or amino-acid compositions, including compositions with amino-acid derivatives. Important categories of nowadays pharmaceutical compositions comprising a protein or a proteinaceous compound as an active substance include, but are not limited to hormones, enzymes, vaccines and antigens, cytokines and antibodies. In addition to the above-mentioned proteinaceous pharmaceutical compositions, a large number of pharmaceutical compositions are manufactured with the help of a production and/or purification step comprising proteins. For example, many pharmaceutical compositions comprise one or more proteins as a stabilizing agent.

Safety aspects are of great concern with any pharmaceutical composition. Drug stability during production and storage, and after administering to the body, attracts much effort during development of new active compounds, and thereafter. Market withdrawals of initially successful pharmaceutical compositions are sometimes necessary because of the occurrence of unforeseen and undesired side effects. For example: plasma, erythropoietin, insulin, antibodies, aprotinin, albumin, thrombopoietin, interferon α, factor VIII, have all caused unwanted side effects after administration in individuals. These examples underline that continuous improvement of the current safety testing methodologies is necessary to reduce the risk for unforeseen, unwanted and/or deleterious side effects after administering pharmaceutical compositions to a human or animal.

Health problems related to the use of pharmaceutical compositions are, for example, related to the fields of hematology, fibrinolysis and immunology. An incomplete list of observed side-effects after administration of pharmaceutical compositions comprises, for example, fever, anaphylactic responses, (auto)immune responses, disturbance of hemostasis, inflammation, fibrinolytic problems, including sepsis and disseminated intravascular coagulation (DIC), which can be fatal. Side effects can be caused by either an alteration of a protein or a proteinaceous compound present in the pharmaceutical composition, or by added diluents or carrier substances of the pharmaceutical composition. A proteinaceous compound in this specification means any compound which comprises a peptide, polypeptide, or protein, and/or altered or degraded forms thereof. Alteration of the proteinaceous compound of a pharmaceutical composition comprises, for example, denaturation, multimerization, proteolysis, acetylation, glycation, oxidation or unfolding of proteins.

SUMMARY OF THE INVENTION

The present invention discloses that the toxic structures are cross-β structures. The present invention further discloses methods and means for detecting cross-β structures in pharmaceutical composition and/or any of its constituents comprising a protein.

In this specification, the terms "cross-β structure conformation" and "cross-β structure" are synonymous and are interchangeably used herein.

A cross-β structure is defined as a part of a protein or peptide, or a part of an assembly of peptides and/or proteins, that comprises an ordered group of β-strands, typically a group of β-strands arranged in a 3-sheet, in particular a group of stacked or layered β-sheets. A typical form of stacked β-sheets is in a fibril-like structure in which the β-sheets may be stacked in either the direction of the axis of the fibril or perpendicular to the direction of the axis of the fibril. The term peptide is intended to include oligopeptides as well as polypeptides, and the term protein includes proteins with and without post-translational modifications, such as glycosylation. It also includes lipoproteins and complexes comprising proteins, such as protein-nucleic acid complexes (RNA and/or DNA), membrane-protein complexes. Different fluorescent light scattering profiles of amyloid dyes, such as, for example, Congo red or Thioflavin T in staining various amyloid-like aggregates indicate that different cross-β structures occur. Cross-β structures are, for example, found in glycated proteins and in fibrils.[1] Such fibrillar aggregates accumulate in various tissue types and are associated with a variety of degenerative diseases. The term "amyloid" is being used to describe fibrillar deposits (or plaques).[2] In literature, an amyloid fibril is preferably defined as an aggregate that is stained by Congo red and/or Thioflavin T, that appears as fibrils under an electron microscope, and that contains an increased amount of β-sheet secondary structure.[2] Additionally, the presence of β-sheet rich structures can be defined with X-ray fiber diffraction techniques and/or Fourier transform infrared spectroscopy. A common denominator of amyloid-like structures is the presence of the cross-β structure structural element. Peptides or proteins with amyloid-like structures are cytotoxic to cells.[3-6] Diseases characterized by amyloid are referred to as conformational diseases or amyloidosis and include, for example, Alzheimer's disease (AD), light-chain amyloidosis, type II diabetes and spongiform encephalopathies like, for example, Bovine Spongiform Encephalopathy (BSE) and Creutzfeldt-Jakob's disease.

In addition, deleterious effects of aggregated proteins are not solely mediated by amyloid fibrillar depositions of proteins, but also by soluble oligomers of aggregates with amyloid-like properties and by diffuse amorphous aggregates.[3,5] The recent finding that toxicity is an inherent property of misfolded proteins implies a common mechanism for conformational diseases.[1,3,6]

We showed that tissue-type plasminogen activator (tPA) and factor XII (FXII) are specifically activated by many polypeptides, once they have adopted the cross-β structure conformation.[7] This led us to recognize that a "cross-β structure pathway" exists that regulates the recognition and clearance of unwanted proteins.[1] Polypeptides can refold spontaneously, at the end of their life cycle, or refolding can be induced by environmental factors such as pH, glycation, oxidative stress, heat, irradiation, mechanical stress, proteolysis or contact with denaturing surfaces or compounds, such as negatively charged lipids, plastics or biomaterials. At least part of the polypeptide refolds and adopts the amyloid-like cross-β structure conformation. This cross-β structure containing conformation is then the signal that triggers a cascade of events that induces clearance and breakdown of the particle. When clearance is inadequate unwanted polypeptides can aggregate and form toxic structures ranging from soluble oligomers up to precipitating fibrils and amorphous plaques. Such cross-β structure containing structures underlie various diseases, depending on the polypeptide that accumulates and on the part of the body where accumulation occurs.

The presence of cross-β structures in proteins triggers multiple responses. As mentioned, cross-β structure comprising proteins can activate tPA and FXII, thereby initiating the fibrinolytic system and the contact system of hemostasis. Besides activation of the coagulation system through FXII, the cross-β structure conformation may induce coagulation, platelet aggregation and blood clotting via direct platelet activation and/or the release of tissue factor (Tf) by activated endothelial cells. In addition, the complement system is another example of a proteolytic cascade that is activated by cross-β structures. This system can be activated by the amyloid-β peptide associated with Alzheimer's Disease or by zirconium or aluminum or titanium. The latter being compounds that can induce cross-β structure conformation in proteins. The innate and adaptive immune systems are yet another example. Amyloid-β activates the innate and adaptive immune response.[8] β2-glycoprotein I is an auto-immune antigen only upon contact with a negatively charged lipid surface, such as cardiolipin.[9] We have now shown that cardiolipin induces cross-β structure conformation in β2-glycoprotein I (described in more detail elsewhere). Moreover, we have shown that ligands for Toll-like receptors that are implicated in the regulation of immunity induce cross-β structure conformation in proteins. These ligands include lipopolysaccharide (LPS) and cytosine and guanine separated by phosphate oligodeoxynucleotides (CpGODN) (described in more detail elsewhere).

The β2-glycoprotein I protein (β2GPI), together with IgM antibodies, Clq and likely other proteins are all also acting in another way in the proposed cross-β structure pathway. It is assumed that a set of cross-β structure-binding proteins bind specifically to sites of "danger," e.g., negatively charged phospholipids, amyloid plaques, sites of ischemic injury, necrotic areas, all with its own specificity. Upon binding, the "dangerous" condition is neutralized and, for example, excessive coagulation at negatively charged lipid surfaces will not occur. Secondly, the proteins bound to the "dangerous" site undergo a conformational change resulting in the formation of the cross-β structure conformation. This fold then acts as a signal for cross-β structure-binding proteins that are part of the "cross-β structure pathway," leading to the clearance of the bound protein or protein fragment and removal of the "danger."

The cross-β structure pathway also acts in yet another way. Proteins that circulate in complex with other proteins may comprise a shielded cross-β structure conformation. Once the protein is released from the accompanying protein, the cross-β structure becomes exposed, creating a binding site for cross-β structure-binding proteins of the cross-β structure pathway. This then results in breakdown or clearance of the released protein. An example is factor VIII, which circulates in complex with von Willebrand factor (vWF). In this complex, factor VIII is prevented from clearance, so vWF covers the clearance signal that becomes exposed after the complex is dissociated. This clearance signal is the cross-β structure. Treatment of hemophilia patients with recombinant factor VIII (FVIII) may induce inhibitors (anti-FVIII autoantibodies) because the patients lack sufficient vWF to protect the clearance signal comprising the cross-β structure conformation. Excess exposure of FVIII comprising cross-β structure conformation may induce activation of the immune system and generation of anti-FVIII antibodies similar to the generation of anti-β2GPI autoimmune antibodies by β2GPI bound to negatively charged phospholipids and possibly autoimmune responses.

The compounds listed in Table 1 and the proteins listed in Table 2 all bind to polypeptides with a non-native fold. In literature, this non-native fold has been designated as protein aggregates, amorphous aggregates, amorphous deposit, tangles, (senile) plaques, amyloid, amyloid-like protein, amyloid oligomers, amyloidogenic deposits, cross-β structure, β-pleated sheet, cross-β spine, denatured protein, cross-β sheet, β-structure rich aggregates, infective aggregating form of a protein, unfolded protein, amyloid-like fold/conformation and perhaps alternatively. The common theme amongst all polypeptides with an amyloid-like fold, that are ligands for one or more of the compounds listed in Tables 1 and 2, is the presence of a cross-β structure.

The compounds listed in Tables 1 and 2 are considered to be only an example of compounds known to day to bind to amyloid-like protein conformations. The lists are thus non-limiting. More compounds are known today that bind to amyloid-like protein conformation. For example, in Australian Patent AU2003214375 it is described that aggregates of prion protein, amyloid, and tau bind selectively to polyionic-binding agents such as dextran sulphate or pentosan (anionic), or to polyamine compounds such as poly(diallyldimethylammonium chloride) (cationic). Compounds with specificity for amyloid-like folds of proteins listed in this patent and elsewhere are equally suitable for methods and devices disclosed in this patent application. Moreover, also any compound or protein related to the ones listed in Tables 1 and 2 are covered by the claims. For example, point mutants, fragments, recombinantly produced combinations of cross-β structure-binding domains and deletion and insertion mutants are part of the set of compounds as long as they are capable of binding to protein with cross-β structure conformation (i.e., as long as they are functional equivalents). Even more, also any newly discovered small molecule or protein that exhibits affinity for a protein and/or peptide with the cross-β structure conformation can be used in any one of the methods and applications disclosed here.

The compounds listed in Table 3 are also considered to be part of the "Cross-β structure pathway," and this consideration is based on literature data that indicates interactions of the listed molecules with compounds that likely comprise the cross-β structure conformation but that have not been disclosed as such.

Generally, for the production of a proteinaceous pharmaceutical composition, a protein or proteinaceous molecule or compound is isolated from an animal or plant or is synthesized in vitro. Proteins or proteinaceous molecules or compound are subjected to a number of processes like, for example, a purifying or isolating process from an animal or plant source, or a synthesis process, such as, for example, a peptide synthesis process, or a synthesis in a plant cell, a yeast cell or a bacteria, or a synthesis in a eukaryotic cell, and/or a manufacturing process, like, for example, the coupling of chemical molecules to a peptide or protein, and/or an isolation procedure or a purification procedure, and/or concentrating process, like, for example, the isolation of recombinant protein from a bacterial production cell, or purification by a physical, or a chemical, or an immunological isolation method, and/or a formulation and/or a storage process, including, for example, a lyophilization process and/or the addition of a suitable stabilizer, a diluent and/or an adjuvant.

Any one of these processes affects the folding of a protein or a proteinaceous compound. Quality control in a manufacturing process preferably aims at identifying and/or minimizing the deleterious effects of each process step for the pharmaceutical composition, thereby increasing the activity of the composition in the final composition and/or decreasing the undesired side effects of the composition.

Alteration of a protein or proteinaceous composition is generally detected by measuring a specific binding site or a specific activity of the protein or proteinaceous composition, or an increase in size or multimerization state of the protein or proteinaceous composition, or a decrease in therapeutic activity of the proteinaceous composition.

As to the first of the methods, a partially unfolded or misfolded protein can still expose a specific binding site. Therefore, testing the quality of a pharmaceutical composition by only testing for a specific binding site is not always a reliable method, because the partial unfolding or degradation of the protein is not detected.

The second of the methods, the size-related detection method is based on the concept that denaturation leads to aggregation of proteins, thereby increasing the size of the proteinaceous molecule. One of several methods for detecting an increase in size of proteins is called size exclusion chromatography. Nowadays, size exclusion chromatography is widespread used as a method to analyze the contents of a protein drug. This technique is generally accepted for the testing of protein drug stability (see, e.g., on the internet at etd.utmem.edu/WORLD[13] ACCESS/ymi/reviewofanalyticmethod.htm).

Because the detection method only detects the size of proteinaceous molecules, it cannot detect misfolded proteins or proteins with increased content of cross-β structure conformation that have not aggregated or increased in size. Therefore, quality control based on the above-described method of detecting an increase in size of the proteinaceous molecules, does not prevent undesired side effects caused by conformational changes such as, for example, cross-β structure conformation formed upon denaturation, proteolysis, chemical modification, or unfolding of proteins, in the absence of increased molecular size. Moreover, nowadays guidelines that determine the acceptable amounts of aggregates in proteinaceous drug solutions are based on technical limitations of the available purification methods, rather than on knowledge about expected undesired side effects of the aggregated proteins. Therefore, a better quality control method is highly needed by scientists involved in development of proteinaceous compositions and/or pharmaceutically active compounds and formulations and for manufacturers of proteins or proteinaceous compositions and/or vaccines and/or pharmaceutical compositions and constituents thereof, comprising a protein.

The present invention discloses that unfolded and/or misfolded proteins or proteinaceous molecules like, for example, molecules that are proteolyzed, denatured, unfolded, glycated, oxidized, acetylated, multimerized or otherwise structurally altered, adopt a cross-β structure conformation. Furthermore, the present invention discloses that unwanted and/or toxic side effects of pharmaceuticals are caused by proteins present in the pharmaceutical and adopting a cross-β structure conformation.

The invention provides methods to detect the presence of cross-β structure conformation. The invention provides also methods for the removal of proteins or peptides from pharmaceutical compositions comprising a cross-β structure conformation, thereby reducing the toxicity and unwanted side effects and increasing the specific activity per gram protein of the compositions. Therefore, the methods of the invention provide a person skilled in the art with a method for monitoring and optimizing the production methods and storing conditions of a pharmaceutical composition.

In one embodiment, the present invention provides a method for detecting a protein and/or peptide comprising a cross-β structure conformation in a pharmaceutical composition or any of its constituents comprising a protein, the method comprising: contacting the pharmaceutical composition or any of its constituents comprising a protein comprising at least one cross-β structure-binding compound, preferably selected from Tables 1-3 or functional equivalents thereof, resulting in a bound cross-β structure, detecting whether bound cross-β structures are present in the pharmaceutical composition or any of its constituents comprising proteins.

The invention discloses that various binding molecules or binding compounds, as described in Tables 1, 2 and/or 3 of the application, alone or in combination with other binding compounds, are capable of binding to a protein and/or peptide comprising a cross-β structure conformation. Binding of one or more of the cross-β structure-binding compounds of Tables 1, 2 and/or 3 or others to a protein and/or peptide comprising across-β structure conformation is detected by means of a visualization reaction as, for example, by fluorescent staining or an enzymatic or calorimetric detection, or by any other visualization system available to a skilled person. Therefore, the invention provides a method of the invention, wherein the cross-β structure-binding compound is a compound according to Table 1, or Table 2, or Table 3 or a functional equivalent of any of the compounds and/or a combination of any of the compounds.

In Tables 1, 2 and/or 3, various different binding compounds are described that bind to compounds with cross-β structure conformation. For example, Table 1 comprises among other, dyes like Thioflavin T, Thioflavin S, and Congo Red, that are used for staining amyloid molecules in histological sections or in solution. Table 2 comprises bioactive compounds binding to compounds comprising cross-β structure conformations such as tissue-type plasminogen activator, factor XII, fibronectin, and others.

In Table 3, proteins are disclosed that are involved in the cross-β structure pathway, like for example, antibodies, heat shock proteins and receptors. In another embodiment, the invention provides a protein-specific way of detecting and removing compounds with cross-β structure conformations, by combining the protein-specific binding of an antibody or functional part thereof (i.e., a part of an antibody that specifically binds to a protein), with the compound with cross-β structure conformations binding of a cross-βstructure-binding compound. Therefore, the invention also provides molecular recognition units binding to compounds with cross-β structure conformations, single chains of antibodies, or recombinant binding molecules. The invention also provides bi-specific binding molecules, for example, comprising the binding portion of tPA and an antibody, or the binding portion of a bioactive compound binding to proteins with cross-β structure conformations with the binding portion of an antibody.

A constituent of a pharmaceutical composition is any substance that is present in or added to a proteinaceous molecule to produce a pharmaceutical composition. The invention also relates to any component that has come into contact with the pharmaceutical composition during the manufacturing process and storage. Because cross-β structure conformations generally develop in a protein or a proteinaceous compound, a constituent comprising a protein is a constituent that may contain a cross-β structure conformation.

The term "constituent of a pharmaceutical composition" comprises any substance suitable for administering a proteinaceous composition to a body of a human or animal. The constituent comprises, for example, carrier substances and conserving substances, fluids for injection or ingestion, mannitol and cellulose, and the usual excipients for parenteral, enteral, ocular, otic, and transdermal administration.

In a preferred embodiment of the invention detection of a cross-β structure is in a soluble state. In this embodiment, a cross-β structure-binding compound is added to a pharmaceutical composition or to a constituent of the composition, the constituent comprising a protein, resulting in binding of the protein and/or peptide comprising a cross-β structure conformation with the binding compound. The bound protein and/or peptide comprising across-β structure conformation is then detected by physical or chemical or enzymatic detection methods. In another preferred embodiment of the invention, a compound of Tables 1, and/or 2, and/or 3 is attached to a solid surface or solid phase, either by chemical or physical means or by another binding molecule. Detection of a proteinaceous compound such as a protein, a peptide, or a with cross-β structure results from contacting the pharmaceutical composition or any of its constituents with the cross-β structure-binding compound derived from the group depicted in Tables 1, and/or 2, and/or 3, or a functional equivalent thereof, more preferably with a solid phase comprising a cross-β structure-binding compound derived from the group depicted in Tables 1, and/or 2, and/or 3 or a functional equivalent thereof, and measuring or detecting the protein and/or peptide comprising across-β structure bound to the solid phase. In yet another embodiment, a cross-β structure-binding compound is attached to a solid phase after binding a protein and/or peptide comprising across-β structure. As a solid phase, many materials are suitable for binding a cross-β structure-binding compound, such as for example, glass, silica, polystyrene, polyethylene, nylon, vinyl, sepharose beads, beads containing iron or other metals and so on. In one embodiment of the invention, the solid phase has the physical form of beads. In another embodiment, the solid phase has the shape of a tube or a plate or a well in, for instance an ELISA plate, or a dipstick. Numerous binding techniques are available for coupling the cross-β structure-binding compounds to the solid phase, like for example, Cyanogen Bromide (CnBr), NHS, Aldehyde, epoxy, Azlactone, biotin/streptavidin, and many others. The amount of bound protein and/or peptide comprising cross-β structures is measured, for example, by staining the protein and/or peptide comprising cross-β structures and is a measure for the quality of the proteins in the pharmaceutical composition. In another embodiment, the cross-β structure-binding compound is bound to another compound which in turn is bound to another compound and so on. This indirect binding is suitable for increasing the efficiency of the detection and removal of protein and/or peptide comprising across-β structure in a pharmaceutical composition and any of its constituents comprising a protein.

The compounds of Tables 1, 2 and 3 are various in chemical size and structure. A common characteristic of all compounds of Tables 1 and 2 is their propensity to bind to protein and/or peptide comprising across-β structure. Compounds that comprise a function which is similar or equivalent to the compounds of Table 1, like the compounds in Tables 2 or 3, have been detected by direct binding experiments as disclosed in the invention, in literature and in European Patent Application No. 02077797.5. A functional equivalent of a binding compound of the invention is a substance that exerts a similar function as the compound, i.e., a substance that binds to a compound with cross-β structure conformation.

Therefore, the present invention discloses a method for detecting a protein and/or peptide comprising across-β structure wherein the cross-β structure-binding compound is a compound according to Table 1, or Table 2, or Table 3 or a functional equivalent of any of the compounds, or a combination of any of the compounds. The methods of the invention are useful for controlling the different stages of a manufacturing process of a pharmaceutical composition. In general, the specification of a process for manufacturing a pharmaceutical composition is described in a handbook according to good manufacturing practice (GMP) and good laboratory practice (GLP). GLP and GMP quality control is a valuable tool for manufacturers of pharmaceutical compositions and for manufacturers of proteinaceous constituents for the pharmaceutical compositions and it helps and enables them to produce products of a steady quality and to increase the quality by monitoring the manufacturing and storage process. The present invention discloses methods that help manufacturers to detect compounds with cross-β structures in a pharmaceutical product and/or in its constituents. A qualitative difference is thus made between products with cross-β structures or products without cross-β structures, or with low levels of cross-β structures. By monitoring the processes with methods of the invention, manufacturers are capable of omitting processes or chemicals or physical conditions or circumstances that induce the formation of cross-β structures, and it enables them to select processes or chemicals or circumstances that do not induce cross-β structure conformations and/or raise the level of cross-β structure conformations in a pharmaceutical composition or any of its constituents and/or excipients comprising a protein.

In one preferred embodiment, the present invention discloses a method for detecting and/or measuring a cross-β structure-inducing ability of a solid surface, by contacting the surface with a protein and detecting denatured protein by subsequently contacting the surface with a cross-β structure-binding compound. With the method of the invention, a person skilled in the art is capable of selecting materials for a recombinant protein container. The container comprises a reaction vessel, a production vessel, a storage vessel and/or a tube connecting the vessels. The above-described method is also suitable for detecting and/or measuring a cross-β structure-inducing ability of a molecule, for example, of a salt, or a dye, or an enzyme, or a chemical compound such as, for example, alcohol or formaldehyde or glucose. Therefore, the present invention discloses in another embodiment a method for detecting and/or measuring a cross-β structure-inducing ability of a molecule, by contacting the molecule with a protein and detecting denatured protein by subsequently contacting the molecule and/or the protein with a cross-β structure-binding compound. Molecules that have the ability to induce a cross-β structure are then removed or avoided in the production, purification and storage of a recombinant protein and/or a pharmaceutical composition. Therefore, the present invention enables a person skilled in the art to avoid the use of material comprising the molecule as a part of the wall of a container for production, purification, or storage of the proteinaceous molecule. In another embodiment, the invention teaches the person skilled in the art to avoid molecules inducing cross-β structure in the preparation of a proteinaceous solution or a pharmaceutical composition. Therefore, the present invention provides a method for selecting molecules for production and/or dilution, and/or preservation of a recombinant proteinaceous composition.

In yet another embodiment, the present invention discloses a method for detecting and/or measuring a cross-β structure-inducing ability of a physical condition such as for example, pH, pressure, stirring, shaking, temperature, salt concentration and/or protein concentration. A recombinant proteinaceous composition is subjected to various physical conditions and the increase of the amount of cross-β structure conformations is measured by contacting the proteinaceous composition with a cross-β structure-binding compound according to a method of the invention. Binding of a protein with cross-β structure conformation from the proteinaceous composition with a cross-β structure-binding compound is detected using the methods of the invention. The above-described method is a valuable tool for detecting cross-β structure-inducing circumstances during production, purification, and storage. Therefore, the present invention discloses a process to improve production, purification and storage of recombinant proteinaceous material.

Therefore, the present invention discloses a method according to the invention for controlling a manufacturing process, and/or storage process of a pharmaceutical composition or any of its constituents comprising a protein, the method comprising contacting the pharmaceutical composition or any of its constituents comprising a protein with at least one cross-β structure-binding compound resulting in a bound protein and/or peptide comprising a cross-β structure, detecting whether a bound protein and/or peptide comprising a cross-β structure is present in the pharmaceutical composition or any of its constituents comprising a protein at various stages of the manufacturing and/or storage process.

In another embodiment of the invention, protein and/or peptide comprising a cross-β structure bound to a binding molecule are separated from the pharmaceutical composition or any of its constituents comprising a protein, for example, by collecting the solid phase comprising the cross-β structure-binding compound, bound to protein and/or peptide comprising cross-β structures. Separation of the solid phase is, for example, performed by g-forces like, for example, by gravity, or by centrifugation, or by magnetic forces, or by filtration. Separation is performed in a continuous mode or batch-wise, or with a combination of a batch-wise and a continuous mode. Therefore, the present invention discloses a method for removing a protein and/or peptide comprising a cross-β structure from a pharmaceutical composition or any of its constituents, the method comprising contacting the pharmaceutical composition or any of its constituents comprising a protein with at least one cross-β structure-binding compound, allowing binding of the protein and/or peptide comprising a cross-β structure to the cross-β structure-binding compound, and, separating the bound protein and/or peptide comprising a cross-β structure from the pharmaceutical composition or any of its constituents comprising a protein.

A non-limiting number of compounds capable of binding to protein and/or peptide comprising a cross-β structure are disclosed in Tables 1, 2, and 3. Therefore, the present invention discloses a method according to the invention, wherein the cross-β structure-binding compound is a compound according to Table 1, or Table 2, or Table 3 or a functional equivalent of any of the compounds.

For efficient removal of bound proteins and/or peptides comprising a cross-β structure, a cross-β structure-binding compound is attached to another binding compound or to a solid phase by chemical or physical methods.

As a solid phase, many materials are suitable for binding a cross-β structure-binding compound, such as for example, glass, silica, polystyrene, polyethylene, nylon, vinyl, sepharose beads, beads containing iron or other metals and so on. In one embodiment of the invention, the solid phase has the physical form of beads. In another embodiment the solid phase has the shape of a tube or a plate or a well in, for instance an ELISA plate, or a dipstick. Numerous binding techniques are available for coupling the cross-β structure-binding compounds to the solid phase, like for example, Cyanogen Bromide (CnBr), NHS, Aldehyde, epoxy, Azlactone, biotin/streptavidin, and many others.

As described above, it generally depends on the chemical attachment method that is selected how and when the cross-β structure-binding compound is attached to another molecule or compound. For example, a preferred binding of the compound of Table 1 to another compound occurs before binding a compound with cross-β structure conformation, or more preferred during the process of the binding of a compound with cross-β structure conformation, or most preferred after binding of a compound with cross-β structure conformation. Therefore, the present invention discloses a method according to the invention, wherein the cross-β structure-binding compound is bound to a second compound before, during or after the binding of the cross-β structure-binding compound to a compound with cross-β structure conformation.

As described above, it depends on the attachment method and on the type of solid phase how and when the cross-β structure-binding compound and/or its second binding compound is attached to a solid phase. In one embodiment, the compound of Table 1 is attached to a solid phase, and in another embodiment of the invention, the compound of Table 1, 2, or 3 or an equivalent thereof is first attached to a second binding compound, which in its turn is attached to a solid phase. Therefore, the present invention discloses a method according to the invention, wherein the second compound is bound to a solid face. For example, the second compound comprises an antibody directed against part of a compound of Table 1, 2, or 3, or comprises a chemical linker that is capable of binding a compound of Table 1, 2, or 3. Although in many cases it will be enough to contact a compound with cross-β structure conformation with a cross-β structure-binding compound, or the complex with a second binding compound, it of course also in the present invention that the second binding compound is also capable of binding to a third binding compound or even to a fourth or fifth and so on. Therefore, the present invention in another embodiment discloses a method of the invention, wherein the cross-β binding compound, bound to a second compound is further bound to a third or fourth or further binding compound before, during or after the binding of the cross-β binding compound to a compound with cross-β structure conformation. In a preferred embodiment a third or fourth or further binding compounds is bound to a solid phase. Therefore, the present invention also discloses a method, wherein the second, third, or fourth compound is bound to a solid phase In another embodiment of the invention, the continued binding of more binding molecules induces the formation of aggregates that do not need a further solid phase to be separated from the pharmaceutical composition or any of its constituents comprising a protein.

The presence of bound cross-β structures is in another embodiment detected by an enzymatic assay.

As an example of an enzymatic assay the specification provides tPA and plasminogen and plasmin substrate S-2251 (Chromogenix Spa, Milan, Italy) in a suitable buffer. Preferably, the buffer is HBS (10 mM HEPES, 4 mM KC1, 137 mM NaCl, pH 7.3). Standard curve is made with a control with cross-β structure conformation. Titration curves are made with a sample before and after a treatment/exposure to a putatively denaturing condition. Alternatively the detection of bound proteins or peptides comprising cross-β structures is achieved by a test wherein factor XII with activated factor XII substrate S-2222 or S-2302 is present in a suitable buffer. Preferably, the buffer is 50 mM, 1 mM EDTA, 0.001% v/v Triton-X100. Standard curves are made with known cross-β structure rich activators of factor XII; preferably DXS500k with a protein; preferably the protein is endostatin or albumin; preferably with glycated hemoglobin, Aβ, amyloid fibrin peptide $NH_2$-148KRLEVDIDIGIRS160-COOH with K157G mutation (SEQ ID NO:1). In yet another embodiment, the presence of bound proteins or peptides comprising cross-β structures is detected by a test comprising factor XII with prekallikrein and high molecular weight kininogen and either substrate Chromozym-PK for kallikrein or a substrate for activated factor XII in a suitable buffer; preferably HBS. Standard curves are made with known cross-β structure rich activators of factor XII; preferably DXS500k or kaolin with a protein; preferably the protein is endostatin or albumin; preferably with glycated hemoglobin, Aβ, amyloid fibrin peptide $NH_2$-148KRLEVDIDIGIRS160-COOH with K157G mutation (SEQ ID NO:1).

The present invention discloses a method for both the detection and the removal of protein and/or peptide comprising a cross-β structures from a pharmaceutical composition and/or any of its constituents. Because protein and/or peptide comprising cross-β structures are also capable of inducing the unfolding and degeneration of proteins, the presence of protein and/or peptide comprising a cross-β structure is deleterious for the protein in a pharmaceutical composition. By removing protein and/or peptide comprising a cross-β structure from a pharmaceutical composition, the specific activity per gram protein of the pharmaceutical composition is preferably retained. Because protein and/or peptide comprising a cross-β structure are toxic and induce undesired side effects after administration in a human or animal, removal of the protein and/or peptide comprising a cross-β structure at least diminishes the undesired side effects upon administration. In a preferred embodiment, the undesired side effects are even prevented. Therefore, the present invention discloses a method for decreasing and/or preventing undesired side effects of a pharmaceutical composition and/or increasing the specific activity per gram protein, the method comprising detecting and removing any unfolded protein or peptide and/or aggregated protein or peptide and/or multimerized protein or peptide comprising a cross-β structure from the pharmaceutical composition or any of its constituents comprising a protein.

A pharmaceutical composition, which is processed according to any one of the methods of the present invention, comprises less protein and/or peptide comprising a cross-β structure, and is, therefore, less toxic, thrombogenic, immunogenic, inflammatory or harmful for a mammal including a human after administration of the pharmaceutical composition. Furthermore, because of the decreased presence of protein and/or peptide comprising a cross-β structure conformations in the pharmaceutical composition, the purity and the biological activity of the pharmaceutical composition is preferably higher per gram protein present in the pharmaceutical composition, and therefore, more pharmaceutical composition can be made from an amount of protein and still achieve the same pharmacological effect. A pharmaceutical composition that is purified by any of the methods of the invention is, therefore, of higher quality, and exerts less side effects than a pharmaceutical composition that is not purified. The difference between a pharmaceutical composition according to the invention and another pharmaceutical composition is in the amount of compounds with cross-β structure conformations detectable in the pharmaceutical composition according to any of the methods of the invention.

Therefore, the present invention in another embodiment discloses a pharmaceutical composition or any of its constituents comprising a protein, the composition obtainable by a method according to a method of the invention.

In another embodiment, the specification provides a kit of parts, comprising, for example, one or more cross-β structure-binding compounds as depicted in Tables 1, or 2, or possibly 3, and optionally one or more compounds binding the cross-β structure-binding compound, and a means for detecting bound cross-β structure as described elsewhere in this specification, thereby making the kit suitable for carrying out a method according to the invention such as, for example, detecting compounds with cross-β structure conformations, and or removing compounds with cross-β structure conformations from a pharmaceutical composition or any of its constituents comprising a protein. The specification provides in one embodiment of a kit, for example, a filter-like element-binding compounds with cross-β structure or binding cross-β structure-binding compounds. The filter is placed in or on a syringe through which a pharmaceutical composition is passed before inoculation or administration to a mammal. In another embodiment, the filter is used in the production or packaging of a pharmaceutical composition or any of its constituents. In another embodiment, the kit of the specification provides an ELISA plate, or a dipstick for detecting compounds with cross-β structure in a pharmaceutical composition or any of its constituents or a filtration device for removing compounds with cross-β structure conformations of a pharmaceutical composition or any of its constituents.

After removal of the cross-β structure from a pharmaceutical composition or any of its constituents, the resulting pharmaceutical composition or any of its constituents is tested again to control whether the amount of cross-β structures in the composition or any of its constituents has actually decreased. The decrease in cross-β structures and, therefore, the decrease in toxicity, are tested by conventional methods known in the art such as in vitro or in in vivo tests for toxicity and/or thrombogenicity and/or immunogenicity of the pharmaceutical composition or any of its constituents.

DESCRIPTION OF THE FIGURES

FIG. 2: Activation of factor XII by protein aggregates with cross-β structure conformation. Panel A: Like kaolin, amyloid-like peptide aggregates of FP13 and Aβ stimulate the activation of factor XII, as detected by the conversion of Chromozym PK, upon formation of kallikrein from prekallikrein by activated factor XII. Buffer control and non-amyloid controls FP10 and mIAPP do not activate factor XII. Panel B: Like FP13 and Aβ, also cross-β structure conformation rich peptides LAM12 and TTR11 stimulate factor XII activation, to a similar extent as kaolin. Panel C: In the chromogenic factor XII/kallikrein activity assay, the stimulatory activity of 150 μg $ml^{-1}$ kaolin is strongly dependent on the presence of 1 mg $ml^{-1}$ albumin in the assay buffer. Albumin alone also shows to some extent factor XII/prekallikrein activating properties, likely due to the presence of amyloid-like aggregates in the albumin solution after dissolving it from a lyophilized stock. Panel D: similar effects are seen with albumin and DXS500k. Panel E: Like albumin endostatin is a requirement for kaolin-induced factor XII activation. Panel F: With DXS500k and endostatin, similar effects are seen in the factor XII activation assay as with albumin and DXS500k. Panel G: Contacting plasma, lysozyme and γ-globulins to DXS500k results in activation of tPA and Plg, as measured in the chromogenic tPA/Plg activation assay. DXS500k alone also results in some activation. Plasma, lysozyme or γ-globulins controls do not activate tPA and Plg. Panel H: Overnight incubation at room temperature of plasma with kaolin or DXS500k results in increased fluorescence of amyloid dye ThT, when compared to incubation with buffer. Panel I: Incubation of γ-globulins with kaolin or DXS500k also induces increased ThT fluorescence. Panel J: Only DXS500k induces ThT fluorescence with lysozyme. Kaolin incubation results only in a small increase in ThT fluorescence, when compared to buffer. Panels K-N: In an ELISA set-up tPA binds specifically to plasma proteins (Panel K), γ-globulins (Panel L), lysozyme (Panel M) and factor XII (Panel N) that were preincubated overnight with DXS500k, whereas tPA does not bind to buffer-incubated proteins. K2P tPA that lacks the F domain does not bind to surface-contacted proteins. Panel O: In the tPA ELISA Hb-AGE with amyloid-like properties was used as a positive control for tPA binding. Panel P: Autoactivation of factor XII is established by incubating purified factor XII with DXS500k or with various amyloid-like protein aggregates with cross-β structure conformation, in the presence of chromogenic substrate S-2222.

FIG. 3: Presence of amyloid cross-β structure conformation in commercially available formulated protein medicine. Panels A-D: With protein therapeutics stored at the recommended temperature of 4° C., influence on Congo red—(Panel A) and ThT fluorescence (Panel B) was established as well as the ability to activate tPA (Panel C) and factor XII (Panel D), as determined with chromogenic assays which record Pls and kallikrein activity, that is established upon activation of Plg by tPA and prekallikrein by factor XII, respectively. Gelatin, Cealb and FVIII clearly enhance Congo red fluorescence. Cealb, GH and FVIII enhance ThT fluorescence. GH and insulin potentiate Plm activity. Amyloid γ-globulins at 100 μg $ml^{-1}$ was used as a positive control. Zinc-insulin and insulin activate factor XII. Kaolin at 150 μg $ml^{-1}$ was used as a positive control. Panel E: Both modified gelatin for infusion stored at 4° C. and at 37° C. show enhanced Congo red fluorescence comparable to the positive control, 25 μg $ml^{-1}$ Aβ. Panel F: Only modified gelatin for infusion that was stored at 37° C., and not gelatin stored at 4° C., exhibits factor XII stimulatory activity, as measured in a chromogenic kallikrein activity assay. The positive control for factor XII mediated prekallikrein activation was 150 μg $ml^{-1}$ kaolin. Panel G: tPA ELISA showing the binding of tPA to immobilized protein therapeutics zinc-insulin, an antibody, FVIII and Cealb. Positive control in the ELISA was Hb-AGE, that is not shown for clarity. Panel H: tPA ELISA showing the binding of tPA to immobilized formulated Cealb and GH. $K_D$s are 23 nM for Cealb and 72 nM for GH. Panel I: TEM image of modified gelatin showing various relatively condense aggregates. The scalebar is 1 μm. Panel J: TEM image of GH showing a linear, a branched and a condense particle all apparently composed of spherical particles. The scale bar is 100 nm. Panel K: TEM image of zinc-insulin showing the appearance of insulin as thin unbranched fibrils with varying length. The scale bar represents 100 nm. Panel L: TEM image of protein therapeutic Cealb, stored at 4° C. Scale bar: 100 nm. Panel M: TEM image of Novo Rapid insulin, stored at 4° C. Scale bar: 100 nm. Panel N: Influence of storage temperature on ThT fluorescence enhancement by protein therapeutic Reopro. Panel O: TPA activating properties are largely dependent on the storage temperature of Reopro, as assessed in a tPA activation assay. Panel P: TEM image of ReoPro anticoagulant, stored at 4° C. Scale bar: 1 μm.

FIG. 5: Binding of factor XII and tPA to $\beta_2$-glycoprotein I and binding of anti-$\beta_2$GPI auto-antibodies to recombinant $\beta_2$GPI. Panel A: Chromogenic Plg-activation assay showing the stimulatory activity of recombinant $\beta_2$GPI on the tPA-mediated conversion of Plg to Pls. The positive control was amyloid fibrin peptide FP13. Panel B: In an ELISA, recombinant $\beta_2$GPI binds to immobilized tPA, whereas $\beta_2$GPI purified from plasma does not bind. The $k_D$ is 2.3 μg $ml^{-1}$ (51 nM). Panel C: In an ELISA, factor XII binds to purified recombinant human $\beta_2$GPI, and not to $\beta_2$GPI that is purified from human plasma, when purified factor XII is immobilized onto ELISA plate wells. Recombinant $\beta_2$GPI binds with a $k_D$ of 0.9 μg $ml^{-1}$ (20 nM) to immobilized factor XII. Panel D: Western blot incubated with anti-human factor XII antibody. The $\beta_2$GPI was purified either from fresh human plasma or from plasma that was frozen at −20° C. and subsequently thawed before purification on a $\beta_2$GPI affinity column. Eluted fractions are analyzed on Western blot after SDS-PA electrophoresis. When comparing lanes 2-3 with 4-5, it is shown that freezing-thawing of plasma results in co-purification of factor XII together with the $\beta_2$GPI. The molecular mass of factor XII is 80 kDa. Panel E: In an ELISA recombinant $\beta_2$GPI efficiently inhibits binding of anti-$\beta_2$GPI auto-antibodies to immobilized $\beta_2$GPI, whereas plasma $\beta_2$GPI has a minor effect on antibody binding. Anti-$\beta_2$GPI auto-antibodies were purified from plasma of patients with the auto-immune disease Anti-phospholipid syndrome. Panel F: Exposure of 25 $\mu g\ ml^{-1}$ $\beta_2$GPI, recombinantly produced (r$\beta_2$GPI) or purified from plasma (n$\beta_2$GPI), to 100 μM CL vesicles or to 250 $\mu g\ ml^{-1}$ dextran sulphate 500,000 Da (DXS) induces an increased fluorescence of ThT, suggestive for an increase in the amount of cross-β structure in solution. Signals are corrected for background fluorescence of CL, DXS, ThT and buffer. Panel G: Binding of tPA and K2P tPA to $\beta_2$GPI immobilized on the wells of an ELISA plate, or to β2GPI bound to immobilized CL is assessed. $B_2$GPI contacted to CL binds tPA to a higher extent than $\beta_2$GPI contacted to the ELISA plate directly. K2P tPA does not bind to $\beta_2$GPI. TPA does not bind to immobilized CL. Panel H: Transmission electron microscopy images of 400 $\mu g\ ml^{-1}$ purified plasma β2GPI alone (1) or contacted with 100 μM CL (2, 3) and of 400 $\mu g\ ml^{-1}$ purified recombinant β2GPI (4).

DETAILED DESCRIPTION OF THE INVENTION

Figure 1:
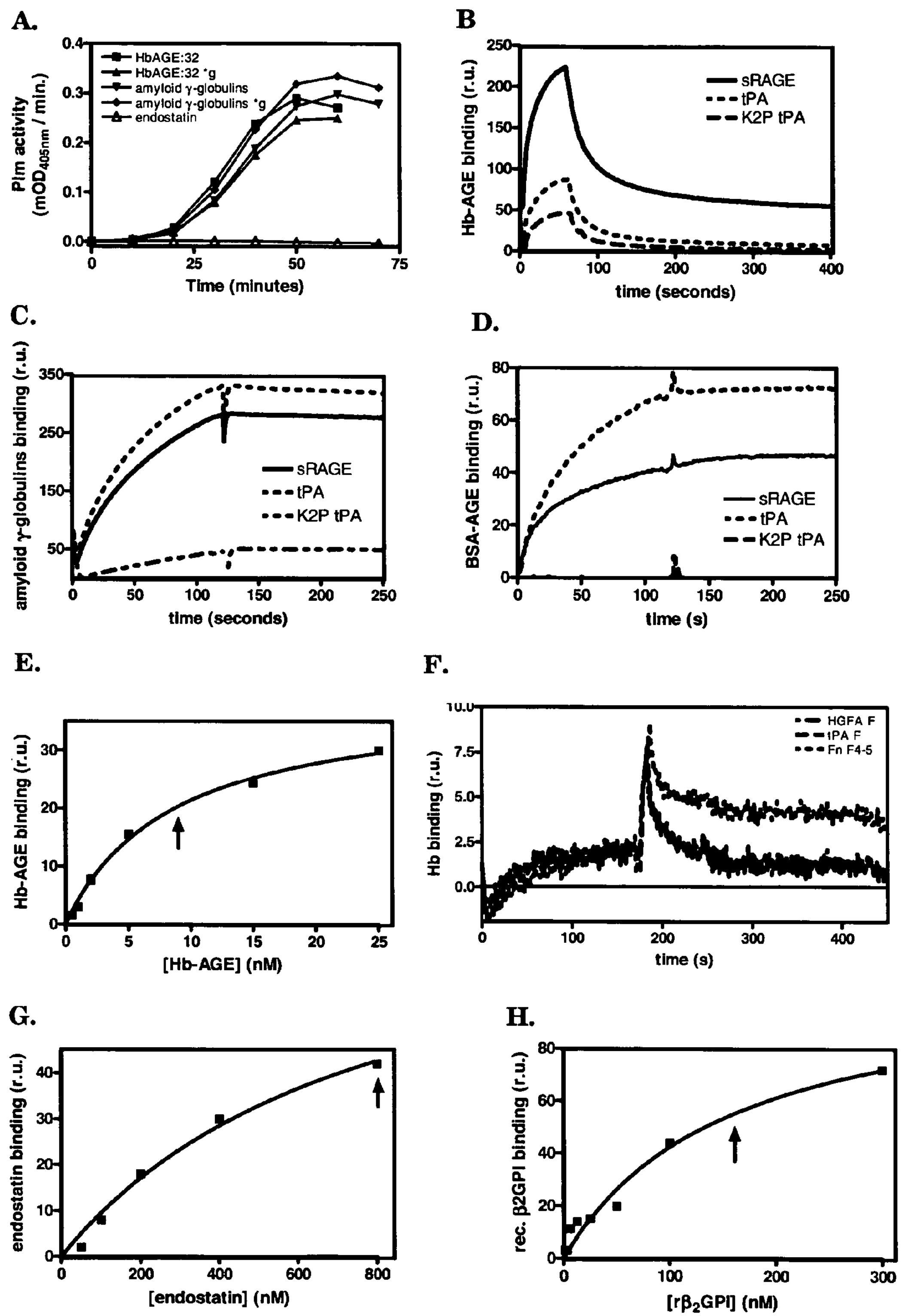
FIG. 1: Binding of polypeptides with cross-β structure conformation to tPA, soluble receptor for advanced glycation end products (sRAGE) and Fn type I domains, studied with Biacore surface plasmon resonance. Panel A: TPA activation assay showing that 10-minute centrifugation at 16,000*g of Hb-AGE and amyloid Y-globulins hardly influences the tPA activating properties of the supernatant when compared to uncentrifuged amyloid stocks. Also protein therapeutic endostatin is tested for tPA activating properties. Concentrations of potential activators were 100 $\mu m l^{-1}$. Panel B: Binding of 32 $\mu m l^{-1}$ Hb-AGE to tPA and sRAGE in a Biacore surface plasmon resnonance experiment. Panel C: On the same chip relatively strong binding of 62.5 $\mu g\ ml^{-1}$ to tPA and sRAGE is observed. Panel D: More albumin-AGE, injected at 3.9 $\mu g\ ml^{-1}$, binds to tPA than to sRAGE. Panel E: By testing a concentration series of Hb-AGE for binding to a Biacore CM5 chip with immobilized Fn F4-5, it is deduced that half maximum binding is obtained with 8 nM Hb-AGE (indicated with the arrow). Panel F: As a control, 25 nM native Hb was tested for binding to a Biacore chip with immobilized Fn F4-5, Hepatocyte Growth Factor Antibody F (HGFA F) and tPA F. Panel G: By testing a concentration series of endostatin it is revealed that half maximum binding to Fn F4-5 is obtained with 800 nM endostatin (arrow). Panel H: Half maximum binding of recombinant β2GPI to immobilized Fn F4-5 is obtained with 165 nM β2GPI (arrow).

Our observations indicate that the presence of cross-β structures, or the potential that the cross-β structure conformation can be formed in these therapeutics, as well as those cross-β structures that may be present in all other protein therapeutics or constituents thereof is potentially harmful with respect to the induction of unwanted side-effects during treatment with the therapeutic. Such undesirable side effects include, but are not limited to thrombosis, bleeding, disseminated intravascular coagulation (DIC), septic shock, multi organ dysfunction syndrome (MODS), anaphylactic shock, an inflammatory reaction and/or the development of an adaptive immune response with antibodies against the drug and/or the endogenous protein. A person skilled in the art is now able to use a method included in the invention to determine the content of cross-β structure in any solution containing a protein, preferably a protein therapeutic, or a protein or protein therapeutic in solution that is being produced or stored during the production process of the protein or protein therapeutic. A person skilled in the art is also able to use a method of the invention to determine the content of cross-β structure in the circulation of a human or mammal suffering from any of the aforementioned diseases, preferably associated with the use of the protein therapeutic by a human or mammal. A person skilled in the art is now also able to deplete any cross-β structure comprising protein, preferably protein therapeutic from a solution. After depletion, using any of the methods included in the present invention, a person is able to determine the amount of cross-β structure that is being left in the solution. Moreover a person skilled in the art can determine the consequence of removal of the cross-β structure on any of the possible unwanted side effects, such as described above, that the protein comprising cross-β structure may induce. For example, a solution containing a protein therapeutic, preferably interferon α, factor VIII, erythropoietin, thrombopietin, glucagons, GH or Etanercept can be analyzed by any of the methods provided in the present invention. For experimental purpose, the protein therapeutic may be treated to induce an additional amount of cross-β structure to enhance the strength of the method. Treatment may comprise, but is not limited to heating, glycation, oxidation, acetylation. Subsequently, the solution can be depleted cross-β structure by a method of the invention. Subsequently, the effect of the method of depletion on the side effect, preferably immunogenicity, of the protein can be tested. Preferably, the effect on the generation of antibodies is determined. Preferably, the effect is being determined in serum obtained, after administration of the solution, before and after depletion, to a mouse, preferably a mouse transgenic for the protein or a human. Preferably, the determination is analyzed by an ELISA in which the protein is being immobilized on a microtiter plate. Subsequently, serial dilutions of serum are being added. Binding of antibodies is subsequently determined by standard procedures using preferably peroxidase-conjugated antibodies. Alternatively, the effect of the method can be analyzed in vitro. For example, the effect of the depletion method on the induction of inflammatory cytokines by cells, preferably cells of the innate immune system, preferably dendritic cells or macrophages. Preferably, the cytokine to be determined is TNFα. Preferably, the cytokine is determined by ELISA or rtPCR. Alternatively the effect of the method of depletion on the activation of inflammatory cells, preferably dendritic cells or macrophages can be tested by FACS analysis. Preferably, the levels of so-called co-stimulatory molecules, such as B7.1, B7.2, MHC class II, CD40 are determined on preferably CD11c positive cells. Alternatively any of the experiments described above or a modification thereof can be used as long as they are used to test an unwanted side effect of the cross-β structure comprising protein.

The invention is further explained in the examples, without being limited by them.

TABLE 1

| cross-β structure-binding compounds | | |
|---|---|---|
| Congo red<br>2-(4'-(methylamino)phenyl)-6-methylbenzothiaziole | Chrysamine G<br>Any other amyloid-binding dye/chemical | Thioflavin T<br>Glycosaminoglycans |
| Thioflavin S<br>Poly(thiophene acetic acid) | Styryl dyes<br>conjugated polyelectrolyte PTAA-Li | BTA-1 |

TABLE 2

| cross-β structure-binding protein | | |
|---|---|---|
| Tissue-type plasminogen activator | Finger domain(s) of tPA, factor XII, fibronectin, HGFA | Apolipoprotein E |
| Factor XII | Plasmin(ogen) | Matrix metalloprotease-1 |
| Fibronectin | 75 kD-neurotrophin receptor (p75NTR) | Matrix metalloprotease-2 |
| Hepatocyte growth factor activator | α2-macroglobulin | Matrix metalloprotease-3 |
| Serum amyloid P component | High molecular weight kininogen | Hybridoma antibody 2C11(F8A6)‡ |
| C1q | Cathepsin K | Hybridoma antibody 4A6(A7)‡ |
| CD36 | Matrix metalloprotease 9 | Hybridoma antibody 2E2(B3)‡ |
| Receptor for advanced glycation end-products | Haem oxygenase-1 | Hybridoma antibody 7H1(C6)‡ |
| Scavenger receptor-A | low-density lipoprotein receptor-related protein (LRP) | Hybridoma antibody 7H2(H2)‡ |
| Scavenger receptor-B | DnaK | Hybridoma antibody 7H9(B9)‡ |
| ER chaperone ERp57 | GroEL | Hybridoma antibody 8F2(G7)‡ |
| Calreticulin | VEGF165 | Hybridoma antibody 4F4‡ |
| Hybridoma conformational antibody WO1 | Hybridoma conformational antibody WO2 | Amyloid oligomer-specific antibody (ref.[5]) |
| formyl peptide receptor-like 1 | α(6)β(1)-integrin | CD47 |
| Rabbit anti-albumin-AGE antibody, Aβ-purified[a)] | CD40/CD40-ligand | apo A-I belonging to small high-density lipoproteins |
| apoJ/clusterin | 10 times molar excess PPACK, 10 mM εACA, (100 pM-500 nM) tPA[b)] | |

‡hybridoma antibodies developed in collaboration with the ABC-Hybridoma Facility, Utrecht University, Utrecht, the Netherlands.

a)Antigen albumin-AGE and ligand Aβ were send in to Davids Biotechnologie (Regensburg, Germany); a rabbit was immunized with albumin-AGE, antibodies against a structural epitope were affinity purified using a column with immobilized Aβ.

b)PPACK is Phe-Pro-Arg-chloromethylketone, εACA is ε-amino caproic acid, tPA is tissue-type plasminogen activator

TABLE 3

| Proteins involved in the "Cross-β structure pathway" | | |
|---|---|---|
| Hybridoma antibody 4B5 | Heat shock protein 27 | Heat shock protein 40 |
| Hybridoma antibody 3H7‡ | Nod2 (= CARD15) | Heat shock protein 70 |
| FEEL-1 | Pentraxin-3 | HDT1 |
| LOX-1 | Serum amyloid A proteins | GroES |
| MD2 | Stabilin-1 | Heat shock protein 90 |
| FEEL-2 | Stabilin-2 | CD36 and LIMPII analogous-I (CLA-1) |
| macrophage receptor with collagenous structure (MARCO) | LPS-binding protein | CD14 |
| C reactive protein | CD45 | Orosomucoid |
| Integrins | alpha-1 antitrypsin | apo A-IV-TTR complex |
| Albumin | Alpha-1 acid glycoprotein | β2-glycoprotein I |
| Lysozyme | lactoferrin | megalin |
| Tamm-Horsfall protein | Apolipoprotein E3 | Apolipoprotein E4 |
| Toll-like receptors | Complement receptor CD11b/CD18 (Mac-1, CR3) | integrin subunit alpha-d (subunit aD subunit b2, integrin CD11d/CD18 |
| CD11b2 | Leukocyte Function - Associated Antigen One (LFA-1; CD11a/CD18; or subunit alpha-L subunit β2 (subunit aLb2)) | intergrin (CR4; subunit alpha(x) subunit beta2, subunits aXb2; CD11c/CD18 |
| Von Willebrand factor | | |

‡hybridoma antibodies developed in collaboration with the ABC-Hybridoma Facility, Utrecht University, Utrecht, the Netherlands.

EXAMPLES

Materials and Methods

Preparation of Cross-β Structure Conformation Rich Compounds

For preparation of advanced glycation end-product (AGE)-modified bovine serum albumin, 100 mg $ml^{-1}$ of albumin was incubated with phosphate buffered saline pH 7.3 (PBS) containing 1 M of glucose-6-phosphate (g6p) and 0.05% m/v $NaN_3$, at 37° C. in the dark. Glycation was prolonged up to 23 weeks.[1] To prepare glycated hemoglobin (Hb-AGE), human hemoglobin (Hb, Sigma-Aldrich, H7379) at 5 mg $ml^{-1}$ was incubated for 32 weeks at 37° C. with PBS containing 1 M of g6p and 0.05% m/v of $NaN_3$. In control solutions, g6p was omitted. After incubations, solutions were extensively dialyzed against distilled $H_2O$ and, subsequently, stored at 4° C. Protein concentrations were determined with advanced protein-assay reagent ADV01 (Cytoskeleton, Denver, Colo., US). Glycation and formation of AGE was confirmed by measuring intrinsic fluorescent signals from AGE; excitation wavelength 380 nm, emission wavelength 435 nm. In addition, binding of AGE-specific antibodies was determined. Presence of cross-β structure conformation in albumin-AGE was confirmed by enhancement of Congo red fluorescence, enhancement of Thioflavin T (ThT) fluorescence, the presence of β-sheet secondary structure, as observed with circular dichroism spectropolarimetry (CD) analyses, and by X-ray fiber diffraction experiments.[1] Presence of cross-β structure conformation in Hb-AGE was confirmed by tPA binding, CD analyses, transmission electron microscopy (TEM) imaging of fibrillar structures and by Congo red fluorescence measurements. Amyloid preparations of human γ-globulins were made as follows. Lyophilized γ-globulins (G4386, Sigma-Aldrich) were dissolved in a 1(:)1 volume ratio of 1,1,1,3,3,3-hexafluoro-2-propanol and trifluoroacetic acid and subsequently dried under an air stream. Dried γ-globulins were dissolved in $H_2O$ to a final concentration of 1 mg $ml^{-1}$ and kept at room temperature for at least three days, or kept at 37° C. for three days and subsequently at −20° C. Aliquots were stored at −20° C. and analyzed for the presence of cross-β structure conformation. Fluorescence of Congo red and ThT was assessed. In addition tPA binding was analyzed in an ELISA and tPA activating properties in a chromogenic plasminogen (Plg) activation assay. In addition, the macroscopic appearance of denatured γ-globulins was analyzed with TEM imaging.

Human amyloid-β (AP) (1-40) Dutch type (DAEFRHDSGYEVHHQKLVFFAQDVGSNKGAIIGLMVGGVV) (SEQ ID NO:2) and human fibrin α-chain(148-160) amyloid fragment with Lys157Gly mutation (FP13, KRLEVDIDIGIRS) (SEQ ID NO:1) (BB, unpublished and [7]) were disaggregated in a 1:1 (v/v) mixture of 1,1,1,3,3,3-hexafluoro-2-isopropyl alcohol and trifluoroacetic acid, air-dried and dissolved in $H_2O$ (Aβ: 10 mg $ml^{-1}$, FP13: 2 mg $ml^{-1}$). After three days at 37° C., the peptide was kept at room temperature for two weeks, before storage at 4° C. Aβ solutions were tested for the presence of amyloid conformation by ThT or Congo red fluorescence and by TEM imaging. Negative control for cross-β structure detection assays was non-amyloid fragment FP10 of human fibrin α-chain(148-157) (KRLEVDIDIK) (SEQ ID NO:3).[7, 10] FP10 was dissolved at a concentration of 1 mg $ml^{-1}$ in $H_2O$ and stored at 4° C. This solution was used as a negative control for ThT fluorescence assays.

Cloning and Expression of Recombinant Fibronectin Type I Domains

F4-5 domains and the F domain of tPA with a carboxy-terminal $His_6$-tag were also expressed in *Saccharomyces cerevisiae*. The cDNA constructs were prepared following standard procedures known to a person skilled in the art, by the Biotechnology Application Center (BAC-Vlaardingen/Naarden, The Netherlands). Domain boundaries of Fn F4-5 and tPA F were taken from the human Fn and human tPA entries in the Swiss-Prot database (P02751 for Fn, P00750 for tPA) and comprised amino-acids $NH_2$-I182-V276-COOH of Fn F4-5 and $NH_2$-G33-S85-COOH of tPA. Affinity purification of the expressed proteins was performed using $His_6$-tag-$Ni^{2+}$ interaction and a desalting step. Constructs were stored at −20° C. in PBS pH 7.0. The molecular size of the constructs was checked on a Coomassie brilliant blue-stained SDS-PAGE gel.

Totally Chemical Synthesis of Fibronectin Type I Domains

Totally chemical synthesis of the F domains of hepatocyte growth factor activator (HGFA, SwissProt entry Q04756) and tPA (SwissProt entry P00750) was performed in the laboratory of Dr. T. M. Hackeng (Academic Hospital Maastricht, The Netherlands), according to standard procedures known to a person skilled in the art. Both domains were synthesized as two separate peptides that were subsequently ligated using native chemical ligation. The tPA F domain was completed with a carboxy-terminal acetylated lysine residue or biotinylated lysine residue. The HGFA F domain was supplied with an acetylated lysine residue. Products were analyzed on a reversed phase HPLC column and with mass spectrometry.

Cloning, Expression and Purification of the Soluble Extracellular Domains of Receptor for Advanced Glycation End-Products The soluble extracellular part, of the receptor for AGE (sRAGE) was cloned, expressed and purified as follows (Q.-H. Zeng, Prof. P. Gros, Dept. of Crystal- & Structural Chemistry, Bijvoet Center for Biomolecular Research, Utrecht University, Utrecht, the Netherlands). Human cDNA of RAGE was purchased from RZPD (clone IRALp962E1737Q2, RZPD, Berlin, Germany). For PCRs, the gagatctGCTCAAAACATCACAGCCCGG forward primer (SEQ ID NO:4) was used comprising a BglII site, and the gcggccgcCTCGCCTGGTTCGATGATGC reverse primer (SEQ ID NO:5) with a NotI site. The soluble extracellular part of RAGE comprises three domains spanning amino-acid residues 23-325. The PCR product was cloned into a pTT3 vector, containing an amino-terminal His-tag and a thrombin cleavage site. The sRAGE was expressed in 293E hamster embryonic kidney cells at the ABC-protein expression facility (Utrecht University, Utrecht, the Netherlands). Concentrated cell culture medium was applied to a Hi-trap Chelating HP $Ni^{2+}$-NTA column (Amersham Biosciences Europe, Roosendaal, The Netherlands). The running buffer was 25 mM Tris-HC1, 500 mM NaC1, pH 8.0. The protein was eluted by using a step gradient of 0 to 500 mM imidazole. Purity of the His-sRAGE was depicted from Coomassie stained SDS-PAGE gels. After concentration, the buffer was exchanged to 20 mM Tris-HC1, 200 mM NaCl, 100 μM phenylmethylsulfonyl fluoride (PMSF), pH 8.0. Various stocks at 1, 5 and 20 mg $m1^{-1}$ were first kept at 4° C. for several weeks and then stored at −20° C. In this way, the PMSF will be sufficiently inactivated at 4° C.

Plasminogen-Activation Assay and Factor XII Activation Assay

Plasmin (Pls) activity was assayed as described.[7] Peptides and proteins that were tested for their stimulatory ability were regularly used at 100 μg $ml^{-1}$. The tPA and plasminogen (Plg)

concentrations were 200 pM and 1.1 μM, respectively, unless stated differently. Chromogenic substrate S-2251 (Chromogenix, Instrumentation Laboratory SpA, Milano, Italy) was used to measure Pls activity. Conversion of zymogen factor XII (#233490, Calbiochem, EMD Biosciences, Inc., San Diego, Calif.) to proteolytically active factor XII (factor XIIa) was assayed by measurement of the conversion of chromogenic substrate Chromozym-PK (Roche Diagnostics, Almere, The Netherlands) by kallikrein. Chromozym-PK was used at a concentration of 0.3 mM. Factor XII, human plasma prekallikrein (#529583, Calbiochem) and human plasma cofactor high-molecular weight kininogen (#422686, Calbiochem) were used at concentrations of 1 μg $ml^{-1}$. The assay buffer contained HBS (10 mM HEPES, 4 mM KCl, 137 mM NaCl, 5 μM $ZnCl_2$, 0.1% m/v albumin (A7906, Sigma, St. Louis, Mo., USA), pH 7.2). Assays were performed using microtiter plates (Costar, Cambridge, Mass., USA). Peptides and proteins were tested for their ability to activate factor XII. 150 μg $ml^{-1}$ kaolin, an established activator of factor XII was used as positive control and solvent ($H_2O$) as negative control. The conversion of Chromozym-PK was recorded kinetically at 37° C. for at least 60 minutes. Assays were done in duplicate. In control wells factor XII was omitted from the assay solutions and no conversion of Chromozym-PK was detected. In some assays albumin was omitted from the reaction mixture. Alternatively, chromogenic substrate S-2222 (Chromogenix) was used to follow the activity of factor XII itself. With S-2222, activation of factor XII in plasma was measured, using 60% v/v plasma, diluted with substrate and $H_2O$ with or without potential cofactor. Furthermore, autoactivation of factor XII was measured by incubating 53 μg $ml^{-1}$ purified factor XII in 50 mM Tris-HCl buffer pH 7.5 with 1 mM EDTA and 0.001% v/v Triton-X100, with S-2222 and $H_2O$ with or without potential cofactor.

Surface Plasmon Resonance Studies

Binding of cross-β structure conformation containing peptides/proteins was studied using surface plasmon resonance technology with a Biacore 2000 apparatus (Biacore AB, Uppsala, Sweden). A standardized amine coupling procedure was used to couple proteins with F domains to a CM5 chip (Biacore AB, Uppsala, Sweden). First, the dextran surface of the chips was activated by a 35 μl injection with a 1:1 mixture of 0.1 M N-hydroxysuccinimide (NHS) and 0.4 M N-ethyl-N'-(dimethylaminopropyl)carbodiimide (EDC) at a flow rate of 5 μl $minute^{-1}$. Then, the proteins were covalently coupled to the activated dextran surface. Remaining activated groups in each of the four flow channels were blocked by injection of 35 μl of 1 M ethanolamine hydrochloride pH 8.5. EDC, NHS and ethanolamine hydrochloride were obtained from Biacore. On one chip, on channels 1 to 4, buffer (reference channel), the soluble extracellular part of receptor for advanced glycation end-products (sRAGE), tPA and K2P-tPA were immobilized. The immobilization buffer for the reference channel, channel 2 (sRAGE), channel 3 (tPA) and channel 4 (K2P-tPA) was 10 mM acetate pH 3.75. In channel 2, 2000 response units $(RU)_s$ RAGE was immobilized, 2700 RU and 2400 RU tPA and K2P-tPA are immobilized, respectively. The flow rate was 10 μl $minute^{-1}$, the injection time was 120 seconds. The running buffer during immobilization was 10 mM HEPES pH 7.4, 140 mM NaCl. Buffers were filtrated on a 0.22 μm filter (white GSWP, 47 mm, Millipore) and degassed at room temperature. For subsequent binding experiments, the running buffer was 10 mM HEPES pH 7.4, 140 mM NaCl, 1.5 mM $CaCl_2$, 10 mM εACA, 0.005% Tween-20. Binding of albumin-AGE was determined with a solution of 3.9 μg $ml^{-1}$ albumin-AGE in running buffer. Albumin-AGE was filtered on a Millex-GV 0.22 μm filter unit (Millipore). Binding of filtered Hb-AGE was tested at 32 μg $ml^{-1}$. Binding of amyloid γ-globulins were tested at 62.5 μg $ml^{-1}$. After each injection of protein, the chip was regenerated with 0.1 M $H_3P04$ pH 1.0. After injections with albumin-AGE and Hb-AGE this regeneration step was successful and sufficient, after injection with amyloid γ-globulins, the bound protein could not be released, not even after injection with more harsh regeneration buffers (HCl, NaOH). Binding of Hb-AGE was also tested after centrifugation for 10 minutes at 16,000*g alternative to filtration. tPA activation before and after filtration was assessed with a Plg-activation assay. Also amyloid γ-globulins and amyloid endostatin (EntreMed, Inc., Rockville, Md., USA) were tested before and after centrifugation.

On a second chip, buffer, chemically synthesized HGFA F domain, chemically synthesized tPA F domain and Fn F4-5-His6, expressed in *S. cerevisiae*, were immobilized. HGFA F was immobilized in 10 mM acetate buffer pH 4.0, 190 RU. tPA F was immobilized in 5 mM maleate pH 5.5, 395 RU, Fn F4-5 in 5 mM maleate pH 6.0, 1080 RU. Now, the running buffer was 10 mM HEPES pH 7.4, 140 mM NaCl, 1.5 mM $CaCl_2$, 10 mM εACA, 0.05% Tween-20. Regeneration buffer was running buffer supplemented with 1 M NaCl. Binding was tested with endostatin at 0-800 nM, Hb-AGE at 0-25 nM, recombinant $\beta_2$-glycoprotein I (β2GPI) at 0-300 mM and 25 nM native Hb. For the Fn F4-5 channel, the maximum binding expressed in RU was plotted against the concentrations.

For both chips, channel 1 was used for reference purposes. The signal obtained with this channel was subtracted from the signals obtained with the channels with immobilized proteins.

Thioflavin T Fluorescence

Fluorescence of ThT—protein/peptide adducts was measured as follows. Solutions of 25 μg $ml^{-1}$ of protein or peptide preparations were prepared in 50 mM glycine buffer pH 9.0 with 25 μM ThT. Fluorescence was measured at 485 nm upon excitation at 435 nm. Background signals from buffer, buffer with ThT and protein/peptide solution without ThT were subtracted from corresponding measurements with protein solution incubated with ThT. Regularly, fluorescence of Aβ was used as a positive control, and fluorescence of FP10, a non-amyloid fibrin fragment,[7] was used as a negative control. Fluorescence was measured in triplicate on a Hitachi F-4500 fluorescence spectrophotometer (Hitachi Ltd., Tokyo, Japan).

Congo Red Fluorescence

Solutions of 25 μg $ml^{-1}$ protein/peptide were incubated with 25 μM Congo red in PBS and fluorescence was measured at 590 nm upon excitation at 550 nm. Background signals from buffer, buffer with Congo red and protein/peptide solution without Congo red were subtracted from corresponding measurements with protein solution incubated with Congo red. Fluorescence was measured in triplicate on a Hitachi F-4500 fluorescence spectrophotometer.

Transmission Electron Microscopy Imaging

For TEM analysis of protein en peptide solutions grids were prepared according to standard procedures. Samples were applied to 100-mesh copper grids with carbon coated Formvar (Merck, Germany), and subsequently washed with PBS and $H_2O$. Grids were applied to droplets of 2% (m/v) methylcellulose with 0.4% (m/v) uranylacetate pH 4. After a two-minute incubation, grids were dried on a filter. Micrographs were recorded at 80 kV, at suitable magnifications on a JEM-1200EX electron microscope (JEOL, Japan).

Structural Analysis of Formulated Protein Therapeutics

Formulated protein therapeutics were obtained from the local hospital pharmacy and were used as supplied by the manufacturers. The following protein therapeutics were purchased: 1) human growth hormone (GH) (Genotropin, batch 52344B51, 5 mg ml$^{-1}$ KabiQuick, Pharmacia B.V., Woerden, The Netherlands), 2) recombinant human $Zn^{2+}$-chelated insulin (Monotard, batch NS61694, 100 IE ml$^{-1}$, Novo Nordisk, Bagsvaerd, Denmark), 3) human albumin (Cealb, batch NS61694, 200 mg ml$^{-1}$, Sanquin-CLB, Amsterdam, The Netherlands), 4) human-modified gelatin (Gelofusine, batch 030606H4, 40 mg ml$^{-1}$, Braun Medical BV, Oss, The Netherlands), 5) rapid acting human insulin analogue (NovoRapid Flexpen, batch PH70008, 10 U ml$^{-1}$, Novo Nordisk), 6) blood cell growth factor filgrastim (Neupogen Singleject, batch N0693AD, 960 μg ml$^{-1}$, Amgen Europe, Breda, The Netherlands), 7) human-murine chimeric monoclonal antibody (Remicade-infliximab, batch 03D06H120A, 10 mg ml$^{-1}$, Centocor, Leiden, The Netherlands), 8) abciximab, an inhibitor of blood platelet aggregation (ReoPro, 2 mg ml$^{-1}$, Centocor, Leiden, The Netherlands) and 9) human coagulation factor VIII (FVIII) isolated from healthy volunteers (Aafact, lot 02L046250A, 3.6 mg ml$^{-1}$, Sanquin-CLB, Amsterdam, The Netherlands). Lyophilized therapeutics were dissolved according to the manufacturers recommendations. GH, zinc-insulin, Cealb and gelatin were stored at −20, 4, room temperature, 37 and 65° C. Other protein therapeutics were only kept at 4° C., and assayed for the presence of cross-β structure conformation at shown time points. Enhancement in fluorescence of ThT and Congo red was measured with all formulated protein therapeutics. For this purpose, proteins were diluted to the indicated concentrations. In addition, tPA binding to the protein therapeutics was analyzed by ELISA and activation of tPA was tested using the Plg-activation assay. Zinc-insulin was diluted tenfold in the activation assay, GH was diluted to a final concentration of 500 μg ml$^{-1}$. Activation of factor XII and prekallikrein by the therapeutics was tested in the chromogenic factor XII assay (see above). For tPA ELISAs, 5 μg ml$^{-1}$ of the protein therapeutics were coated onto Greiner high-binding Microlon plates (#655092, Greiner Bio-One, Alphen a/d Rijn, The Netherlands). After coating, plates were blocked with Blocking Reagent (Roche Diagnostics, Almere, The Netherlands). A concentration series of tPA or K2P-tPA in PBS with 0.1% v/v Tween-20 and 10 mM ε-amino caproic acid was applied and the plates were incubated for one hour at room temperature with constant swirling. Binding of tPA was assessed with monoclonal antibody 374b that binds to the protease domain of both tPA and K2P-tPA (American Diagnostica, Tebu-Bio, The Netherlands), peroxidase-conjugated rabbit anti-mouse immunoglobulins (RAMPO, P0260, DAKOCytomation, Glostrup, Denmark), and stained with 3'3'5'5'-tetramethylbezidine (TMB, catalogue number 4501103, buffer, catalogue number 4501401, Biosource Int., Camarillo, Calif., US).

Activation of tPA by $\beta_2$-glycoprotein I, Binding of Factor XII and tPA to $\beta_2$-glycoprotein I, and ThT and TEM Analysis of $\beta_2$-Glycoprotein I Purification of $\beta_2$-glycoprotein I ($\beta_2$GPI) was performed according to established methods.[11, 12] Recombinant human β2GPI was made using insect cells and purified as described.[11] Plasma derived $\beta_2$GPI as used in a factor XII ELISA, the chromogenic Plg-activation assay and in the anti-phospholipid syndrome antibody ELISA (see below), was purified from fresh human plasma as described.[12] Alternatively, $\beta_2$GPI was purified from, either fresh human plasma, or frozen plasma (−20° C.) on an anti-$\beta_2$GPI antibody affinity column.[13]

Activation of tPA (Actilyse, Boehringer-Ingelheim) by $\beta_2$GPI preparations was tested in the Plg-activation assay (see above). Hundred μg ml$^{-1}$ plasma $\beta_2$GPI or recombinant $\beta_2$GPI were tested for their stimulatory cofactor activity in the tPA-mediated conversion of Plg to Pls, and were compared to the stimulatory activity of peptide FP13 (ref. [7]).

Binding of purified human factor XII from plasma (Calbiochem) or of purified recombinant human tPA to $\beta_2$GPI purified from human plasma, or to recombinant human $\beta_2$GPI was tested in an ELISA. Ten μg of factor XII or tPA in PBS was coated onto wells of a Costar 2595 ELISA plate (Cambridge, Mass., US) and incubated with concentration series of the two $\beta_2$GPI preparations. Binding of $\beta_2$GPI was assessed with monoclonal antibody 2B2.[13]

Binding of factor XII to β2GPI was also tested using immunoblotting. $\beta_2$GPI (33 μg) purified either from fresh plasma or from frozen plasma was brought onto a 7.5% SDS-PAGE gel. After blotting to a nitrocellulose membrane, the blot was incubated with 1000× diluted rabbit polyclonal anti-human factor XII antibody (#233504, Calbiochem) and after washing with 3000× diluted peroxidase-conjugated swine anti-rabbit immunoglobulins (SWARPO, #P0399, DAKOCytomation, Glostrup, Denmark).

ThT fluorescence of $\beta_2$GPI was measured as follows. Purified $\beta_2$GPI from human plasma (400 μg ml$^{-1}$ final concentration) was incubated with or without 100 μM cardiolipin (CL) vesicles or 250 μg ml$^{-1}$ of the factor XII activator dextran sulphate 500k (DXS500k, Pharmacia, Uppsala, Sweden), in 25 mM Tris-HCl, 150 mM NaCl, pH 7.3. CL vesicles were prepared according to an established procedure. Briefly, CL was dried under a stream of nitrogen. The lipids were resuspended to a concentration of 10 mg ml$^{-1}$ in 25 mM Tris-HCl, pH 7.3, 150 mM NaCl by vigorous agitation, using a vortex. In the ThT fluorescence assay, fluorescence of $\beta_2$GPI in buffer, of CL or DXS500k in buffer, of buffer and ThT alone, and of $\beta_2$GPI-CL adducts and $\beta_2$GPI-DXS500k adducts, with or without ThT, was recorded as described above (section ThT fluorescence). In addition, TEM images were recorded with CL, β2GPI from human plasma, with or without CL, and with recombinant β2GPI, as described.[1]

Interference with Binding of Anti-$\beta_2$GPI Autoantibodies from Antiphospholipid Syndrome Auto-Immune Patients to Immobilized $\beta_2$GPI by Recombinant $\beta_2$GPI and not by Plasma Derived $\beta_2$GPI When plasma derived $\beta_2$GPI is coated onto hydrophilic ELISA plates, anti-$\beta_2$GPI auto-antibodies isolated from plasma of antiphospholipid syndrome auto-immune patients can bind.[14] To study the influence of co-incubations of the coated $\beta_2$GPI with the antibodies together with plasma $\beta_2$GPI or recombinant $\beta_2$GPI, concentration series of $\beta_2$GPI were added to the patient antibodies. Subsequently, binding of the antibodies to coated $\beta_2$GPI was determined.

Activation of U937 Monocytic Cells by LPS and Cross-β Structure Conformation Comprising Polypeptides U937 monocytes were cultured in six-wells plates. Cells were stimulated with buffer (negative control), 1 μg ml$^{-1}$ LPS (positive control), 100 μg ml$^{-1}$ amyloid endostatin,[1, 7] 260 μg ml$^{-1}$ Hb-AGE and 260 μg ml$^{-1}$ control Hb. After one hour of stimulation, cells were put on ice. After washing RNA was isolated and quantified spectrophotometrically. Normalized amounts of RNA were used for 26 cycli of RT-PCR with human TNFα primer and 18 cycli of RT-PCR with ribosomal 18S primer for normalization purposes. DNA was analyzed on a 2% agarose gel.

Structural Analysis with CpG-ODN-Protein and LPS-Protein Mixtures

CpG oligodeoxynucleotides (ODN) (Coley Pharmaceutical Group, MA, USA) at a concentration of 10.7, 21.4 and 42.8 μg ml$^{-1}$ was incubated for 30 minutes at room temperature or o/n at 4° C., on a roller with 1 mg $ml^{-1}$ lysozyme or endostatin. Enhancement of ThT fluorescence was measured similarly as described above.

Alternatively, CpG-ODN at 21.4 μg $ml^{-1}$ was mixed with 1 mg $ml^{-1}$ of chicken egg-white lysozyme (Fluka, #62971), albumin (ICN, #160069, fraction V), endostatin (Entremed, Inc, Rockville, Md.), human γ-globulins, plasma human β2-GPI (see above) and recombinant human β2-GPI (see above), and incubated o/n on a roller at 4° C., before ThT fluorescence measurements. For this purpose, protein solutions at 2 mg $ml^{-1}$ were ultracentrifuged for one hour at 100,000*g before use, and subsequently diluted 1:1 in buffer with 42.9 μg $ml^{-1}$ CpG-ODN.

Lipopolysaccharide (LPS) binds to lysozyme, which can prevent biological activities of LPS, and LPS activates factor XII. We tested whether binding of lysozyme is accompanied by a conformational change in the protein with introduction of amyloid-like structure. For this purpose 0, 10, 25, 100, 200, 600 and 1200 μg $ml^{-1}$ LPS (from *Escherichia coli* serotype 011:B4, #L2630, lot 104K4109, Sigma-Aldrich) was incubated overnight at 4° C. or for 30 minutes at room temperature on a roller with 1 mg $ml^{-1}$ lysozyme (ICN, 100831) in HBS. Subsequently, the ability to enhance ThT fluorescence was determined with 40× diluted solution, as described above.

Alternatively, similarly as described above for CPG-ODN, LPS at 600 μg $ml^{-1}$ was mixed with 1 mg $ml^{-1}$ of lysozyme, albumin, endostatin, γ-globulins, plasma β2GPI and recombinant β2-GPI, and incubated o/n on a roller at 4° C., before ThT fluorescence measurements. Again, protein solutions at 2 mg $ml^{-1}$ were ultracentrifuged for one hour at 100,000*g before use, and subsequently diluted 1:1 in buffer with 1200 μg $ml^{-1}$ LPS.

Preparation of Amyloid-Like Ovalbuinin, Human Glucagon, Etanercept and Murine Serum Albumin To prepare structurally altered ovalbumin (OVA) with amyloid cross-β structure conformation, purified OVA (Sigma, A-7641, lot 071k7094) was heated to 85° C. One mg $ml^{-1}$ OVA in 67 mM $NaP_i$ buffer pH 7.0, 100 mM NaCl, was heated for two cycles in PCR cups in a PTC-200 thermal cycler (MJ Research, Inc., Waltham, Mass., USA). In each cycle, OVA was heated from 30 to 85° C. at a rate of 5° C./minute. Native OVA (nOVA) and heat-denatured OVA (dOVA) were tested in the ThT fluorescence assay and in the Plg-activation assay. In the fluorescence assay and in the Plg-activation assay, 25 and 100 μg $ml^{-1}$ nOVA and dOVA were tested, respectively. TEM images of nOVA and dOVA were taken to check for the presence of large aggregates.

Modified murine serum albumin (MSA) was obtained by reducing and alkylation. MSA (#126674, Calbiochem) was dissolved in 8 M urea, 100 mM Tris-HCl pH 8.2, at 10 mg $ml^{-1}$ final concentration. Dithiothreitol (DTT) was added to a final concentration of 10 mM. Air was replaced by $N_2$ and the solution was incubated for two hours at room temperature. Then, the solution was transferred to ice and iodoacetamide was added from a 1 M stock to a final concentration of 20 mM. After a 15-minute incubation on ice, reduced-alkylated MSA (alkyl-MSA) was diluted to 1 mg $ml^{-1}$ by adding $H_2O$. Alkyl-MSA was dialyzed against $H_2O$ before use. Native MSA (nMSA) and alkyl-MSA were tested in the ThT fluorescence assay and in the Plg-activation assay. In the ThT-fluorescence assay 25 μg $ml^{-1}$ nMSA and alkyl-MSA were tested, and in the Plg-activation assay 100 μg $ml^{-1}$ was tested. The presence of aggregates or fibrils was analyzed using TEM.

Amyloid-like properties in human glucagon (Glucagen, #PW60126, Novo Nordisk, Copenhagen, Denmark) were introduced as follows. Lyophilized sterile glucagon was dissolved at 1 mg $ml^{-1}$ in $H_2O$ with 10 mM HCl. The solution was subsequently kept at 37° C. for 24 hours, at 4° C. for 14 days and again at 37° C. for nine days. ThT fluorescence was determined as described above, and compared with freshly dissolved glucagon. tPA-activating properties of both heat-denatured glucagon and freshly dissolved glucagon was tested at 50 μg $ml^{-1}$. TEM analysis was performed to assess the presence of large multimeric structures.

Immunization of Balb/c Mice with Ovalbumin and Amyloid-Like Ovalbumin

Eight- to ten-week-old female Balb/c mice are immunized with OVA according to two immunization regimes (Central Animal Laboratories, Utrecht University, The Netherlands). Pre-immune serum was collected prior to the immunizations. In one regime two groups of five mice were subcutaneously injected five consecutive days per week, for three consecutive weeks. Doses comprised 10 μg native OVA or heat-denatured OVA for each injection. Alternatively, according to the second protocol, three groups of five mice were injected once intraperitoneally with doses comprising 5 μg nOVA, 5 μg OVA or 5 μg native OVA mixed 1:1 with complete Freund's adjuvant (CFA). Each week, blood was taken. After three weeks, a second dose was given. Incomplete Freund's adjuvant (IFA) was used instead of CFA. Blood was taken after one week after the start of the immunization. Antibody titers in sera were determined and sera were analyzed for the presence of cross-β structure conformation-specific antibodies. For this purpose, nOVA was coated onto wells of 96-well ELISA plates and incubated with dilution series of sera. Sera of the groups of five mice were pooled prior to the analyses. Plates were washed and subsequently incubated with peroxidase-conjugated rabbit anti-mouse immunoglobulins (RAMPO, P0260, DAKOCytomation, Glostrup, Denmark). Plates were subsequently developed with tetramethylbenzidine (TMB) substrate. The reaction was terminated with $H_2SO_4$.

Example 1

Protein Assemblies with Cross-β Structure Conformation Bind to Immobilized Fibronectin Type I Domains in a Biacore Surface Plasmon Resonance Set-Up We used a surface plasmon resonance set-up of Biacore to test whether immobilized proteins with affinity for cross-β structure conformation can capture amyloid-like polypeptides from solution under flow. This set up also allows testing of suitable elution buffers to disrupt the interaction. In this way insight into suitable methods to deplete proteins with cross-β structure conformation from solutions is obtained, as well as insight into how to compete for the interaction of cross-β structure conformation binders, which are, for example, immobilized on beads in a column, with proteins comprising cross-β structure conformation.

On one chip we immobilized sRAGE, tPA and K2P-tPA. One channel was left empty for reference purposes. Protein solutions were centrifuged for 10 minutes at 16,000*g before the solutions were applied to the Biacore chip. Centrifugation had no effect on the stimulatory effect of Hb-AGE and amyloid γ-globulins on tPA-mediated activation of Plg (FIG. 1, Panel A). Moreover, we filtrated all protein solutions before they were applied to the Biacore to exclude the presence of large aggregates with a density equal to buffer. For Hb-AGE similar response units were obtained after centrifugation or filtration (not shown). Subsequent experiments showed that Hb-AGE, albumin-AGE and amyloid γ-globulins bind to immobilized tPA and sRAGE (FIG. 1, Panels B-D). The interaction of tPA and sRAGE with Hb-AGE and albumin-AGE could be disrupted with 0.1 M $H_3PO_4$ buffer pH 1.0.

Amyloid γ-globulins, however, were not removed by this buffer. After trying several more harsh regeneration buffers, the binding capacity of the chip was lost.

On a second chip, chemically synthesized HGFA F and tPA F, and Fn F4-5-His expressed in *S. cerevisiae* were immobilized. None of the polypeptides with cross-β structure conformation bound to the two single F domain constructs. Hb-AGE, endostatin and recombinant β2GPI bound, however, to the Fn F4-5 doublet, whereas native Hb did hardly bind (FIG. 1, Panels E-H). Affinities of the three proteins for Fn F4-5, expressed as the concentration of ligand that results in half maximum binding, ranges from 8 nM for Hb-AGE, via 165 nM for recombinant β2GPI to up to 800 nM for endostatin. In fact, based on the absence of tPA activating properties in 100 $\mu g\ ml^{-1}$ endostatin (FIG. 1, Panel A), we did not expect any binding at all. Putatively, the surface plasmon resonance is more sensitive for the cross-β structure conformation under the conditions used. We observed that when a stock solution of endostatin at 7.9 $mg\ ml^{-1}$ in the buffer as supplied by the manufacturer, is kept at ice or at room temperature, readily aggregates. Perhaps, during the course of our experiments, part of the endostatin molecules start to denature, giving rise to the observed binding to Fn F4-5. With this chip, interaction between Fn F4-5 and the protein ligands could be abolished simply by increasing the NaCl concentration from 140 mM to 1 M. This shows that the interaction was primarily based on charge interactions.

Our surface plasmon resonance data show that F domains expressed in *S. cerevisiae* can bind to polypeptides with the cross-β structure conformation. Furthermore, the data show that both 0.1 M $H_3PO_4$ buffer pH 1.0 and 10 mM HEPES pH 7.4, 1 M NaCl, 1.5 mM $CaCl_2$, 10 mM εACA, 0.05% Tween-20 are suitable buffers to release polypeptides with cross-β structure conformation from cross-β structure-binding compounds. These buffers are also suitable to release cross-β structure-binding compounds and proteins that are bound to a ligand with cross-β structure conformation. These data are helpful during the design of a method to deplete solutions from cross-β structure conformation rich compounds by using cross-β structure-binding polypeptides that are immobilized on a suitable supporting material.

Activation of Factor XII and tPA by Protein Aggregates with Amyloid-Like Cross-β Structure Conformation Contacting factor XII to artificial negatively charged surfaces results in its activation, as measured by the conversion of prekallikrein to kallikrein, which can convert chromogenic substrate Chromozym-PK (FIG. 2). Now, we demonstrate that also peptide aggregates with cross-β structure conformation, the protein conformation found in amyloid, also stimulate factor XII activation (FIG. 2). Moreover, we demonstrate that kaolin is able to stimulate factor XII activation only when a protein cofactor, e.g., albumin or endostatin, is present at 1 $mg\ ml^{-1}$ in the assay buffer (FIG. 2, Panels C, D). Similar results were obtained when DXS500k surface was used as the factor XII activator; again DXS500k only activates factor XII when albumin or endostatin are added to the reaction mixture (FIG. 2, Panels E, F). Contacting DXS500k with various proteins, including lysozyme, γ-globulins, whole plasma and factor XII itself, results in the introduction of amyloid-like properties in the proteins, e.g., activation of tPA (FIG. 2, Panel G), enhanced fluorescence of ThT (FIG. 2, Panels H-J) and binding of tPA (FIG. 2, Panels K-N), indicative for the formation of cross-β structure conformation in the protein aggregates after exposure to the negatively charged surface. We also tested the ability of protein aggregates with cross-β structure conformation to induce auto-activation of factor XII. For this purpose, purified factor XII was incubated with substrate S-2222 and either buffer, or 1 $\mu g\ ml^{-1}$ DXS500k, 100 $\mu g\ ml^{-1}$ FP13 K157G, 10 $\mu g\ ml^{-1}$ Aβ(1-40) E22Q and 10 $\mu g\ ml^{-1}$ Hb-AGE. All three amyloid-like aggregates are able to induce factor XII auto-activation (FIG. 2, Panel P). FP13 K157G and Hb-AGE have a potency to induce auto-activation that was similar to the established surface activator DXS500k, whereas the potency of the Aβ(1-40) E22Q was somewhat lower. Freshly dissolved native Hb, ultracentrifuged for one hour at 100,000*g, and freshly dissolved FP13 K157G did not or hardly auto-activate factor XII (not shown).

Factor XII, tPA, Fn and their Recombinant Fn Type I, or Finger Domains Interact with Aggregates Comprising Cross-β Structure Conformation Like tPA, factor XII, Fn, tPA F domain, factor XII F domain and Fn F4-5 domains bind to peptide aggregates with cross-β structure conformation. In addition, the Fn F10-12 domains and the HGFA F domain bind to amyloid-like cross-β structure conformation rich aggregates (B. Bouma, data not shown). Moreover, like tPA,[1, 7] factor XII becomes activated by amyloid-like aggregates (FIG. 2). This has not only been established in an indirect way by measuring activated kallikrein from prekalikrein upon activation of factor XII, but also in a direct way by measuring auto-activation of factor XII upon exposure to amyloid-like protein aggregates (see FIG. 2, Panel O). Our data also show that several negatively charged surfaces, that are well known for their ability to activate factor XII, i.e., kaolin and DXS500k, need a protein cofactor to gain stimulatory capacities (FIG. 2, Panels C-F). Binding of ThT and tPA after exposure of proteins to DXS500k shows that the protein aggregate cofactors adopt the cross-β structure conformation, that are essential for both the factor XII activation and the tPA activation. In addition, our data show that recombinantly expressed F domains as well as totally chemical synthesized F domains can bind to polypeptides with cross-β structure conformation.

Our data show that both the fibrinolytic cascade and the contact system of blood coagulation become activated by activation of tPA and factor XII via protein aggregates with amyloid-like cross-β structure conformation. This predicts that presence of amyloid-like protein conformation in the circulation or elsewhere in the body is a risk factor for inducing pathological activation of the fibrinolytic cascade and/or the contact activation system. Indeed, we found elevated levels of activated FXII as well as elevated levels of plasmin-α2-antiplasmin (PAP) complexes in plasma obtained from patients suffering from systemic amyloidosis. Thus, it can be predicted that excessive systemic activation of the contact activation system and the fibrinolytic system by proteins comprising cross-β structure may also lead to undesirable complications, including, but not limited to thrombosis, bleeding, disseminated intravascular coagulation (DIC), septic shock, multi organ dysfunction syndrome (MODS) and/or anaphylactic shock. With the present invention it is now disclosed that such effects may be triggered by protein therapeutics or their constituents/excipients comprising cross-β structure or by protein therapeutics or their constituents/excipients that induce cross-β structure formation before, during or after administration into a subject.

Our data on factor XII activation open avenues that allow further analysis of the role of the cross-β structure conformation in factor XII activation. The influence of cross-β structure-binding proteins and compounds on the activation of factor XII in the presence of cross-β structure conformation can be studied. Our observation that both tPA and factor XII become activated by proteins that are contacted to DXS500k further show that the fibrinolytic cascade and the contact activation cascade of the haemostatic system are activated by a common mechanism, in which protein aggregates comprising amyloid-like cross-β structure conformation play an key role. Considering HGFA, similar cross-β structure-mediated activating mechanisms are predicted.

Our surface plasmon resonance data show that F domains expressed in *S. cerevisiae* can bind to polypeptides with the cross-β structure conformation. Furthermore, the data show that both 0.1 M $H_3PO_4$ buffer pH 1.0 and 10 mM HEPES pH 7.4, 1 M NaCl, 1.5 mM $CaCl_2$, 10 mM ϵACA, 0.05% Tween-20 are suitable buffers to release polypeptides with cross-β structure conformation from cross-β structure-binding compounds. These buffers are also suitable to release cross-β structure-binding compounds and proteins that are bound to a ligand with cross-β structure conformation. These data are helpful during the design of a method to deplete solutions from cross-β structure conformation rich compounds by using cross-β structure-binding polypeptides that are immobilized on a suitable supporting material.

Example 2

Formulated protein therapeutics for human use contain protein aggregates with cross-β structure conformation.

Structural Analysis of Formulated Protein Therapeutics

Formulated protein therapeutics for human use were obtained from the local hospital pharmacy. The therapeutics were analyzed for the presence of cross-β structure protein conformation. All analyses were performed before the expiring dates were reached. As controls, the therapeutics were stored as recommended by the manufacturers. Therapeutics were also stored at −20° C., room temperature, 37° C. and 65° C. Fluorescence of Congo red and ThT in the presence or absence of the therapeutics was analyzed, as well as tPA binding, tPA activation and factor XII activation. For fluorescence assays, 10 μg $ml^{-1}$ ΔP(1-40) E22Q amyloid was used as a positive control and gave typical values of approximately 1250 and 1800 A.U., respectively. Furthermore, TEM images were recorded to get insight whether amorphous aggregates are formed or fibrillar like structures. Gelatin, Cealb, FVIII and to some extent GH, stored at the recommended storage temperature of 4° C., enhanced the fluorescence of Congo red (FIG. 3, Panel A). In addition, Cealb, GH and FVIII enhance fluorescence of ThT (FIG. 3, Panel B). GH also induced tPA activation (FIG. 3, Panel C). Insulin activated tPA to a lesser extent, but still significantly (FIG. 3, Panel C). Both insulin and zinc-chelated insulin activate the factor XII/prekallikrein contact system (FIG. 3, Panel D). Gelatinous collagen fragments stored at 4° C. and 37° C. displayed enhanced Congo red fluorescence in a storage temperature dependent manner (FIG. 3, Panel E). Only gelatin kept at 37° C. activated factor XII (FIG. 3, Panel F). In an ELISA set-up, binding of tPA was established for Cealb, a therapeutic antibody, gelatin, zinc-chelated insulin (FIG. 3, Panel G) and GH (FIG. 3, Panel H), all stored at the recommended temperature of 4° C. For both ELISAs, Hb-AGE was coated as a positive control (not shown for clarity). In the ELISA depicted in FIG. 3, Panel G, truncated K2P-tPA, which lacks the amyloid-binding F domain, was also tested for binding to the immobilized protein therapeutics. K2P-tPA did not bind to any of the therapeutics tested (not shown). On TEM images various condensed aggregates are seen with modified gelatin (FIG. 3, Panel I). GH appeared on TEM images as linear, branched and condense particles, all apparently composed of spherical particles (FIG. 3, Panel J). Zinc-chelated insulin appears on TEM images as thin linear unbranched fibrils with varying length (FIG. 3, Panel K). FVIII and the antibody did not appear as visible particles under the electron microscope. Cealb and insulin appeared as visible aggregates with no sign of a fibrillar nature (FIG. 3, Panels L, M). Reopro displays storage temperature dependent ThT fluorescence enhancement properties and tPA activating properties (FIG. 3, Panels N, O). Only after storage at 65° C. ReoPro enhanced ThT fluorescence and induced Pls activity. Apparently, only at 65° C. ReoPro adopts the amyloid-like cross-β structure conformation. A TEM image of ReoPro that was stored at the recommended temperature of 4° C. revealed that some non-fibrillar aggregates were present, that apparently do not have ThT fluorescence enhancing or tPA activating properties under the conditions tested.

Discussion: Formulated Protein Therapeutics for Human Use Display Amyloid-Like Characteristics Based on the observed binding of Congo red, ThT and tPA, based on the appearance on TEM images, and based on the observed activating properties towards tPA and factor XII, the tested protein therapeutics Cealb, gelatin, insulin, zinc-insulin, GH, antibody and FVIII displayed amyloid-like properties, when stored under recommended conditions. For human Cealb, binding of tPA, Congo red and ThT is indicative for the presence of cross-β structure conformation. Binding of Congo red and activation of factor XII shows the presence of cross-β structure conformation in gelatin. Binding of ThT and tPA, and activation of tPA by GH are indicative for amyloid-like properties in this formulated therapeutic. Finally, both activation of tPA and factor XII by insulin/zinc-insulin show the presence of cross-β structure conformation. Hence, taken together our observations show the presence of protein or peptide aggregates with amyloid-like properties or the potential that the cross-β structure can be formed upon storage in these formulated protein therapeutics.

Structural analysis of protein therapeutics can be expanded using techniques and assays such as X-ray diffraction experiments, Fourier transform infrared spectroscopy, size exclusion HPLC, CD spectropolarimetry and binding assays using amyloid binding proteins, and can be expanded by introducing new protein therapeutics in the series of analyses.

Example 3

Cross-β Structure and Immunogenicity

Incubation of cultured U937 monocytes with proteins comprising cross-β structure conformation results in up-regulation of tissue necrosis factor-α mRNA levels, and the immunopotentiators LPS and CPG-ODN induce formation of amyloid-like structures in proteins.

Cross-β Structure Rich Compounds Induce Expression of TNFα RNA in Monocytes

Figure 4:
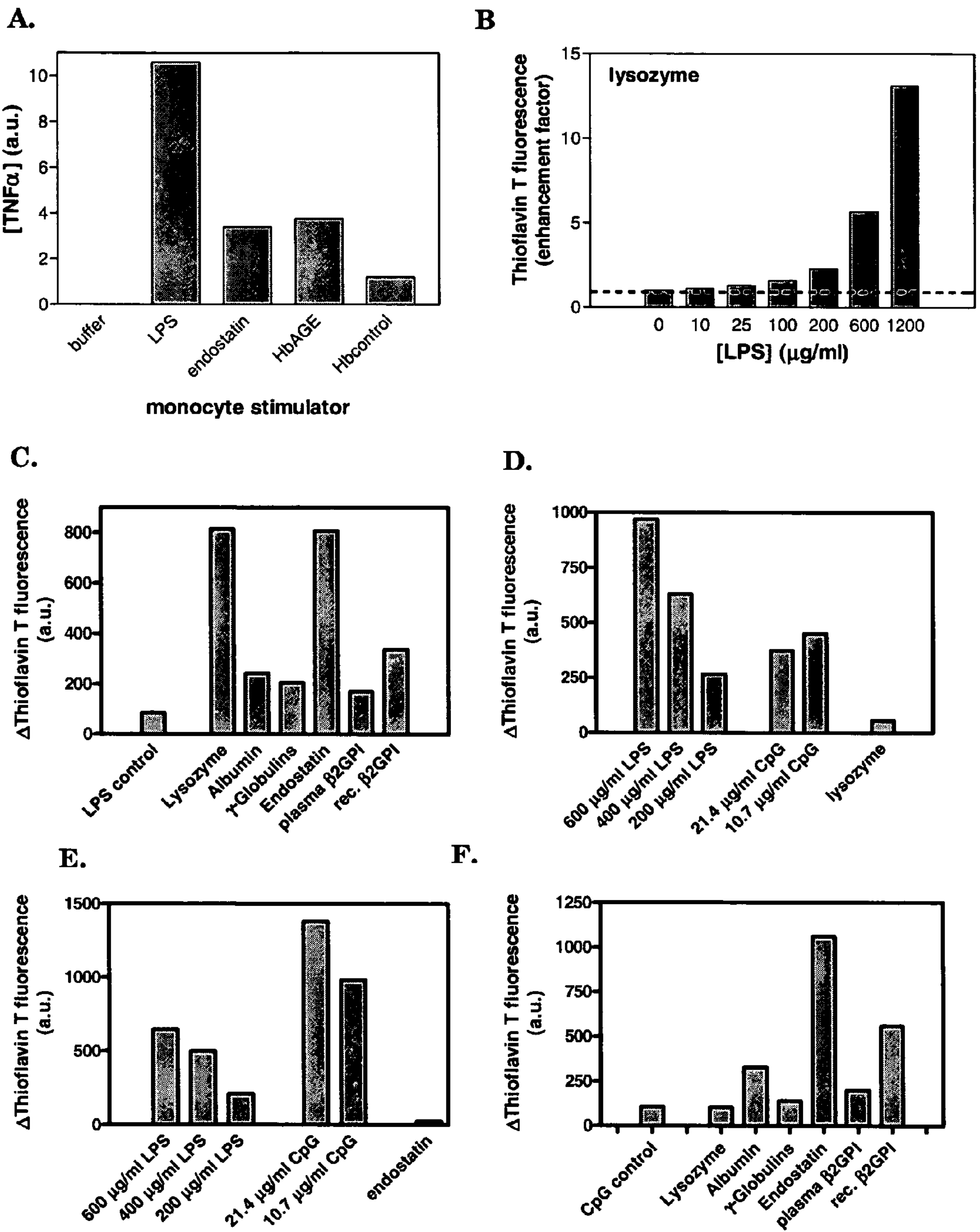
FIG. 4: Synthesis of TNFα RNA in monocytes after stimulation with cross-β structure conformation rich compounds and LPS, which acts as a denaturant. Panel A: Cultured U937 monocytes were incubated for one hour with buffer, LPS, amyloid endostatin, amyloid Hb-AGE or native Hb. Up-regulation of TNFα RNA was assessed by performing RT-PCR with RNA isolated form the monocytes and TNFα primers. Amounts of TNFα cDNA after RT-PCR were normalized for the amounts of ribosomal 18S cDNA, obtained with the same RNA samples. In monocytes incubated with buffer no TNFα RNA is detected. Endostatin and Hb-AGE induce approximately 30% of the TNFα RNA expression, when compared to LPS, whereas the TNFα RNA expression induced by native Hb is approximately threefold lower. Panel B: Exposure of 1 mg $ml^{-1}$ lysozyme to 0-1200 μg $ml^{-1}$ LPS results in a 1.1 up to a 13.1 fold increase of ThT fluorescence with respect to lysozyme incubated with buffer only, indicative for the denaturing capacity of LPS, resulting in amyloid-like structures in lysozyme. Standard deviations were typically less than 10% (not shown). Panel C: Exposure of 1 mg $ml^{-1}$ lysozyme, albumin, endostatin, γ-globulins, plasma β2GPI or rec. 132GPI to 600 μg $ml^{-1}$ LPS results in increased ThT fluorescence with approximately a factor 2 to 10. Panels D-F: Exposure of 1 mg $ml^{-1}$ lysozyme (Panel D) or endostatin (Panel E) to indicated concentration series of LPS or CPG-ODN induces an enhanced ThT fluorescence signal. Panel F: Exposure of 1 mg $ml^{-1}$ albumin, endostatin, plasma β2GPI or rec. β2GPI to 21.4 μg $ml^{-1}$ CPG-ODN results in increased ThT fluorescence with approximately a factor 2 to 10. With these assay conditions no effect is seen with lysozyme and γ-globulins.

After exposure of U937 monocytes to LPS or cross-β structure rich amyloid endostatin or Hb-AGE, TNFα DNA was obtained after RT-PCR with isolated RNA (FIG. 4, Panel A). Control Hb did induce TNFα RNA up-regulation only to a minor extent, which did not exceed approximately 30% of the values obtained after stimulation with amyloid endostatin or Hb-AGE. Amounts of TNFα DNA obtained after RT-PCR with monocyte RNA are normalized for the amounts of ribosomal 18S DNA present in the corresponding samples.

LPS and CPG-ODN Act as a Denaturants and Induces Cross-β Structure Conformation

After exposure of 1 mg $ml^{-1}$ lysozyme to 10, 25, 100, 200, 600 and 1200 μg $ml^{-1}$ LPS in solution, ThT fluorescence was enhanced 1.1, 1.3, 1.6, 2.3, 5.7 and 13.1 times respectively when compared to lysozyme incubated in buffer only, indicative for the formation of amyloid-like conformation with cross-β structure (FIG. 4, Panel B). After exposure of lysozyme and endostatin to 200, 400 and 600 μg ml-1 LPS, ThT fluorescence was enhanced approximately 5, 11 and 18 times and 8, 20 and 26 times, respectively (FIG. 4, Panels D, E). Similarly to what was observed with CPG-ODN (FIG. 4, Panel F), when 1 mg $ml^{-1}$ lysozyme, albumin, γ-globulins, endostatin, plasma β2GPI or recombinant β2GPI were exposed to 600 μg ml-1 LPS, ThT fluorescence was enhanced approximately 10, 3, 2, 10, 2 and 4 times, respectively (FIG. 4, Panel C). Furthermore, CPG-ODN at 10.7, 21.4 and 42.8 μg $ml^{-1}$ incubated overnight with 1 mg $ml^{-1}$ lysozyme enhanced ThT fluorescence with a factor 1.1, 1.2 and 1.4, respectively, further show the cross-β structure inducing capacity of CPG-ODN (not shown). In addition, when 10.4 or 21.7 μg $ml^{-1}$ CPG-ODN was incubated with 1 mg $ml^{-1}$ lysozyme or endostatin for 30 minutes at room temperature, an increase in ThT fluorescence of approximately 8 to 7 times for lysozyme and 39 to 56 times for endostatin was observed, respectively (FIG. 4, Panels D, E). In addition, exposure of 1 mg $ml^{-1}$ albumin, endostatin, plasma β2GPI or rec. β2GPI to 21.4 μg $ml^{-1}$CPG-ODN results in increased ThT fluorescence with approximately a factor 3, 10, 2 and 5, respectively (FIG. 4, Panel F). Additional TEM imaging could shed further light on whether the LPS and CPG-ODN exposed proteins have rearranged their conformation into amyloid like fibrils or into other visible aggregates. The ThT fluorescence enhancement data show that LPS and CPG-ODN act as denaturants that convert initially globular proteins into an amyloid-like polypeptide. Previously, it has already been demonstrated that lysozyme can bind to purified LPS and to complete Freund's adjuvant, comprising bacterial cell wall fragments with LPS, accompanied by structural changes in the protein.[15, 16] Furthermore, Morrison & Cochrane[17] showed that LPS can potently activate factor XII, which adds to our finding that LPS acts as compound capable of inducing cross-β structure, which in turn is responsible for the activation of factor XII. Thus, our results now disclose that LPS binding induces cross-β structure conformation and that LPS activation of factor XII is mediated by protein with cross-β structure conformation, providing an explanation for these previously reported observations.

Similar to LPS, Cross-β Structure Rich Proteins Induce TNFα Up-Regulation in Monocytes, and LPS Induces Amyloid Cross-β Structure Conformation in Lysozyme Stimulation of U937 monocytes with proteins that comprise cross-β structure conformation as part of their tertiary/quaternary fold results in expression of TNFα RNA, similar to the up-regulation of TNFα RNA by LPS. The observation that control Hb did influence TNFα RNA levels only to some extent shows that the presence of cross-β structure conformation is an important factor for the observed up-regulation. Since we here show that LPS acts as a cross-β structure conformation-inducing agent we conclude that the activation of cells, including cells of the immune system, by LPS is induced, at least in part, by a conformationally altered protein comprising cross-β structure conformation. Thus, LPS acts as a denaturing surface or adjuvant that induces cross-β structure conformation formation in a protein that is present on the cell surface or in the cell environment, similar to our observation that LPS introduces amyloid-like cross-β structure conformation in lysozyme. The formed cross-β structure conformation is then a stimulator of the immune response. Our results and conclusions are supported by the observations in literature that the endotoxic activity of LPS is enhanced in the presence of albumin or Hb. Moreover, LPS induces formation of β-sheets in albumin, a structural element that is absent in the albumin native fold and which suggests that cross-β structure conformation is formed.[18] Similar responses of microglial cells towards LPS and aggregated Aβ are reported.[19] Our observations give a rationale to these and recent additional observations that the LPS receptor CD14 is involved in Aβ phagocytosis.[20, 21] In the light of our results CD14 perhaps interacts with a denatured protein associated with LPS and with Aβ via a similar non-native protein conformation in the ligands. This would suggest that CD14 is a possible member of the class of amyloid-like cross-β structure-binding proteins.[1] Blocking experiments using cross-β structure-binding compounds and proteins, e.g., ThT, Congo red, Thioflavin S (ThS), tPA and fragments thereof, factor XII and fragments thereof, anti-cross-β structure hybridomas, can provide further evidence for the role of the cross-β structure element in the activation of the immune system. Furthermore, cellular assays can be used to study which appearance of the cross-β structure conformation bears the immunogenic nature, i.e., soluble oligomers, fibrils, or other appearances.

Our results show that the potentiating effects of LPS, when it is used as an adjuvant in immunization experiments, are attributed at least in part by the introduction of immunogenic cross-β structure conformation in the administered antigen, in a co-administered or in an endogenous protein or set of endogenous proteins.

A person skilled in the art can now further assess whether a protein with cross-β structure conformation is activating cells of the immune system is by use of a "whole blood" assay. For this purpose, at day 1 freshly drawn human EDTA-blood should be added in a 1:1 ratio to RPMI-1640 medium (HEPES buffered, with L-glutamine, Gibco, Invitrogen, Breda, The Netherlands), that is pre-warmed at 37° C. Subsequently, proteins comprising cross-β structure conformation can be added. Preferably, a positive control is included, preferably LPS. An inhibitor that can be used for LPS is Polymyxin B at a final concentration of 5 μg $ml^{-1}$. Standard cross-β structure conformation rich polypeptides that can be tested are Aβ, amyloid γ-globulins, glycated proteins, FP13, heat-denatured OVA and others. Negative controls are native γ-globulins, native albumin, native Hb, freshly dissolved Aβ or FP13, nOVA. As a control, all protein samples can be tested in the absence or presence of 5 μg $ml^{-1}$ Polymyxin B to exclude effects seen due to endotoxin contaminations. The blood and the medium should be mixed carefully and incubated overnight in a $CO_2$ incubator with lids that allow for the entrance of $CO_2$. At day 2, the medium should be collected after 10 minutes centrifugation at 1,000*g, at room temperature. The cell pellet can be frozen and stored. The medium should be again be centrifuged for 20 minutes at 2,000*g, at room temperature. Supernatant can be analyzed using ELISAs for concentrations of markers of an immune response, e.g., tissue necrosis factor-α (TNF-α) or cytokine. When positive and negative controls are established as well as a reliable titration curve, any solution can be tested for the cross-β structure load with respect to concentrations of markers for immunogenicity. Furthermore, putative inhibitors of the immune response can be tested. For example, F domains, ThT, Congo red, sRAGE and tPA may prevent an immune response upon addition to protein therapeutic solutions comprising aggregates.

Alternatively the effect of proteins comprising cross-β structure on the induction of inflammatory cytokines, including but not limited to TNFα, are tested using cultured cells in vitro. For example, monocytic cells such as U937 or THP-1 monocytes care used stimulated with proteins comprising cross-β structure. ELISAs are used to determine the release of cytokines by these cells. Alternatively, RT-PCR is used.

Example 4

Relationship Between the Structure of $\beta_2$-glycoprotein I, the Key Antigen in Patients with the Antiphospholipid Syndrome, and Antigenicity.

The Anti-Phospholipid Syndrome and Conformationally Altered $\beta_2$-glycoprotein I The anti-phospholipid syndrome (APS) is an autoimmune disease characterized by the presence of anti-$\beta_2$-glycoprotein I autoantibodies. Two of the major clinical concerns of the APS are the propensity of autoantibodies to induce thrombosis and the risk for fetal resorption. Little is known about the onset of the autoimmune disease. Recent work has demonstrated the need for conformational alterations in the main antigen in APS, $\beta_2$-glycoprotein I ($\beta_2$GPI), before the initially hidden epitope for autoantibodies is exposed.[22] Binding of native $\beta_2$GPI to certain types of ELISA plates mimics the exposure of the cryptic epitopes that are apparently present in APS patients.[22] It has been demonstrated that anti-$\beta_2$GPI autoantibodies do not bind to globular $\beta_2$GPI in solution, but only when $\beta_2$GPI has been immobilized to certain types of ELISA plates.[22] The globular (native) form of the protein is not immunogenic, but requires the addition of CL, apoptotic cells or modification by oxidation.[9] Thus the generation of autoantibodies seems to be triggered by and elicited against a conformationally altered form of $\beta_2$GPI. It has previously been proposed that the induction of an adaptive immune response requires a so-called "danger" signal, which among other effects stimulates antigen presentation and cytokine release by dendritic cells.[23] The following results imply that CL induces cross-β structure conformation in β2GPI which than serves as a danger signal. In analogy other negatively charged phospholipids, or structures that contain negatively charged lipids, such as liposomes or apoptotic cells, or other inducers of cross-β structure conformation, including LPS, CPG-ODN that possess cross-β structure conformation inducing properties, may be immunogenic due to the fact, at least in part, that they induce cross-β structure conformation.

Factor XII and tPA Bind to Recombinant $\beta_2$GPI and to $\beta_2$GPI Purified from Frozen Plasma, but not to $\beta_2$GPI Purified from Fresh Plasma Recombinant $\beta_2$GPI, but not $\beta_2$GPI purified from fresh plasma stimulate tPA-mediated conversion of Plg to Pls, as measured as the conversion of the Pls-specific chromogenic substrate S-2251 (FIG. 5, Panel A). Using an ELISA it is shown that tPA and factor XII bind recombinant $\beta_2$GPI, but not bind to $\beta_2$GPI purified from fresh human plasma (FIG. 5, Panels B, C). Recombinant $\beta_2$GPI binds to factor XII with a $k_D$ of 20 nM (FIG. 5, Panel C) and to tPA with a $k_D$ of 51 nM (FIG. 5, Panel B). In addition, $\beta_2$GPI purified from plasma that was frozen at −20° C. and subsequently thawed, factor XII co-elutes from the anti-$\beta_2$GPI antibody affinity column, as shown on Western blot after incubation of the blot with anti-factor XII antibody (FIG. 5, Panel D). This suggests that $\beta_2$GPI refolds into a conformation containing cross-β structure upon freezing. In FIG. 5, Panel E, the inhibitory effect of recombinant $\beta_2$GPI on binding of anti-$\beta_2$GPI autoantibodies isolated from patients with APS to immobilized $\beta_2$GPI is shown. It is seen that plasma derived $\beta_2$GPI in solution has hardly an effect on the antibody binding to immobilized $\beta_2$GPI. FIG. 5, Panel F shows that exposure of $\beta_2$GPI to CL or DXS500k introduces an increased ThT fluorescence signal, indicative for a conformational change in $\beta_2$GPI accompanied with the formation of cross-β structure conformation. Again, recombinant $\beta_2$GPI initially already gave a higher ThT fluorescence signal than native $\beta_2$GPI purified from plasma. In addition, exposure of plasma β2GPI and rec. β2GPI to adjuvants/denaturants LPS or CPG-ODN also induces an increase in ThT fluorescence, which is larger with rec. β2GPI than with plasma β2GPI for both adjuvants (see examples in patent P71713EP00). These data not only show that recombinant β2GPI already comprises more cross-β structure conformation than plasma β2GPI, but that recombinant β2GPI also adopts more readily this conformation when contacted to various adjuvants and surfaces, i.e., CL, DXS500k, LPS and CPG-ODN. In FIG. 5, Panel G it is shown that exposure of $\beta_2$GPI to CL, immobilized on the wells of an ELISA plate, renders $\beta_2$GPI with tPA binding capacity. Binding of $\beta_2$GPI directly to the ELISA plate results in less tPA binding. These observations also show that CL has a denaturing effect, thereby inducing amyloid-like conformation in $\beta_2$GPI, necessary for tPA binding. These observations, together with the observation that exposure of $\beta_2$GPI to CL vesicles induced ThT binding capacity (FIG. 5, Panel F), show that exposure of $\beta_2$GPI to a denaturing surface induces formation of amyloid-like cross-β structure conformation.

Epitopes for Autoantibodies are Specifically Exposed on Non-Native Conformations of $\beta_2$GPI Comprising Cross-β Structure Conformation FIG. 5 shows that preparations of $\beta_2$GPI react with amyloid cross-β structure markers ThT, tPA and factor XII. In addition, exposure of $\beta_2$GPI to CL introduces tPA binding capacity (FIG. 5, Panel G). Furthermore, large fibrillar structures are seen on TEM images of plasma $\beta_2$GPI in contact with CL (FIG. 5, Panel H, image 2 and 3). Small CL vesicles seem to be attached to the fibrillar β2GPI. Images of plasma $\beta_2$GPI alone (FIG. 5, Panel H, image 1) or CL alone (not shown) revealed that no visible ultrastructures are present. In contrast, non-fibrillar aggregates and relatively thin curly fibrils can be seen on images of recombinant $\beta_2$GPI (FIG. 5, Panel H, image 4). These observation show that exposure of $\beta_2$GPI to CL and expression and purification of recombinant $\beta_2$GPI result in an altered multimeric structure of $\beta_2$GPI, when compared to the monomeric structure observed with X-ray crystallography.[24] The $\beta_2$GPI preparations with cross-β structure conformation express epitopes that are recognized by anti-$\beta_2$GPI auto-antibodies isolated from APS patient plasma. Furthermore, exposure of $\beta_2$GPI to CL or DXS500k induces an increased fluorescence when ThT is added, indicative for the formation of cross-β structure conformation when $\beta_2$GPI contacts a negatively charged surface. Interestingly, it has previously been observed that exposure of $\beta_2$GPI to CL is a prerequisite for the detection of anti-$\beta_2$GPI antibodies in sera of immunized mice.[9] These combined observations point to a role for conformational changes in native $\beta_2$GPI, necessary to expose new immunogenic sites. Our results show that the cross-β structure conformation is part of this epitope. We predict that the cross-β structure conformation can be relatively easily formed by one or more of the five domains of the extended $\beta_2$GPI molecule.[24] Each domain comprises at least one β-sheet that may function as a seed for local refolding into cross-β structure conformation.

A person skilled in the art is now able to test the hypothesis that the cross-β structure conformation is essential to elicit anti-$\beta_2$GPI antibodies. Immunization studies with native $\beta_2$GPI and conformationally altered $\beta_2$GPI, with or without cross-β structure conformation, can be performed in the presence or absence of a compound, including ThT, tPA, RAGE, CD36, anti-cross-β structure antibodies or a functional equivalent thereof, that inhibits the activity of cross-β structure conformation. Alternatively, in vitro studies with antigen presenting cells (APC), including dendritic cells (DC) can be performed. Sources of conformationally altered $\beta_2$GPI are recombinant $\beta_2$GPI, or $\beta_2$GPI exposed to any denaturing surface, e.g., plastics, CL, DXS500k and potentially other adjuvants. In addition, structurally altered $\beta_2$GPI may be obtained by any other chemical or physical treatment, e.g., heating, pH changes, reduction-alkylation. A person skilled in the art is able to design and perform in vitro cellular assays and in vivo mouse models to obtain further evidence for the role of the cross-β structure conformation in autoimmunity (see below). To establish whether the cross-β structure element is essential for eliciting an immune response or for antibody binding, inhibition studies can be conducted with any cross-β structure-binding compound that may compete with antibody binding or that may prevent an immune response.

Our observations show that cross-β structure conformation is necessary for the induction of an adaptive immune response. The cross-β structure conformation can also be part of an epitope recognized by autoimmune antibodies. Based on our studies it is expected that other diseases and complications in which autoantibodies are implicated are mediated by a protein comprising cross-β structure conformation. In addition to the antiphospholipid syndrome such conditions include, but are not limited to systemic lupus erythematosus (SLE), type I diabetes, red cell aplasia and the formation of inhibitory antibodies in hemophilia patients treated with FVIII. A person skilled in the art is now able to screen hemophilia patients with anti-FVIII autoantibodies for the presence of antibodies in their plasma that recognize the cross-β structure conformation. A more detailed analysis will reveal whether putative cross-β structure-binding antibodies specifically bind (in part) to cross-β structure conformation in the antigen, or whether the antibodies bind to cross-β structure conformation present in any unrelated protein.

A role for the cross-β structure element in immunological reactions upon administering protein therapeutics with cross-β structure conformation can be addressed by a person skilled in the art (see below). Moreover, a person skilled in the art can test, for example, the immunogenicity of a protein therapeutic, including but not limited to FVIII comprising cross-β structure conformation before and after contacting the protein therapeutic solution with immobilized cross-β structure-binding compounds or proteins to remove proteins comprising cross-β structure. After such contacting, the decreased amount of cross-β structure conformation is determined and in vivo or in vitro experiments is used to determine the effect of the removal of cross-β structure conformation (see also below).

Example 5

Immunogenicity of Denatured Proteins with Amyloid Cross-β Structure Conformation without the Use of an Adjuvant.

Preparation of Antigens with Cross-β Structure Conformation

Figure 6:
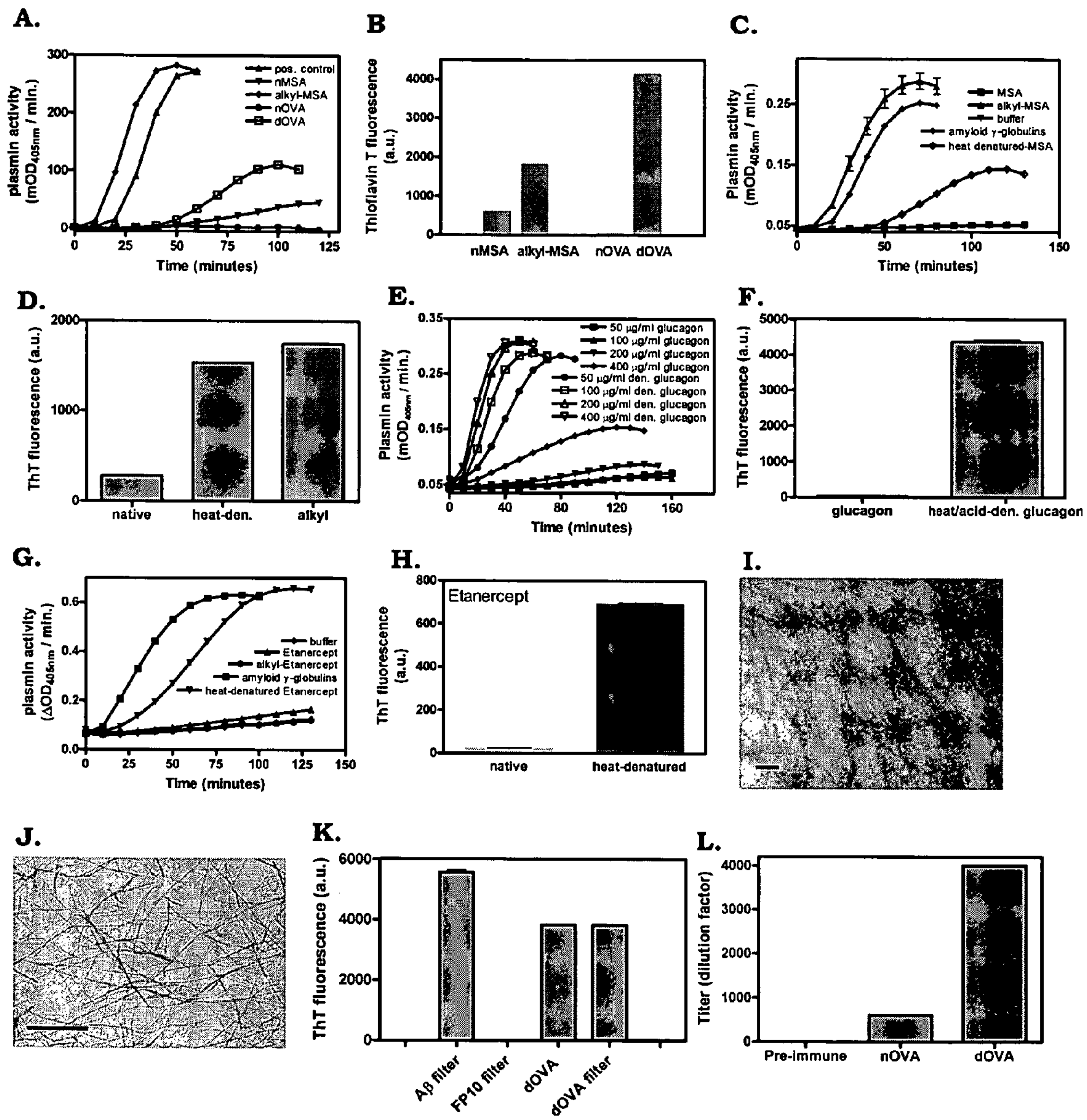
FIG. 6: Amyloid-like cross-β structure conformation in alkylated murine serum albumin and in heat-denatured ovalbumin, murine serum albumin, human glucagon and Etanercept and immogenicity of ovalbumin. Panel A: Plg-activation assay with Pls activity read-out using chromogenic substrate S-2251. Activating properties of reduced and alkylated MSA (alkyl-MSA) and heat-denatured OVA (dOVA) are compared with amyloid γ-globulins (positive control), buffer (negative control), and native MSA (nMSA) and OVA (nMSA, nOVA). Panel B: ThT fluorescence assay with native and denatured MSA and OVA. Panel C: TPA activation assay for comparison of reduced and alkylated MSA and heat-denatured MSA. Panel D: ThT fluorescence assay with reduced/alkylated MSA and heat-denatured MSA. Panel E: tPA activation assay with concentration series of heat/acid denatured glucagon. Panel F: ThT fluorescence assay with native and heat/acid denatured glucagon. Panel G: Comparison of the tPA activating properties of heat-denatured Etanercept, native Etanercept and reduced/alkylated Etanercept. Panel H: ThT fluorescence of native and heat-denatured Etanercept. Panel I: TEM image of dOVA. The scale bar represents 200 nm. Panel J: TEM image of heat/acid-denatured glucagon. The scale bar represents 1 μM. Panel K: ThT fluorescence assay showing that filtration through a 0.2 μm filter of denatured OVA does not influence the fluorescence enhancing properties. Panel L: Titer determination of anti-nOVA antibodies in pooled sera of mice immunized with nOVA or dOVA. Titer is defined as the sera dilution that still gives a signal above the background value obtained with 10 times diluted pre-immune serum.

The data disclosed in Example 2, showing that in various protein therapeutics signs for the presence of cross-β structure conformation can be gathered, and the data disclosed in Examples 2 and 4 of patent application P71713EP00, showing that various adjuvants used in animal and human vaccination regimes induce the cross-β structure conformation in proteins show that immunogenicity is attributed, at least in part, to cross-β structure comprising proteins or polypeptides. This prompted us to set up immunization trials with cross-β structure conformation rich compounds, without addition of an adjuvant. Based on the results described above it is predicted that the presence of the immunogenic cross-β structure conformation is essential and even sufficient to induce an immune response, such as, for example, seen with various protein-based pharmaceuticals that lack an adjuvant. Indeed higher antibody titers were obtained when we used chicken OVA with cross-β structure conformation (dOVA) in comparison with OVA without cross-β structure conformation (nOVA) in immunization experiments (FIG. 6, Panel L). Titers were also obtained with OVA without cross-β structure conformation. Since the formation of cross-β structure in OVA can readily occur it is predicted that the generation of antibodies after immunization with nOVA is also mediated by molecules with cross-β structure conformation. In this case the cross-β structure conformation is induced during or after the subcutaneous injection. A person skilled in the art can perform similar experiments with any protein or set of proteins, for example MSA, but preferably protein therapeutics, preferably with interferon α, glucagon or Etanercept to further obtain evidence for the role of the cross-β structure in immunogenicity of proteins, preferably protein therapeutics or constituents thereof. Preferably, the cross-β structure conformation is induced by heating (see below), oxidation (see below), glycation or treatment with an adjuvant, such as CPG-ODN oligodeoxynucleotides, LPS or CL. The content of cross-β structure conformation is preferably measured by ThT, Congo red, TEM, size exclusion chromatography, tPA-activating activity, and or binding of any other cross-β structure-binding protein listed in Tables 1-3. For example, native and modified, preferably oxidized, forms of a protein therapeutic, preferably interferon a should be tested. Preferably, different amounts of the native and modified therapeutic should be mixed and used for immunization. Preferably, mice are used for immunization and even more preferably, mice transgenic for the therapeutic. These experiments will further establish that the presence of the cross-β structure conformation in a protein can induce immunogenicity. In the case of a protein therapeutic, removing or diminishing the cross-β structure content of the therapeutic will aid to a safer medicine.

Amyloid-like OVA was obtained by heat denaturation at 85° C. (FIG. 6, Panels A, B, I, K). The presence of the cross-β structure conformation was established with ThT fluorescence and Plg-activation assays and by TEM imaging. The fibrillar structures of at least up to 2 μm in length, seen on the TEM images are likely not the only OVA assemblies with cross-β structure conformation present, as concluded from the observation that filtration through a 0.2 μm filter does not reduce the enhancement of ThT fluorescence. A person skilled in the art can perform similar experiments with MSA, human glucagon and Etanercept stock solutions with the cross-β structure conformation, such as those described below (FIG. 6).

The amyloid-like protein fold was induced in MSA by heat denaturation at 85° C. and by reduction and alkylation of disulphide bonds (FIG. 6, Panels A-D). We observed that also native MSA enhanced ThT fluorescence to some extent, but this was not reflected by stimulation of tPA activation. Although heat-denatured MSA and alkylated MSA enhance ThT fluorescence to a similar extent, they differ in tPA activating potential. This suggests that tPA and ThT interact with distinct aspects of the cross-β structure conformation. Previously, we observed that Congo red, another amyloid-specific dye, can efficiently compete for tPA binding to amyloid-like aggregates in ELISAs, whereas ThT did not inhibit tPA binding at all (patent application P57716EP00 and B. Bouma, unpublished data).

Amyloid-like cross-β structure conformation was induced in glucagon by heat-denaturation at 37° C. at low pH in HCl buffer (FIG. 6, Panels E, F, J). In this way, a potent activator of tPA was obtained, that enhanced ThT fluorescence to a large extent. In addition, long and bended unbranched fibrils are formed, as visualized on TEM images (FIG. 6, Panel J). Noteworthy, at high glucagon concentration, also native glucagon has some tPA activating potential, indicative for the presence of a certain amount of cross-β structure conformation rich protein.

Alkylated Etanercept does not activate tPA at all, whereas heat-denatured Etanercept has similar tPA activating potential as amyloid γ-globulins (FIG. 6, Panel G). After heat denaturation, Etanercept also efficiently induces enhanced ThT fluorescence (FIG. 6, Panel H). Native Etanercept both induces some tPA activation and gave some ThT fluorescence enhancement.

For immunizations of Balb/c mice, nOVA, dOVA and nOVA with complete Freund's adjuvant were used. Similar immunizations and analyzes can be performed with n-MSA, heat-denatured MSA, alkyl-MSA, native glucagon, heat-denatured glucagon, native Etanercept, denatured Etanercept, native β2GPI, alkyl-β2GPI, denatured β2GPI, recombinant β2GPI, β2GPI together with CPG-ODN, β2GPI together with CL and β2GPI together with DXS500k. Furthermore, the analysis of the various titers may point to improved immunization protocols with respect to dose, number of injections, way of injection, pre-treatment of the antigen to introduce more immunogenic cross-β structure conformation.

For example, 25 μg Etanercept, heat-denatured Etanercept, glucagon and heat/acid-denatured glucagon will be administered subcutaneously without adjuvant at day 0 and at day 18. Blood for titer determinations will be drawn from the vena saphena at day -3, day 18 and day 25. Native β2GPI (15 μg), reduced/alkylated β2GPI (15 μg) and native β2GPI (15 μg) with 1.35 μg CL will be administered intravenously at day 0, day 4, day 14 and day 18. The β2GPI and CL will be premixed and incubated at 400 $\mu g\ ml^{-1}$ and 25 μM final concentrations. Blood will be drawn at day −3, day 9, day 25. At first, titers will be determined with ELISAs using plates coated with the native proteins.

From our analyses, we conclude that β2GPI with CL, dOVA, alkyl-MSA, heat/acid-denatured glucagon and heat-denatured Etanercept comprise the cross-β structure conformation. The presence of the cross-β structure conformation can be further established by circular dichroism spectropolarimetry analyzes, X-ray fiber diffraction experiments, Fourier transform infrared spectroscopy, Congo red fluorescence/birefringence, tPA binding, factor XII activation and binding, and more.

The present invention discloses that proteins containing cross-β structure conformation are immunogenic. For a person skilled in the art it is now evident that further evidence can be obtained that support the proposed role for the cross-β structure conformation in immunogenicity. For example, the immunogenicity of proteins, including OVA, β2GPI and/or protein therapeutics such as interferon α, glucagon or Etanercept can be tested in vivo as described above, but also in vitro. Preferably, such experiments are performed with the native state of these proteins and compared with a state in which the cross-β structure conformation has been introduced. Preferably, the cross-β structure conformation is induced by heating, oxidation, glycation or treatment with an adjuvant, such as CPG-ODN oligodeoxynucleotides, LPS or CL. The content of cross-β structure conformation is preferably measured by ThT, Congo red, TEM, size exclusion chromatography, tPA-activating activity, and or binding of any other cross-β structure-binding protein listed in Tables 1-3. The immunogenicity of the protein is tested preferably in vitro and in vivo. For a person skilled in the art several in vitro assays are preferable to determine the immunogenicity of the protein in vitro. Preferably, activation of antigen presenting cells (APC), preferably dendritic cells (DC) is tested following treatment with the native or cross-β structure comprising protein. Preferably, this is performed according to established protocols. Activation of antigen presenting cells can be determined by FACS (Fluorescence Activated Cell Sorter) analysis. Preferably, the levels of so-called co-stimulatory molecules, such as B7.1, B7.2, MHC class 11, CD40, CD80, CD86 are determined on preferably CD11c positive cells. Alternatively, activation of NF-κB and/or expression of cytokines can be used as indicators of activation of cells involved in immunogenicity, such as APC and DC. Preferably, the following cytokines should be quantified: TNFα, IL-1, IL-2, IL-6, or IFNγ or other. Preferably, the cytokine levels should be quantified by ELISA. Alternatively, the mRNA levels are quantified. For a person skilled in the art it is evident that function of APC and DC can be tested as well. Preferably, the cross-presentation of antigen can be tested. Preferably, this can be achieved using OVA, in its native conformation and conformations with cross-β structure conformation, as model protein. The ability of DC or APC to activate MHC class I-restricted or MHC class II-restricted T-cells should be analyzed. For a person skilled in the art this can be done according to established protocols. The role of proteins with cross-β structure conformation in the activation of APC and their role in antigen presentation are further addressed with these aforementioned experimental procedures using cross-β structure-binding compounds in competition assays. Preferably, DC activation and functional antigen presentation are tested in the presence or absence of ThT, Congo red, tPA, or any other cross-β structure-binding protein, including those listed in Table 1-3 or a functional equivalent thereof.

The immunogenicity of proteins with cross-β structure conformation can also be further demonstrated in vivo. For example, the induction of antibodies and the induction of cytotoxic T lymphocyte (CTL) activity upon immunization of proteins, including OVA, β2GPI and/or protein therapeutics such as interferon α, glucagons, factor VIII, erythropoietin, thrombopoietin, GH or Etanercept can be tested as described already briefly above. Preferably, the immunogenicity of the native state of these proteins is compared with a state in which the cross-β structure conformation has been introduced. Preferably, the cross-β structure conformation is induced by heating, oxidation, glycation or treatment with an adjuvant, such as CpG-ODN, LPS or CL. The content of cross-β structure conformation is preferably measured by ThT, Congo Red, TEM, size exclusion chromatography, tPA-activating activity, and or binding of any other cross-β structure-binding protein listed in Tables 1-3. Preferably, the antibody titers are measured after immunization by ELISA and the CTL activity is measured using $^{51}$Cr-release assay. Alternatively the release of cytokines, including IL-2 can be measured.

REFERENCE LIST

1. Bouma B. et al. Glycation induces formation of amyloid cross-beta structure in albumin. *J. Biol. Chem.* 278, 41810-41819 (2003).
2. Nilsson M. R. Techniques to study amyloid fibril formation in vitro. *Methods* 34, 151-160 (2004).
3. Bucciantini M. et al. Inherent toxicity of aggregates implies a common mechanism for protein misfolding diseases. *Nature* 416, 507-511 (2002).
4. Cribbs D. H., B. Y. Azizeh, C. W. Cotman, and F. M. LaFerla. Fibril formation and neurotoxicity by a herpes simplex virus glycoprotein B fragment with homology to the Alzheimer's A beta peptide. *Biochemistry* 39, 5988-5994 (2000).
5. Kayed R. et al. Common structure of soluble amyloid oligomers implies common mechanism of pathogenesis. *Science* 300, 486-489 (2003).
6. Kranenburg O. et al. Recombinant endostatin forms amyloid fibrils that bind and are cytotoxic to murine neuroblastoma cells in vitro. *FEBS Lett.* 539, 149-155 (2003).
7. Kranenburg O. et al. Tissue-type plasminogen activator is a multiligand cross-beta structure receptor. *Curr. Biol.* 12, 1833-1839 (2002).
8. Townsend K. P. et al. CD40 signaling regulates innate and adaptive activation of microglia in response to amyloid beta-peptide. *Eur. J. Immunol.* 35, 901-910 (2005).
9. Subang R. et al. Phospholipid-bound beta 2-glycoprotein I induces the production of anti-phospholipid antibodies. *J. Autoimmun.* 15, 21-32 (2000).
10. Schielen J. G., H. P. Adams, M. Voskuilen, G. J. Tesser and W. Nieuwenhuizen. Structural requirements of position A alpha-157 in fibrinogen for the fibrin-induced rate enhancement of the activation of plasminogen by tissue-type plasminogen activator. *Biochem. J.* 276, 655-659 (1991).
11. de Laat B., R. H. Derksen, R. T. Urbanus and P. G. de Groot. IgG antibodies that recognize epitope Gly40-Arg43 in domain I of {beta}2-glycoprotein I cause LAC and their presence correlates strongly with thrombosis. *Blood* (2004).
12. Horbach D. A., E. van Oort, R. C. Donders, R. H. Derksen and P. G. de Groot. Lupus anticoagulant is the strongest risk factor for both venous and arterial thrombosis in patients with systemic lupus erythematosus. Comparison between different assays for the detection of antiphospholipid antibodies. *Thromb. Haemost.* 76, 916-924 (1996).
13. Horbach D. A., E. van Oort, M. J. Tempelman, R. H. Derksen and P. G. de Groot. The prevalence of a non-phospholipid-binding form of beta2-glycoprotein I in human plasma—consequences for the development of anti-beta2-glycoprotein I antibodies. *Thromb. Haemost.* 80, 791-797 (1998).
14. de Laat H. B., R. H. Derksen, R. T. Urbanus, M. Roest and P. G. de Groot. beta2-glycoprotein I-dependent lupus anticoagulant highly correlates with thrombosis in the antiphospholipid syndrome. *Blood* 104, 3598-3602 (2004).
15. Brandenburg K., M. H. Koch and U. Seydel. Biophysical characterisation of lysozyme binding to LPS Re and lipid A. *Eur. J. Biochem.* 258, 686-695 (1998).
16. Scibienski R. J. Denaturation of lysozyme by Freund's complete adjuvant. *J. Immunol.* 111, 114-120 (1973).
17. Morrison D. C. and C. G. Cochrane. Direct evidence for Hageman factor (factor XII) activation by bacterial lipopolysaccharides (endotoxins). *J. Exp. Med.* 140, 797-811 (1974).
18. Jurgens G. et al. Investigation into the interaction of recombinant human serum albumin with Re-lipopolysaccharide and lipid A. *J. Endotoxin. Res.* 8, 115-126 (2002).
19. Butovsky O., A. E. Talpalar, K. Ben Yaakov and M. Schwartz. Activation of microglia by aggregated beta-amyloid or lipopolysaccharide impairs MHC-II expression and renders them cytotoxic whereas IFN-gamma and IL-4 render them protective. *Mol. Cell Neurosci.* (2005).
20. Fassbender K. et al. The LPS receptor (CD14) links innate immunity with Alzheimer's disease. *FASEB J.* 18, 203-205 (2004).
21. Liu Y. et al. LPS receptor (CD14): a receptor for phagocytosis of Alzheimer's amyloid peptide. *Brain* (2005).
22. Matsuura E., Y. Igarashi, T. Yasuda, D.A. Triplett and T. Koike. Anticardiolipin antibodies recognize beta 2-glycoprotein I structure altered by interacting with an oxygen modified solid phase surface. *J. Exp. Med.* 179, 457-462 (1994).
23. Matzinger P. An innate sense of danger. *Ann. N.Y. Acad. Sci.* 961:341-2, 341-342 (2002).
24. Bouma B. et al. Adhesion mechanism of human beta(2)-glycoprotein I to phospholipids based on its crystal structure. *EMBO J.* 18, 5166-5174 (1999).

---

What is claimed is:

1. A method for determining that a protein with cross-beta structure was introduced to a pharmaceutical composition and/or any constituent of the pharmaceutical composition during the manufacture and/or storage of the pharmaceutical composition and/or any constituent of the pharmaceutical composition, said method comprising:

contacting said pharmaceutical composition and/or said constituent of the pharmaceutical composition with at least one cross-beta structure-binding compound, wherein the at least one cross-beta structure-binding compound is selected from the group consisting of: 2-(4'-(methylamino)phenyl)-6-methylbenzothiaziole, Thioflavin S, Polythiophene acetic acid, Thiophene acetic acid, Chrysamine G, a styryl dye, conjugated polyelectrolyte lithium salt of poly(thiophene-3 acetic acid) (PTAA-Li), glycosaminoglycans, BTA-1, Tissue-type plasminogen activator, Factor XII, Fibronectin, a hepatocyte growth factor activator, Serum amyloid P component, Clq, CD36, Receptor for advanced glycation endproducts, Scavenger receptor-A, Scavenger receptor-B, Calreticulin, Hybridoma conformational antibody WO1, formyl peptide receptor-like 1, Aβ-purified Rabbit anti-albumin-AGE antibody, apoJ/clusterin, a Finger domain of tPA, factor XII, fibronectin, Plasmin, Plasminogen, 75kD-neurotrophin receptor (p75NTR), α2-macroglobulin, High molecular weight kininogen, Cathepsin K, Matrix metalloprotease 9, Haem oxygenase-1, low-density lipoprotein receptor-related protein (LRP), vascular endothelial growth factor 165 (VEGF165), Hybridoma conformational antibody WO2, α(6)β(1)-integrin, CD40/CD40-ligand, tissue-type plasminogen activator (tPA) in complex with D-Phenylalanyl-L-prolyl-L-arginine chloromethyl ketone (PPACK), and epsilon-amino caproic acid (εACA), Apolipoprotein E, Matrix metalloprotease-1, Matrix metalloprotease-2, Matrix metalloprotease-3, Amyloid oligomer-specific antibody, CD47, apolipoprotein A-I (Apo A-I) belonging to small high-density lipoproteins, FEEL-1, lectin-like oxidized low-density lipoprotein receptor 1 (LOX-1), lymphocyte antigen 96 (MD2), fasciclin EGF-like laminin-type EGF-like and link domain-containing scavenger receptor-2 (FEEL-2), macrophage receptor with collagenous structure (MARCO), C reactive protein, Lysozyme, Tamm-Horsfall protein, CD11b2, Pentraxin-3, Serum amyloid A proteins, Stabilin-1, Stabilin-2, LPS-binding protein, CD45, alpha-1 antitrypsin, Alpha-1 acid glycoprotein, lactoferrin, Complement receptor CD11b/CD18 (Mac-1, CR3), CD11a/CD18 (LFA-1, subunit aL), CD36, LIMPII analogous-I (CLA-1), CD14, orosomucoid, apo A-IV-TTR complex, β2-glycoprotein I, megalin, Apolipoprotein E4, CD11d/CD18 (subunit aD), integrin aX subunit (CD11c), and Von Willebrand factor; and detecting if a protein with cross-beta structure of said pharmaceutical composition and/or said constituent of the pharmaceutical composition is bound to said cross-beta structure-binding compound, wherein detected binding of said protein with cross-beta structure to said cross-beta structure-binding compound indicates that the protein with cross-beta structure is present in the pharmaceutical composition and/or any constituent of the pharmaceutical composition, and wherein presence of the protein with cross-beta structure in the pharmaceutical composition and/or any constituent of the pharmaceutical composition indicates that the protein with cross-beta structure was introduced to the pharmaceutical composition and/or any constituent of the pharmaceutical composition during the manufacture and/or storage of the pharmaceutical composition and/or any constituent of the pharmaceutical composition.

2. The method according to claim 1 further comprising: removing said bound protein with cross-beta structure from said pharmaceutical composition.

3. The method according to claim 2, wherein said cross-beta structure binding compound is bound to a second compound.

4. The method according to claim 3, wherein said second compound is bound to a solid phase.

5. The method according to claim 1, wherein said cross-beta structure binding compound is bound to a second compound.

6. The method according to claim 5, wherein said second compound is bound to a solid phase.

7. The method according to claim 1, wherein the pharmaceutical composition and/or the constituent of the pharmaceutical composition comprises a protein therapeutic.

8. A method for controlling a manufacturing process, and/or storage process of a pharmaceutical composition comprising a protein therapeutic and/or any constituent of the pharmaceutical composition comprising a protein therapeutic, wherein the method comprises:

obtaining a sample from the pharmaceutical composition comprising a protein therapeutic, and/or any constituent of the pharmaceutical composition comprising a protein therapeutic, at a stage or stages of the manufacturing process and/or storage process of the pharmaceutical composition comprising a protein therapeutic, and/or any constituent of the pharmaceutical composition comprising a protein therapeutic;

contacting said sample obtained from the pharmaceutical composition comprising a protein therapeutic and/or any constituent of the pharmaceutical composition comprising a protein therapeutic with at least one cross-beta structure-binding compound resulting in a bound protein with cross-beta structure, wherein the at least one cross-beta structure-binding compound is selected from the group consisting of: 2-(4'-(methylamino)phenyl)-6-methylbenzothiaziole, Thioflavin S, Polythiophene acetic acid, Thiophene acetic acid, Chrysamine G, a styryl dye, conjugated polyelectrolyte lithium salt of poly(thiophene-3 acetic acid) (PTAA-Li), glycosaminoglycans, BTA-1, Tissue-type plasminogen activator, Factor XII, Fibronectin, a hepatocyte growth factor activator, Serum amyloid P component, Clq, CD36, Receptor for advanced glycation end-products, Scavenger receptor-A, Scavenger receptor-B, Calreticulin, Hybridoma conformational antibody WO1, formyl peptide receptor-like 1, Aβ-purified Rabbit anti-albumin-AGE antibody, apoJ/clusterin, a Finger domain of tPA, factor XII, fibronectin, Plasmin, Plasminogen, 75kD-neurotrophin receptor (p75NTR), α2-macroglobulin, High molecular weight kininogen, Cathepsin K, Matrix metalloprotease 9, Haem oxygenase-1, low-density lipoprotein receptor-related protein (LRP), vascular endothelial growth factor 165 (VEGF165), Hybridoma conformational antibody WO2, α(6)β(1)-integrin, CD40/CD40-ligand, tissue-type plasminogen activator (tPA) in complex with D-Phenylalanyl-L-prolyl-L-arginine chloromethyl ketone (PPACK), and epsilon-amino caproic acid (εACA), Apolipoprotein E, Matrix metalloprotease-1, Matrix metalloprotease-2, Matrix metalloprotease-3, Amyloid oligomer-specific antibody, CD47, apolipoprotein A-I (Apo A-I) belonging to small high-density lipoproteins, FEEL-1, lectin-like oxidized low-density lipoprotein receptor 1 (LOX-1), lymphocyte antigen 96 (MD2), fasciclin EGF-like laminin-type EGF-like and link domain-containing scavenger receptor-2 (FEEL-2), macrophage receptor with collagenous structure (MARCO), C reactive protein, Lysozyme, Tamm-Horsfall protein, CD11b2, Pentraxin-3, Serum amyloid A proteins, Stabilin-1, Stabilin-2, LPS-binding protein, CD45, alpha-1 antitrypsin, Alpha-1 acid glycoprotein, lactoferrin, Complement receptor CD11b/CD18 (Mac-1, CR3), CD11a/CD18 (LFA-1, subunit aL), CD36, LIMPII analogous-I (CLA-1), CD14, orosomucoid, apo A-IV-TTR complex, β2-glycoprotein I, megalin, Apolipoprotein E4, CD11d/CD18 (subunit aD), integrin aX subunit (CD11c), and Von Willebrand factor; and detecting if said bound protein with cross-beta structure is present in said sample obtained from the pharmaceutical composition comprising a protein therapeutic and/or any constituent of the pharmaceutical composition comprising a protein therapeutic at a stage or stages of the manufacturing process and/or storage process of the pharmaceutical composition comprising a protein therapeutic, and/or any constituent of the pharmaceutical composition comprising a protein therapeutic thereby identifying misfolded molecules having increased amounts of cross-beta structure so that misfolded molecules can be removed from the pharmaceutical composition or constituent thereof to control quality during the manufacturing and/or storage process.

9. The method according to claim 8, further comprising removing said bound protein with a cross-beta structure from said pharmaceutical composition.

10. A method for monitoring the manufacture and/or storage of a pharmaceutical composition comprising a protein therapeutic and/or a constituent of the pharmaceutical composition comprising a protein therapeutic, to determine whether a protein comprising cross-beta structure is present in the pharmaceutical composition comprising a protein therapeutic, and/or the constituent of the pharmaceutical composition comprising a protein therapeutic, the method comprising:

contacting the pharmaceutical composition and/or the constituent of the pharmaceutical composition with at least one cross-beta structure-binding compound, wherein the at least one cross-beta structure-binding compound is selected from the group consisting of: 2-(4'-(methylamino)phenyl)-6-methylbenzothiaziole, Thioflavin S, Polythiophene acetic acid, Thiophene acetic acid, Chrysamine G, a styryl dye, conjugated polyelectrolyte lithium salt of poly(thiophene-3 acetic acid) (PTAA-Li), glycosaminoglycans, BTA-1, Tissue-type plasminogen activator, Factor XII, Fibronectin, a hepatocyte growth factor activator, Serum amyloid P component, Clq, CD36, Receptor for advanced glycation end-products, Scavenger receptor-A, Scavenger receptor-B, Calreticulin, Hybridoma conformational antibody WO1, formyl peptide receptor-like 1, Aβ-purified Rabbit anti-albumin-AGE antibody, apoJ/clusterin, a Finger domain of tPA, factor XII, fibronectin, Plasmin, Plasminogen, 75kD-neurotrophin receptor (p75NTR), α2-macroglobulin, High molecular weight kininogen, Cathepsin K, Matrix metalloprotease 9, Haem oxygenase-1, low-density lipoprotein receptor-related protein (LRP), vascular endothelial growth factor 165 (VEGF165), Hybridoma conformational antibody WO2, α(6)β(1)-integrin, CD40/CD40-ligand, tissue-type plasminogen activator (tPA) in complex with D-Phenylalanyl-L-prolyl-L-arginine chloromethyl ketone (PPACK), and epsilon-amino caproic acid (εACA), Apolipoprotein E, Matrix metalloprotease-1, Matrix metalloprotease-2, Matrix metalloprotease-3, Amyloid oligomer-specific antibody, CD47, apolipoprotein A-I (Apo A-I) belonging to small high-density lipoproteins, FEEL-1, lectin-like oxidized low-density lipoprotein receptor 1 (LOX-1), lymphocyte antigen 96 (MD2), fasciclin EGF-like laminin-type EGF-like and link domain-containing scavenger receptor-2 (FEEL-2), macrophage receptor with collagenous structure (MARCO), C reactive protein, Lysozyme, Tamm-Horsfall protein, CD11b2, Pentraxin-3, Serum amyloid A proteins, Stabilin-1, Stabilin-2, LPS-binding protein, CD45, alpha-1 antitrypsin, Alpha-1 acid glycoprotein, lactoferrin, Complement receptor CD11b/CD18 (Mac-1, CR3), CD11a/CD18 (LFA-1, subunit aL), CD36, LIMPII analogous-I (CLA-1), CD14, orosomucoid, apo A-IV-TTR complex, β2-glycoprotein I, megalin, Apolipoprotein E4, CD11d/CD18 (subunit aD), integrin aX subunit (CD11c), and Von Willebrand factor, and detecting if the protein with cross-beta structure of the pharmaceutical composition and/or the protein with cross-beta structure of the constituent of the pharmaceutical composition is bound to the cross-beta structure-binding compound during the manufacture and/or the storage of the pharmaceutical composition and/or constituent of the pharmaceutical composition, wherein the presence of bound protein with cross-beta structure indicates that the pharmaceutical composition and/or constituent of the pharmaceutical composition comprises a protein with cross-beta structure, thus monitoring the manufacture and/or storage of the pharmaceutical composition or constituent thereof.

11. A method for determining whether a protein with cross-beta structure was introduced to a pharmaceutical composition and/or any constituent of the pharmaceutical composition during the manufacture and/or storage of the pharmaceutical composition and/or the constituent thereof, the method comprising:

contacting the pharmaceutical composition and/or the constituent thereof with at least one cross-beta structure-binding compound selected from the group consisting of: 2-(4'-(methylamino)phenyl)-6-methylbenzothiaziole, Thioflavin S, Polythiophene acetic acid, Thiophene acetic acid, Chrysamine G, a styryl dye, conjugated polyelectrolyte lithium salt of poly(thiophene-3 acetic acid) (PTAA-Li), glycosaminoglycans, BTA-1, Tissue-type plasminogen activator, Factor XII, Fibronectin, a hepatocyte growth factor activator, Serum amyloid P component, Clq, CD36, Receptor for advanced glycation end-products, Scavenger receptor-A, Scavenger receptor-B, Calreticulin, Hybridoma conformational antibody WO1, formyl peptide receptor-like 1, Aβ-purified Rabbit anti-albumin-AGE antibody, apoJ/clusterin, a Finger domain of tPA, factor XII, fibronectin, Plasmin, Plasminogen, 75kD-neurotrophin receptor (p75NTR), α2-macroglobulin, High molecular weight kininogen, Cathepsin K, Matrix metalloprotease 9, Haem oxygenase-1, low-density lipoprotein receptor-related protein (LRP), vascular endothelial growth factor 165 (VEGF165), Hybridoma conformational antibody WO2, α(6)β(1)-integrin, CD40/CD40-ligand, tissue-type plasminogen activator (tPA) in complex with D-Phenylalanyl-L-prolyl-L-arginine chloromethyl ketone (PPACK), and epsilon-amino caproic acid (εACA), Apolipoprotein E, Matrix metalloprotease-1, Matrix metalloprotease-2, Matrix metalloprotease-3, Amyloid oligomer-specific antibody, CD47, apolipoprotein A-I (Apo A-I) belonging to small high-density lipoproteins, FEEL-1, lectin-like oxidized low-density lipoprotein receptor 1 (LOX-1), lymphocyte antigen 96 (MD2), fasciclin EGF-like laminin-type EGF-like and link domain-containing scavenger receptor-2 (FEEL-2), macrophage receptor with collagenous structure (MARCO), C reactive protein, Lysozyme, Tamm-Horsfall protein, CD11b2, Pentraxin-3, Serum amyloid A proteins, Stabilin-1, Stabilin-2, LPS-binding protein, CD45, alpha-1 antitrypsin, Alpha-1 acid glycoprotein, lactoferrin, Complement receptor CD11b/CD18 Mac-1, CR3), CD11/a/CD18 (LFA-1, subunit aL), CD36, LIMPII analogous-I (CLA-1), CD14, orosomucoid, apo A-IV-TTR complex, β2-glycoprotein I, megalin, Apolipoprotein E4, CD11d/CD18 (subunit aD), integrin aX subunit (CD11c), and Von Willebrand factor; and detecting if the protein with cross-beta structure is bound to the cross-beta structure-binding compound, wherein detected binding of the protein with cross-beta structure to the cross-beta structure-binding compound indicates that the protein with cross-beta structure is present in the pharmaceutical composition and/or any constituent of the pharmaceutical composition, and wherein presence of the protein with cross-beta structure in the pharmaceutical composition and/or any constituent of the pharmaceutical composition indicates that the protein with cross-beta structure was introduced to the pharmaceutical composition and/or any constituent of the pharmaceutical composition during the manufacture and/or storage of the pharmaceutical composition and/or any constituent of the pharmaceutical composition.

* * * * *

UNITED STATES PATENT AND TRADEMARK OFFICE

CERTIFICATE OF CORRECTION

PATENT NO. : 8,114,832 B2
APPLICATION NO. : 11/181040
DATED : February 14, 2012
INVENTOR(S) : Martijn Frans Ben Gerard Gebbink and Barend Bouma It is certified that error appears in the above-identified patent and that said Letters Patent is hereby corrected as shown below:

On the title page:
In ITEM (56) References Cited
OTHER PUBLICATIONS

| | |
|---|---|
| Page 3, 1st column, 2nd line of the 3rd entry (line 7) | Change "Death. Differ. ," to --Death Differ.,-- |
| Page 3, 1st column, 2nd line of the 18th entry (line 45) | Change "A(1.42)." to --A(1-42).-- |
| Page 3, 1st column, 2nd line of the 19th entry (line 48) | Change "2229.36," to --2229-36,-- |
| Page 3, 1st column, 1st line of the 23rd entry (line 58) | Change "HSP27-parkin" to --HSP27, parkin-- |
| Page 3, 1st column, 2nd line of the 23rd entry (line 59) | Change "γ-glutanyl-c-lysine" to --γ-glutanyl-ε-lysine-- |
| Page 4, 1st column, 3rd line of the 23rd entry (line 61) | Change "579-894," to --879-894,-- |
| Page 4, 2nd column, 1st line of the 22nd entry (line 68) | Change "Tae Yoon" to --Tae-Yoon-- |
| Page 5, 2nd column, 1st line of the 25th entry (line 66) | Change "Scarch" to --Search-- |
| Page 6, 1st column, 1st line of the 8th entry (line 17) | Change "European" to --"No grip, no growth: the conceptual basis of excessive proteolysis in the treatment of cancer," European-- |
| Page 6, 1st column, 1st line of the 15th entry (line 35) | Change "front" to --from-- |

Signed and Sealed this
Nineteenth Day of February, 2013

Teresa Stanek Rea
*Acting Director of the United States Patent and Trademark Office*

CERTIFICATE OF CORRECTION (continued)

U.S. Pat. No. 8,114,832 B2

On the title page:

In ITEM (56) References Cited

OTHER PUBLICATIONS

| | |
|---|---|
| Page 6, $1^{st}$ column, $1^{st}$ line of the $17^{th}$ entry (line 50) | Change “EMBO” to --“Involvement of finger domain and kringle 2 domain of tissue-type plasminogen activator in fibrin binding and stimulation of activity by fibrin,” EMBO-- |
| Page 7, $1^{st}$ column, $3^{rd}$ line of the $1^{st}$ entry (line 3) | Change “Microbipl.,” to --Microbiol.,-- |
| Page 8, $1^{st}$ column, $1^{st}$ line of the $16^{th}$ entry (line 41) | Change “Ami-angiogenic” to --Anti-angiogenic-- |
| New Entry, | Insert --Elghetany et al., Methods for Staining Amyloid in Tissues: A Review, Stain Technology, January 1, 1988, pp. 201-211, Vol. 63, No. 4.-- |
| New Entry, | Insert --KLUNK et al., Development of Small Molecule Probes for the Beta-Amyloid Protein of Alzheimer’s Disease, Neurobiology of Aging, 1994, pp. 691-98, Vol. 15, No. 6, Elsevier Science Ltd., USA.-- |
| New Entry, | Insert --Office Action for Application No. 11/181,040 dated 01/12/2009.-- |
| New Entry, | Insert --Office Action for Application No. 11/181,040 dated 05/31/2007.-- |
| New Entry, | Insert --Office Action for Application No. 11/181,040 dated 06/23/2010.-- |
| New Entry, | Insert --Office Action for Application No. 11/181,040 dated 07/15/2008.-- |
| New Entry, | Insert --Office Action for Application No. 11/181,040 dated 10/29/2009.-- |
| New Entry, | Insert --Office Action for Application No. 11/181,040 dated 11/27/2007.-- |
| New Entry, | Insert --Office Action for Application No. 11/384,169 dated 06/10/2009.-- |
| New Entry, | Insert --Office Action for Application No. 11/384,169 dated 10/28/2008.-- |
| New Entry, | Insert --Office Action for Application No. 11/995,308 dated 10/1/2010.-- |

In the specification:

| | |
|---|---|
| COLUMN 3, LINE 37, | Change “(CpGODN)” to --(CpG-ODN)-- |
| COLUMN 5, LINE 32, | Change “/WORLD$^{13}$ ACCESS/” to --/WORLD_ACCESS/-- |